US009493411B2

(12) United States Patent
Hasvold et al.

(10) Patent No.: US 9,493,411 B2
(45) Date of Patent: Nov. 15, 2016

(54) PYRROLE-3-CARBOXAMIDE BROMODOMAIN INHIBITORS

(71) Applicant: AbbVie Inc., North Chicago, IL (US)

(72) Inventors: Lisa A. Hasvold, Grayslake, IL (US); John Pratt, Kenosha, WI (US); Keith F. McDaniel, Wauconda, IL (US); George S. Sheppard, Wilmette, IL (US); Dachun Liu, Vernon Hills, IL (US); Steven W. Elmore, Northbrook, IL (US); Robert D. Hubbard, San Diego, CA (US)

(73) Assignee: AbbVie Inc., North Chicago, IL (US)

(*) Notice: Subject to any disclaimer, the term of this patent is extended or adjusted under 35 U.S.C. 154(b) by 56 days.

(21) Appl. No.: 14/206,061

(22) Filed: Mar. 12, 2014

(65) Prior Publication Data

US 2014/0275079 A1  Sep. 18, 2014

Related U.S. Application Data

(63) Continuation of application No. 61/777,749, filed on Mar. 12, 2013.

(51) Int. Cl.

| C07D 207/335 | (2006.01) |
|---|---|
| C07D 207/36 | (2006.01) |
| C07D 207/34 | (2006.01) |
| C07D 401/04 | (2006.01) |
| C07D 403/04 | (2006.01) |
| C07D 405/04 | (2006.01) |
| C07D 407/04 | (2006.01) |
| C07D 409/04 | (2006.01) |
| C07D 413/04 | (2006.01) |
| C07D 471/04 | (2006.01) |
| A61K 31/496 | (2006.01) |
| A61K 31/506 | (2006.01) |
| A61K 31/381 | (2006.01) |
| A61K 31/341 | (2006.01) |
| A61K 31/422 | (2006.01) |
| A61K 31/4709 | (2006.01) |
| C07D 401/12 | (2006.01) |
| C07D 403/12 | (2006.01) |
| C07D 405/12 | (2006.01) |
| C07D 409/12 | (2006.01) |
| C07D 413/12 | (2006.01) |
| C07D 401/10 | (2006.01) |
| C07D 403/10 | (2006.01) |
| C07D 407/12 | (2006.01) |
| C07D 409/10 | (2006.01) |
| C07D 413/10 | (2006.01) |

(52) U.S. Cl.
CPC ............ *C07D 207/34* (2013.01); *C07D 207/36* (2013.01); *C07D 401/10* (2013.01); *C07D 401/12* (2013.01); *C07D 403/04* (2013.01); *C07D 403/10* (2013.01); *C07D 403/12* (2013.01); *C07D 405/12* (2013.01); *C07D 407/12* (2013.01); *C07D 409/10* (2013.01); *C07D 409/12* (2013.01); *C07D 413/10* (2013.01); *C07D 413/12* (2013.01); *C07D 471/04* (2013.01); *C07D 207/335* (2013.01)

(58) Field of Classification Search
CPC ............ C07D 295/023; C07D 265/30; C07D 295/027; C07D 213/74; C07D 207/335; C07D 207/36; C07D 401/04; C07D 403/04; C07D 405/04; C07D 407/04; C07D 409/04; C07D 413/04; C07D 471/04; C07C 213/02; A61K 31/4025; A61K 31/40; A61K 31/496; A61K 31/506; A61K 31/381; A61K 31/341; A61K 31/422; A61K 31/4709
USPC .............. 544/106, 372, 224, 333; 514/235.5, 514/423, 427, 247, 256, 326, 343, 444, 461, 514/378; 546/208, 276.4; 548/240, 577, 548/560, 517; 549/59, 472
See application file for complete search history.

(56) References Cited

FOREIGN PATENT DOCUMENTS

WO        2006129623 A1    12/2006
WO   WO 2008024978 A2 *    2/2008 ........... C07D 207/02

OTHER PUBLICATIONS

Aiello, E., G. Dattolo, G. Cirrincione and A. Almerico "Polycondensed Nitrogen Heterocycles. Part 13 [1]. Pyrrolo[3,2-b]indole by Intramolecular Nucleophilic Substitution Reaction in the Pyrrole Series" J. Heterocyclic Chem. (1984), 21(3), pp. 721-724.*
Menichincheri, M., et al. "Cdc7 Kinase Inhibitors: 5-Heteroaryl-3-Carboxamido-2-Aryl Pyrroles as Potential Antitumor Agents. 1. Lead Finding" J. Med. Chem (2010), 53, pp. 7296-7315.*

(Continued)

*Primary Examiner* — Alicia A Otton
*Assistant Examiner* — Sagar Patel
(74) *Attorney, Agent, or Firm* — Glen J. Gesicki

(57) ABSTRACT

The present invention provides for compounds of formula (I)

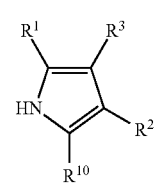

wherein $R^1$, $R^2$, $R^3$, and $R^{10}$ have any of the values defined in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

12 Claims, No Drawings

(56) References Cited

OTHER PUBLICATIONS

STN Registry Database entry for CAS RN 1116032-85-9, Published in database on Mar. 5, 2009.*
Banerjee C., et al., "BET Bromodomain Inhibition as a Novel Strategy for Reactivation of HIV-1," Journal of Leukocyte Biology, 2012, vol. 92 (6), pp. 1147-1154.
Berge, S. M. et al., "Pharmaceutical Salts," Journal of Pharmaceutical Sciences, 1977, vol. 66 (1), pp. 1-19.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Green, et al., "Protecting Groups in Organic Synthesis" in: Antibodies, 3rd Edition, John Wiley & Sons, NY, 1999, pp. 20.
Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Leroy G., et al., "The Double Bromodomain Proteins Brd2 and Brd3 Couple Histone Acetylation to Transcription," Molecular Cell, 2008, vol. 30 (1), pp. 51-60.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Miyaura N., et al., "Palladium-Catalyzed Cross-Coupling Reactions of Organoboron Compounds," Chemical Reviews, 1995, vol. 95 (7), pp. 2457-2483.
Nicodeme E., et al., "Suppression of Inflammation by a Synthetic Histone Mimic," Nature, 2010, vol. 468 (7327), pp. 1119-1123.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A, "Recent Advances in the Cross-Coupling Reactions of Organoboron Derivatives with Organic Electrophiles," Journal of Organometallic Chemistry, 1999, vol. 576, pp. 147-168.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.
Zuber J., et al., "RNAi Screen Identifies Brd4 as a Therapeutic Target in Acute Myeloid Leukaemia," Nature, 2011, vol. 478 (7370), pp. 524-528.

* cited by examiner

PYRROLE-3-CARBOXAMIDE BROMODOMAIN INHIBITORS

BACKGROUND

Bromodomains refer to conserved protein structural folds which bind to N-acetylated lysine residues that are found in some proteins. The BET family of bromodomain containing proteinfs is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or a pharmaceutically acceptable salt thereof:

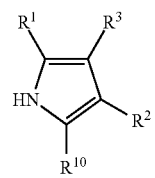

(I)

wherein
$R^1$ is $C_1$-$C_3$ alkyl;
$R^2$ is hydrogen or $C_1$-$C_3$ alkyl;
$R^3$ is —C(O)—$C_1$-$C_3$ alkyl, COOH, or —C(O)NR$^8$R$^9$;
$R^8$ and $R^9$ are chosen from one of the following groups:
  (i) $R^8$ and $R^9$ are both H;
  (ii) $R^8$ is H and $R^9$ is $C_1$-$C_3$ alkylene-C(O)O—$C_1$-$C_3$ alkyl or OH; and
  (iii) $R^8$ is $C_1$-$C_3$ alkylene-aryl and $R^9$ is $C_1$-$C_3$ alkylene-C(O)—$C_1$-$C_3$ alkyl;
$R^{10}$ is aryl or heteroaryl, wherein $R^{10}$ may be substituted with 1 to 3 substituents designated as $R^{40}$, $R^{41}$, and $R^{42}$ and independently selected from the group consisting of:
  $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—SO$_2$—$C_1$-$C_3$ alkyl, —NH—SO$_2$—$C_1$-$C_3$ haloalkyl, —SO$_2$—NH$_2$, —C(O)—NR$^{20}$R$^{22}$, and -L-R$^{12}$,
  wherein L is absent or is —$C_1$-$C_3$alkylene-, —$C_2$-$C_3$alkenylene-, —NH—, —NH—$C_1$-$C_3$alkylene-, —NR$^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and —O—;
  $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated R$^{15}$, R$^{16}$, and R$^{17}$,
  $R^{15}$, $R^{16}$, and $R^{17}$ are independently selected from the group consisting of:
    OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)OC$_1$-$C_4$ alkyl, —C(O)NH—$C_1$-$C_3$ alkylene-NR$^{30}$R$^{32}$, —C(O)NR$^{30}$R$^{32}$, —O—$C_1$-$C_4$ alkyl-NR$^{30}$N$^{32}$, —NR$^{30}$R$^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl,
    wherein said heterocycloalkyl, heteroaryl or aryl groups on R$^{15}$, R$^{16}$, and R$^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl, $R^{26}$ is $C_1$-$C_3$ alkylene-$C_3$-$C_6$ cycloalkyl;

$R^{20}$ and $R^{22}$ are independently selected from the group consisting of H and $C_1$-$C_6$ alkyl; and $R^{30}$ and $R^{32}$ are independently selected from the group consisting of H and $C_1$-$C_4$ alkyl.

In certain embodiments, $R^1$ is methyl. In certain embodiments, $R^2$ is hydrogen. In certain embodiments, $R^3$ is —C(O)NR$^8$R$^9$. In certain embodiments, $R^8$ and $R^9$ are both H. In certain embodiments, $R^{10}$ is heteroaryl, which may be substituted with 1 to 3 substituents designated as $R^{40}$, $R^{41}$, and $R^{42}$ and independently selected from the group consisting of: $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—SO$_2$—$C_1$-$C_3$ alkyl, —NH—SO$_2$—$C_1$-$C_3$ haloalkyl, —SO$_2$—NH$_2$, —C(O)—NR$^{20}$R$^{22}$, and -L-R$^{12}$, wherein L is absent or is —$C_1$-$C_3$alkylene-, —$C_2$-$C_3$alkenylene-, —NH—, —NH—$C_1$-$C_3$alkylene-, —NR$^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)OC$_1$-$C_4$ alkyl, —C(O)NH—$C_1$-$C_3$ alkylene-NR$^{30}$R$^{32}$, —C(O)NR$^{30}$R$^{32}$, —O—$C_1$-$C_4$ alkyl-NR$^{30}$N$^{32}$, —NR$^{30}$R$^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

In certain embodiments, $R^{10}$ is unsubstituted heteroaryl. In some such embodiments, the unsubstituted heteroaryl is benzimidazolyl or indolyl.

In certain embodiments, $R^{10}$ is phenyl which may be substituted with 1 to 3 substituents designated as $R^{40}$, $R^{41}$, and $R^{42}$ and independently selected from the group consisting of: $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—SO$_2$—$C_1$-$C_3$ alkyl, —NH—SO$_2$—$C_1$-$C_3$ haloalkyl, —SO$_2$—NH$_2$, —C(O)—NR$^{20}$R$^{22}$, and -L-R$^{12}$, wherein L is absent or is —$C_1$-$C_3$alkylene-, —$C_2$-$C_3$alkenylene-, —NH—, —NH—$C_1$-$C_3$alkylene-, —NR$^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)OC$_1$-$C_4$ alkyl, —C(O)NH—$C_1$-$C_3$ alkylene-NR$^{30}$R$^{32}$, —C(O)NR$^{30}$R$^{32}$, —O—$C_1$-$C_4$ alkyl-NR$^{30}$N$^{32}$, —NR$^{30}$R$^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

In certain embodiments, $R^{10}$ is phenyl which is substituted with one substituent, $R^{41}$, and optionally further substituted with 1 or 2 substituents designated as $R^{40}$ and $R^{42}$; wherein $R^{41}$ is -L-R$^{12}$;

$R^{40}$ is $NR^{20}R^{22}$, halo, $C_1$-$C_3$ alkylene-OH, $C_1$-$C_3$ alkylene-C(O)OH, $C_1$-$C_3$ alkylene-C(O)O—$C_1$-$C_4$ alkyl, —NHC(O)—$C_1$-$C_3$ alkyl, —NH—SO$_2$—$C_1$-$C_3$ alkyl, —NH—SO$_2$—$C_1$-$C_3$ haloalkyl, or —SO$_2$—NH$_2$; and $R^{42}$ is $C_1$-$C_6$ alkyl, $C_1$-$C_6$ haloalkyl, halo, or -L-R$^{12}$; wherein L is absent and $R^{12}$ is optionally substituted cyclopropyl.

In certain embodiments, $R^{10}$ is phenyl which is substituted with one substituent, $R^{41}$, and optionally further substituted with 1 or 2 substituents designated as $R^{40}$ and $R^{42}$; wherein $R^{41}$ is -L-R$^{12}$;

L is absent, —$C_2$-$C_3$alkenylene, —NH—, —NHS(O)$_2$—, —NH—C(O)—$C_1$-$C_3$alkylene, or O;

$R^{12}$ is $C_3$-$C_{10}$ cycloalkyl, 3 to 8 membered heterocycloalkyl, 5 to 12 membered heteroaryl, or aryl, each of which is optionally substituted; or $R^{12}$ is $C_1$-$C_6$ alkyl substituted with a substituent selected from the group consisting of $C_3$-$C_6$ cycloalkyl, 3 to 8 membered heterocycloalkyl, 5 to 12 membered heteroaryl, and aryl, wherein each of the $C_3$-$C_6$ cycloalkyl, 3 to 8 membered heterocycloalkyl, 5 to 12 membered heteroaryl, and aryl is optionally substituted;

$R^{40}$ is $NR^{20}R^{22}$, halo, $C_1$-$C_3$ alkylene-OH, $C_1$-$C_3$ alkylene-C(O)OH, $C_1$-$C_3$ alkylene-C(O)O—$C_1$-$C_4$ alkyl, —NHC(O)—$C_1$-$C_3$ alkyl, —NH—SO$_2$—$C_1$-$C_3$ alkyl, —NH—SO$_2$—$C_1$-$C_3$ haloalkyl, or —SO$_2$—NH$_2$; and $R^{42}$ is $C_1$-$C_6$ alkyl, $C_1$-$C_6$ haloalkyl, halo, or -L-R$^{12}$; wherein L is absent and $R^{12}$ is optionally substituted cyclopropyl.

In certain embodiments, $R^{10}$ is

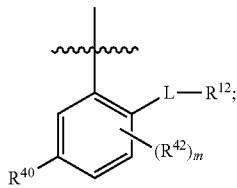

wherein
L is —NH— or O;
$R^{12}$ is phenyl, $C_3$-$C_6$ cycloalkyl, 5-membered heterocycloalkyl, or 6-membered heterocycloalkyl; each of which is optionally substituted; or $R^{12}$ is $C_1$-$C_3$ alkyl substituted with a substituent selected from the group consisting of phenyl, $C_3$-$C_6$ cycloalkyl, 5-membered heterocycloalkyl, and 6-membered heterocycloalkyl; wherein each of the phenyl, $C_3$-$C_6$ cycloalkyl, 5-membered heterocycloalkyl, and 6-membered heterocycloalkyl is optionally substituted;
m is 0 or 1;
$R^{42}$ is $C_1$-$C_6$ alkyl, $C_1$-$C_6$ haloalkyl, halo, or -L-$R^{12}$; wherein L is absent and $R^{12}$ is optionally substituted cyclopropyl, and
$R^{40}$ is $NR^{20}R^{22}$, halo, $C_1$-$C_3$ alkylene-OH, $C_1$-$C_3$ alkylene-C(O)OH, $C_1$-$C_3$ alkylene-C(O)O—$C_1$-$C_4$ alkyl, —NH—$SO_2$—$C_1$-$C_3$ alkyl, —NH—$SO_2$—$C_1$-$C_3$ haloalkyl, or —$SO_2$—$NH_2$.

In certain embodiments, $R^{10}$ is phenyl which is substituted with one substituent designated as $R^{41}$ and is depicted as:

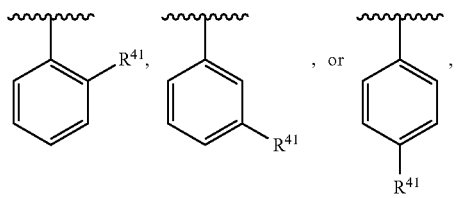

wherein $R^{41}$ is selected from the group consisting of: $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$ alkenylene-O—$C_1$-$C_3$ alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—$NH_2$, —C(O)—$NR^{20}R^{22}$, and -L-$R^{12}$,
wherein L is absent or is —$C_1$-$C_3$alkylene-, —$C_2$-$C_3$alkenylene-, —NH—, —NH—$C_1$-$C_3$alkylene-, —$NR^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl, or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

In certain embodiments, $R^{10}$ is phenyl which is substituted with one substituent designated as $R^{41}$ and is depicted as:

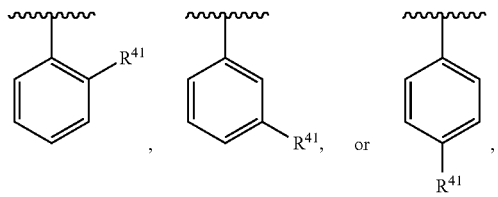

wherein $R^{41}$ is -L-$R^{12}$.

In certain embodiments, $R^{10}$ is phenyl which is substituted with one substituent designated as $R^{41}$ and is depicted as:

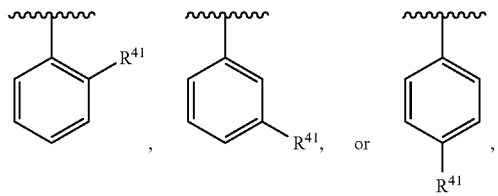

wherein
$R^{41}$ is -L-$R^{12}$;
L is absent, —$C_2$-$C_3$alkenylene, —NH—, —NHS(O)$_2$—, —NH—C(O)—$C_1$-$C_3$alkylene, or O; and
$R^{12}$ is $C_3$-$C_{10}$ cycloalkyl, 3 to 8 membered heterocycloalkyl, 5 to 12 membered heteroaryl, or aryl, each of which is optionally substituted; or $R^{12}$ is $C_1$-$C_6$ alkyl substituted with a substituent selected from the group consisting of $C_3$-$C_6$ cycloalkyl, 3 to 8 membered heterocycloalkyl, 5 to 12 membered heteroaryl, and aryl, wherein each of the $C_3$-$C_6$ cycloalkyl, 3 to 8 membered heterocycloalkyl, 5 to 12 membered heteroaryl, and aryl is optionally substituted.

In certain embodiments, $R^{10}$ is phenyl which is substituted with one substituent designated as $R^{41}$ and is depicted as:

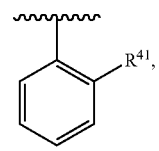

wherein $R^{41}$ is selected from the group consisting of: $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—$NH_2$, —C(O)—$NR^{20}R^{22}$, and -L-$R^{12}$, wherein L is absent or is —$C_1$-$C_3$alkylene-, —$C_2$-$C_3$alkenylene-, —NH—, —NH—$C_1$-$C_3$alkylene-, —$NR^{26}$—, —$NHS(O)_2$—, $NHS(O)_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—$S(O)_2$—$C_1$-$C_3$ alkyl, —NH—$S(O)_2$—$C_1$-$C_3$ haloalkyl, —$S(O)_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—$S(O)_2$—$C_1$-$C_3$ alkyl, —NH—$S(O)_2$—$C_1$-$C_3$ haloalkyl, and —$S(O)_2$—$C_1$-$C_3$ alkyl.

In certain embodiments, $R^{10}$ is phenyl which is substituted with one substituent designated as $R^{41}$ and is depicted as:

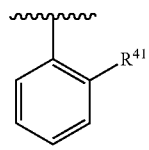

wherein $R^{41}$ is -L-$R^{12}$.

In certain embodiments, $R^{10}$ is phenyl which is substituted with one substituent designated as $R^{41}$ and is depicted as:

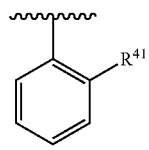

wherein
$R^{41}$ is -L-$R^{12}$;
L is absent, —$C_2$-$C_3$alkenylene, —NH—, —$NHS(O)_2$—, —NH—C(O)—$C_1$-$C_3$alkylene, or O; and $R^{12}$ is $C_3$-$C_{10}$ cycloalkyl, 3 to 8 membered heterocycloalkyl, 5 to 12 membered heteroaryl, or aryl, each of which is optionally substituted; or $R^{12}$ is $C_1$-$C_6$ alkyl substituted with a substituent selected from the group consisting of $C_3$-$C_6$ cycloalkyl, 3 to 8 membered heterocycloalkyl, 5 to 12 membered heteroaryl, and aryl, wherein each of the $C_3$-$C_6$ cycloalkyl, 3 to 8 membered heterocycloalkyl, 5 to 12 membered heteroaryl, and aryl is optionally substituted.

In certain embodiments, $R^{10}$ is phenyl which is substituted with one substituent designated as $R^{41}$ and is depicted as:

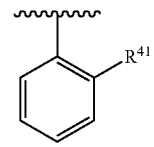

wherein
$R^{41}$ is -L-$R^{12}$;
L is —NH— or O; and
$R^{12}$ is phenyl, $C_3$-$C_6$ cycloalkyl, 5-membered heterocycloalkyl, or 6-membered heterocycloalkyl; each of which is optionally substituted; or $R^{12}$ is $C_1$-$C_3$ alkyl substituted with a substituent selected from the group consisting of phenyl, $C_3$-$C_6$ cycloalkyl, 5-membered heterocycloalkyl, and 6-membered heterocycloalkyl; wherein each of the phenyl, $C_3$-$C_6$ cycloalkyl, 5-membered heterocycloalkyl, and 6-membered heterocycloalkyl is optionally substituted.

In certain embodiments, $R^{10}$ is phenyl which is substituted with one substituent designated as $R^{41}$ and is depicted as:

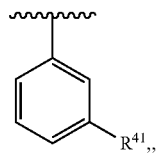

wherein $R^{41}$ is selected from the group consisting of: $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—$NH_2$, —C(O)—$NR^{20}R^{22}$, and -L-$R^{12}$, wherein L is absent or is —$C_1$-$C_3$alkylene-, —$C_2$-$C_3$alkenylene-, —NH—, —NH—$C_1$-$C_3$alkylene-, —$NR^{26}$—, —$NHS(O)_2$—, $NHS(O)_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-

$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

In certain embodiments, $R^{10}$ is phenyl which is substituted with one substituent designated as $R^{41}$ and is depicted as:

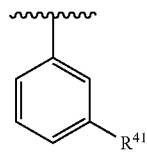

wherein $R^{41}$ is -L-$R^{12}$.

In certain embodiments, $R^{10}$ is phenyl which is substituted with one substituent designated as $R^{41}$ and is depicted as:

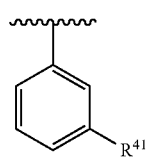

wherein
$R^{41}$ is -L-$R^{12}$;
L is absent, —$C_2$-$C_3$alkenylene, —NH—, —NHS(O)$_2$—, —NH—C(O)—$C_1$-$C_3$alkylene, or O; and
$R^{12}$ is $C_3$-$C_{10}$ cycloalkyl, 3 to 8 membered heterocycloalkyl, 5 to 12 membered heteroaryl, or aryl, each of which is optionally substituted; or $R^{12}$ is $C_1$-$C_6$ alkyl substituted with a substituent selected from the group consisting of $C_3$-$C_6$ cycloalkyl, 3 to 8 membered heterocycloalkyl, 5 to 12 membered heteroaryl, and aryl, wherein each of the $C_3$-$C_6$ cycloalkyl, 3 to 8 membered heterocycloalkyl, 5 to 12 membered heteroaryl, and aryl is optionally substituted.

In certain embodiments, $R^{10}$ is phenyl which is substituted with one substituent designated as $R^{41}$ and is depicted as:

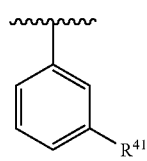

wherein
$R^{41}$ is -L-$R^{12}$;
L is absent or —$C_2$-$C_3$alkenylene; and
$R^{12}$ is 5 to 12 membered heteroaryl or phenyl, each of which is optionally substituted.

In certain embodiments, $R^{10}$ is phenyl which is substituted with one substituent designated as $R^{41}$ and is depicted as:

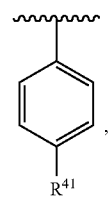

wherein $R^{41}$ is selected from the group consisting of: NO$_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—SO$_2$—$C_1$-$C_3$ alkyl, —NH—SO$_2$—$C_1$-$C_3$ haloalkyl, —SO$_2$—NH$_2$, —C(O)—$NR^{20}R^{22}$, and -L-$R^{12}$, wherein L is absent or is —$C_1$-$C_3$alkylene-, —$C_2$-$C_3$alkenylene-, —NH—, —NH—$C_1$-$C_3$alkylene-, —$NR^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and —O—; $R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which may be substituted with one, two, or three substituents designated $R^{15}$, $R^{16}$, and $R^{17}$; $R^{15}$, $R^{16}$, and $R^{17}$ are independently selected from the group consisting of: OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ may be independently substituted with 1 to 3 substituents selected from the group consisting of: $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

In certain embodiments, $R^{10}$ is phenyl which is substituted with one substituent designated as $R^{41}$ and is depicted as:

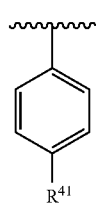

wherein $R^{41}$ is -L-$R^{12}$.

In certain embodiments, $R^{10}$ is phenyl which is substituted with one substituent designated as $R^{41}$ and is depicted as:

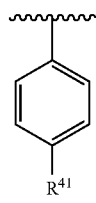

wherein
$R^{41}$ is -L-$R^{12}$;
L is absent, —$C_2$-$C_3$alkenylene, —NH—, —NHS(O)$_2$—, —NH—C(O)—$C_1$-$C_3$alkylene, or O; and
$R^{12}$ is $C_3$-$C_{10}$ cycloalkyl, 3 to 8 membered heterocycloalkyl, 5 to 12 membered heteroaryl, or aryl, each of which is optionally substituted; or $R^{12}$ is $C_1$-$C_6$ alkyl substituted with a substituent selected from the group consisting of $C_3$-$C_6$ cycloalkyl, 3 to 8 membered heterocycloalkyl, 5 to 12 membered heteroaryl, and aryl, wherein each of the $C_3$-$C_6$ cycloalkyl, 3 to 8 membered heterocycloalkyl, 5 to 12 membered heteroaryl, and aryl is optionally substituted.

In certain embodiments, $R^{10}$ is phenyl which is substituted with one substituent designated as $R^{41}$ and is depicted as:

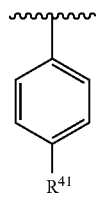

wherein
$R^{41}$ is -L-$R^{12}$;
L is absent; and
$R^{12}$ is 5 to 12 membered heteroaryl or phenyl, each of which is optionally substituted.

In certain embodiments, a compound of formula I is selected from the group consisting of:
5-(2-aminophenyl)-2-methyl-1H-pyrrole-3-carboxamide;
5-[2-(acetylamino)phenyl]-2-methyl-1H-pyrrole-3-carboxamide;
2-methyl-5-(3-nitrophenyl)-1H-pyrrole-3-carboxamide;
5-(3-aminophenyl)-2-methyl-1H-pyrrole-3-carboxamide;
5-[3-(acetylamino)phenyl]-2-methyl-1H-pyrrole-3-carboxamide;
2-methyl-5-{3-[(methylsulfonyl)amino]phenyl}-1H-pyrrole-3-carboxamide;
2-methyl-5-(4-nitrophenyl)-1H-pyrrole-3-carboxamide;
5-(4-aminophenyl)-2-methyl-1H-pyrrole-3-carboxamide;
2-methyl-5-{4-[(methylsulfonyl)amino]phenyl}-1H-pyrrole-3-carboxamide;
5-[4-(acetylamino)phenyl]-2-methyl-1H-pyrrole-3-carboxamide;
5-{2-[(4-chlorobenzyl)amino]phenyl}-2-methyl-1H-pyrrole-3-carboxamide;
5-[2-(benzylamino)phenyl]-2-methyl-1H-pyrrole-3-carboxamide;
2-methyl-5-{2-[(tetrahydrofuran-2-ylmethyl)amino]phenyl}-1H-pyrrole-3-carboxamide;
5-{2-[(cyclopentylmethyl)amino]phenyl}-2-methyl-1H-pyrrole-3-carboxamide;
5-(2-{[(4-bromothiophen-2-yl)methyl]amino}phenyl)-2-methyl-1H-pyrrole-3-carboxamide;
2-methyl-5-{2-[(3,4,5-trimethoxybenzyl)amino]phenyl}-1H-pyrrole-3-carboxamide;
2-methyl-5-{2-[(tetrahydrofuran-3-ylmethyl)amino]phenyl}-1H-pyrrole-3-carboxamide;
2-methyl-5-(2-{[(3R)-tetrahydrofuran-3-ylmethyl]amino}phenyl)-1H-pyrrole-3-carboxamide;
2-methyl-5-(2-{[(3S)-tetrahydrofuran-3-ylmethyl]amino}phenyl)-1H-pyrrole-3-carboxamide;
5-(2-{[(4,5-dimethylfuran-2-yl)methyl]amino}phenyl)-2-methyl-1H-pyrrole-3-carboxamide;
5-(2-{[3,5-bis(trifluoromethyl)benzyl]amino}phenyl)-2-methyl-1H-pyrrole-3-carboxamide;
5-{2-[2,6-difluorobenzyl)amino]phenyl}-2-methyl-1H-pyrrole-3-carboxamide;
5-{2-[(4-fluorobenzyl)amino]phenyl}-2-methyl-1H-pyrrole-3-carboxamide;
2-methyl-5-{2-[(2-methylbenzyl)amino]phenyl}-1H-pyrrole-3-carboxamide;
2-methyl-5-{2-[(3-methylbenzyl)amino]phenyl}-1H-pyrrole-3-carboxamide;
5-{2-[(cyclopropylmethyl)amino]phenyl}-2-methyl-1H-pyrrole-3-carboxamide;
5-[2-(butylamino)phenyl]-2-methyl-1H-pyrrole-3-carboxamide;
2-methyl-5-(2-{[4-(trifluoromethyl)benzyl]amino}phenyl)-1H-pyrrole-3-carboxamide;
2-methyl-5-{2-[(4-methylbenzyl)amino]phenyl}-1H-pyrrole-3-carboxamide;
5-{2-[(4-methoxybenzyl)amino]phenyl}-2-methyl-1H-pyrrole-3-carboxamide;
5-{2-[(4-cyanobenzyl)amino]phenyl}-2-methyl-1H-pyrrole-3-carboxamide;
5-{2-[(4-bromobenzyl)amino]phenyl}-2-methyl-1H-pyrrole-3-carboxamide;
5-{2-[(3,4-dichlorobenzyl)amino]phenyl}-2-methyl-1H-pyrrole-3-carboxamide;
5-{2-[(2-chlorobenzyl)amino]phenyl}-2-methyl-1H-pyrrole-3-carboxamide;
5-{2-[(3-chlorobenzyl)amino]phenyl}-2-methyl-1H-pyrrole-3-carboxamide;
5-{2-[(cyclohexylmethyl)amino]phenyl}-2-methyl-1H-pyrrole-3-carboxamide;
5-(2-{[4-(dimethylamino)benzyl]amino}phenyl)-2-methyl-1H-pyrrole-3-carboxamide;
2-methyl-5-{2-[(thiophen-2-ylmethyl)amino]phenyl}-1H-pyrrole-3-carboxamide;
5-{2-[(3,5-dichlorobenzyl)amino]phenyl}-2-methyl-1H-pyrrole-3-carboxamide;
tert-butyl 3-({[2-(4-carbamoyl-5-methyl-1H-pyrrol-2-yl)phenyl]amino}methyl)pyrrolidine-1-carboxylate;

tert-butyl 4-({[2-(4-carbamoyl-5-methyl-1H-pyrrol-2-yl)phenyl]amino}methyl)piperidine-1-carboxylate;
2-methyl-5-{2-[(pyrrolidin-3-ylmethyl)amino]phenyl}-1H-pyrrole-3-carboxamide;
2-methyl-5-{2-[(piperidin-4-ylmethyl)amino]phenyl}-1H-pyrrole-3-carboxamide;
tert-butyl 4-(2-{[2-(4-carbamoyl-5-methyl-1H-pyrrol-2-yl)phenyl]amino}ethyl)piperidine-1-carboxylate;
tert-butyl [cis-4-({[2-(4-carbamoyl-5-methyl-1H-pyrrol-2-yl)phenyl]amino}methyl)cyclohexyl]carbamate;
tert-butyl [trans-4-({[2-(4-carbamoyl-5-methyl-1H-pyrrol-2-yl)phenyl]amino}methyl)cyclohexyl]carbamate;
2-methyl-5-(2-{[2-(piperidin-4-yl)ethyl]amino}phenyl)-1H-pyrrole-3-carboxamide;
5-(2-{[(cis-4-aminocyclohexyl)methyl]amino}phenyl)-2-methyl-1H-pyrrole-3-carboxamide;
5-(2-{[(trans-4-aminocyclohexyl)methyl]amino}phenyl)-2-methyl-1H-pyrrole-3-carboxamide;
tert-butyl [4-({[2-(4-carbamoyl-5-methyl-1H-pyrrol-2-yl)phenyl]amino}methyl)phenyl]carbamate;
tert-butyl [3-({[2-(4-carbamoyl-5-methyl-1H-pyrrol-2-yl)phenyl]amino}methyl)phenyl]carbamate;
5-{2-[(4-aminobenzyl)amino]phenyl}-2-methyl-1H-pyrrole-3-carboxamide;
5-{2-[(3-aminobenzyl)amino]phenyl}-2-methyl-1H-pyrrole-3-carboxamide;
5-{2-[(4-hydroxybenzyl)amino]phenyl}-2-methyl-1H-pyrrole-3-carboxamide;
5-[2-({[5-(hydroxymethyl)furan-2-yl]methyl}amino)phenyl]-2-methyl-1H-pyrrole-3-carboxamide;
5-{2-[(1H-indol-5-ylmethyl)amino]phenyl}-2-methyl-1H-pyrrole-3-carboxamide;
5-{2-[(cyclopentylmethyl)(thiophen-2-ylmethyl)amino]phenyl}-2-methyl-1H-pyrrole-3-carboxamide;
5-{2-[(cyclopentylmethyl)(4-methoxybenzyl)amino]phenyl}-2-methyl-1H-pyrrole-3-carboxamide;
5-[2-(cyclohexylamino)phenyl]-2-methyl-1H-pyrrole-3-carboxamide;
2-methyl-5-[2-(tetrahydrofuran-3-ylamino)phenyl]-1H-pyrrole-3-carboxamide;
2-methyl-5-[2-(pyrrolidin-3-ylamino)phenyl]-1H-pyrrole-3-carboxamide;
2-methyl-5-[2-(piperidin-4-ylamino)phenyl]-1H-pyrrole-3-carboxamide;
5-[2-(cyclobutylamino)phenyl]-2-methyl-1H-pyrrole-3-carboxamide;
5-[2-(2,3-dihydro-1H-inden-1-ylamino)phenyl]-2-methyl-1H-pyrrole-3-carboxamide;
2-methyl-5-[2-(tetrahydro-2H-thiopyran-4-ylamino)phenyl]-1H-pyrrole-3-carboxamide;
5-[2-(2,3-dihydro-1H-inden-2-ylamino)phenyl]-2-methyl-1H-pyrrole-3-carboxamide;
2-methyl-5-[2-(tetrahydro-2H-pyran-4-ylamino)phenyl]-1H-pyrrole-3-carboxamide;
5-[2-(1-azabicyclo[2.2.2]oct-3-ylamino)phenyl]-2-methyl-1H-pyrrole-3-carboxamide;
2-methyl-5-{2-[tricyclo[3.3.1.1$^{3,7}$]dec-2-ylamino]phenyl}-1H-pyrrole-3-carboxamide;
5-[2-(cycloheptylamino)phenyl]-2-methyl-1H-pyrrole-3-carboxamide;
2-methyl-5-[2-(1,2,3,4-tetrahydronaphthalen-2-ylamino)phenyl]-1H-pyrrole-3-carboxamide;
5-{2-[(2-fluorocyclohexyl)amino]phenyl}-2-methyl-1H-pyrrole-3-carboxamide;
2-methyl-5-{2-[(phenylacetyl)amino]phenyl}-1H-pyrrole-3-carboxamide;
2-methyl-5-[2-(phenylamino)phenyl]-1H-pyrrole-3-carboxamide;
5-(2-{[(4-chlorophenyl)sulfonyl]amino}phenyl)-2-methyl-1H-pyrrole-3-carboxamide;
5-{2-[(cyclohexylsulfonyl)amino]phenyl}-2-methyl-1H-pyrrole-3-carboxamide;
2-methyl-5-{2-[(phenylsulfonyl)amino]phenyl}-1H-pyrrole-3-carboxamide;
2-methyl-5-{2-[(pyridin-3-ylsulfonyl)amino]phenyl}-1H-pyrrole-3-carboxamide;
2-methyl-5-(2-{[(3,3,3-trifluoropropyl)sulfonyl]amino}phenyl)-1H-pyrrole-3-carboxamide;
5-{2-[(benzylsulfonyl)amino]phenyl}-2-methyl-1H-pyrrole-3-carboxamide;
5-(2-{[(2,4-difluorophenyl)sulfonyl]amino}phenyl)-2-methyl-1H-pyrrole-3-carboxamide;
5-(2-{[(4-chlorobenzyl)sulfonyl]amino}phenyl)-2-methyl-1H-pyrrole-3-carboxamide;
2-methyl-5-(2-{[(2,2,2-trifluoroethyl)sulfonyl]amino}phenyl)-1H-pyrrole-3-carboxamide;
5-{2-[(cyclopentylsulfonyl)amino]phenyl}-2-methyl-1H-pyrrole-3-carboxamide;
5-(2-{[(4-hydroxyphenyl)sulfonyl]amino}phenyl)-2-methyl-1H-pyrrole-3-carboxamide;
2-methyl-5-(2-phenoxyphenyl)-1H-pyrrole-3-carboxamide;
5-(2,4-dimethylphenyl)-2-methyl-1H-pyrrole-3-carboxamide;
5-(2-amino-6-phenoxyphenyl)-2-methyl-1H-pyrrole-3-carboxamide;
5-[4-(3,5-dimethyl-1,2-oxazol-4-yl)phenyl]-2-methyl-1H-pyrrole-3-carboxamide;
methyl N-({5-[4-(3,5-dimethyl-1,2-oxazol-4-yl)phenyl]-2-methyl-1H-pyrrol-3-yl}carbonyl)-beta-alaninate;
methyl N-({5-[4-(3,5-dimethyl-1,2-oxazol-4-yl)phenyl]-2-methyl-1H-pyrrol-3-yl}carbonyl)glycinate;
5-[4-(3,5-dimethyl-1,2-oxazol-4-yl)phenyl]-N-hydroxy-2-methyl-1H-pyrrole-3-carboxamide;
2-methyl-5-{4'-[(4-methylpiperazin-1-yl)methyl]biphenyl-4-yl}-1H-pyrrole-3-carboxamide;
5-(3'-hydroxybiphenyl-4-yl)-2-methyl-1H-pyrrole-3-carboxamide;
2-methyl-5-(3',4',5'-trimethoxybiphenyl-4-yl)-1H-pyrrole-3-carboxamide;
5-[4-(furan-3-yl)phenyl]-2-methyl-1H-pyrrole-3-carboxamide;
2-methyl-5-[4-(thiophen-3-yl)phenyl]-1H-pyrrole-3-carboxamide;
2-methyl-5-[4-(pyridin-4-yl)phenyl]-1H-pyrrole-3-carboxamide;
2-methyl-5-[4-(1-methyl-1H-pyrazol-4-yl)phenyl]-1H-pyrrole-3-carboxamide;
5-[3'-(dimethylcarbamoyl)biphenyl-4-yl]-2-methyl-1H-pyrrole-3-carboxamide;
2-methyl-5-[3'-(morpholin-4-yl)biphenyl-4-yl]-1H-pyrrole-3-carboxamide;
5-{3'-[(furan-2-ylmethyl)carbamoyl]biphenyl-4-yl}-2-methyl-1H-pyrrole-3-carboxamide;
5-{4-[(1E)-3-methoxyprop-1-en-1-yl]phenyl}-2-methyl-1H-pyrrole-3-carboxamide;
5-[4'-(dimethylcarbamoyl)biphenyl-4-yl]-2-methyl-1H-pyrrole-3-carboxamide;
2-methyl-5-[4-(pyrimidin-5-yl)phenyl]-1H-pyrrole-3-carboxamide;
2-methyl-5-{4'-[(methylsulfonyl)amino]biphenyl-4-yl}-1H-pyrrole-3-carboxamide;
5-[4-(1-benzyl-1H-pyrazol-4-yl)phenyl]-2-methyl-1H-pyrrole-3-carboxamide;

5-[4-(3,5-dimethyl-1H-pyrazol-4-yl)phenyl]-2-methyl-1H-pyrrole-3-carboxamide;
2-methyl-5-[4-(quinolin-6-yl)phenyl]-1H-pyrrole-3-carboxamide;
2-methyl-5-{4'-[(4-methylpiperazin-1-yl)carbonyl]biphenyl-4-yl}-1H-pyrrole-3-carboxamide;
5-(2-bromophenyl)-2-methyl-1H-pyrrole-3-carboxamide;
5-[2-(4-chlorophenoxy)phenyl]-2-methyl-1H-pyrrole-3-carboxamide;
5-[2-(2-fluorophenoxy)phenyl]-2-methyl-1H-pyrrole-3-carboxamide;
5-[2-(1H-indol-6-yloxy)phenyl]-2-methyl-1H-pyrrole-3-carboxamide;
5-[2-(4-aminophenoxy)phenyl]-2-methyl-1H-pyrrole-3-carboxamide;
2-methyl-5-[2-(pyridin-4-yloxy)phenyl]-1H-pyrrole-3-carboxamide;
5-[2-(4-benzylphenoxy)phenyl]-2-methyl-1H-pyrrole-3-carboxamide;
2-methyl-5-[2-(4-phenoxyphenoxy)phenyl]-1H-pyrrole-3-carboxamide;
5-[2-(4-cyanophenoxy)phenyl]-2-methyl-1H-pyrrole-3-carboxamide;
5-[2-(4-cyclopentylphenoxy)phenyl]-2-methyl-1H-pyrrole-3-carboxamide;
5-[2-(isoquinolin-5-yloxy)phenyl]-2-methyl-1H-pyrrole-3-carboxamide;
2-methyl-5-[2-(pyridin-3-yloxy)phenyl]-1H-pyrrole-3-carboxamide;
5-[2-(3-cyanophenoxy)phenyl]-2-methyl-1H-pyrrole-3-carboxamide;
2-methyl-5-[2-(quinolin-5-yloxy)phenyl]-1H-pyrrole-3-carboxamide;
5-[2-(4-chloro-2-fluorophenoxy)phenyl]-2-methyl-1H-pyrrole-3-carboxamide;
5-[2-(1H-indol-5-yloxy)phenyl]-2-methyl-1H-pyrrole-3-carboxamide;
2-methyl-5-[2-(pyridin-2-yloxy)phenyl]-1H-pyrrole-3-carboxamide;
2-methyl-5-{2-[4-(methylsulfonyl)phenoxy]phenyl}-1H-pyrrole-3-carboxamide;
methyl 3-{2-[2-(4-carbamoyl-5-methyl-1H-pyrrol-2-yl)phenoxy]phenyl}propanoate;
2-methyl-5-[2-(3-methylphenoxy)phenyl]-1H-pyrrole-3-carboxamide;
5-{2-[4-(1H-imidazol-1-yl)phenoxy]phenyl}-2-methyl-1H-pyrrole-3-carboxamide;
2-methyl-5-[2-(5,6,7,8-tetrahydronaphthalen-1-yloxy)phenyl]-1H-pyrrole-3-carboxamide;
5-[2-(4-methoxyphenoxy)phenyl]-2-methyl-1H-pyrrole-3-carboxamide;
5-[2-(2-benzylphenoxy)phenyl]-2-methyl-1H-pyrrole-3-carboxamide;
2-methyl-5-[2-(naphthalen-2-yloxy)phenyl]-1H-pyrrole-3-carboxamide;
2-methyl-5-[2-(naphthalen-1-yloxy)phenyl]-1H-pyrrole-3-carboxamide;
5-[2-(4-fluorophenoxy)phenyl]-2-methyl-1H-pyrrole-3-carboxamide;
5-[2-(3-chlorophenoxy)phenyl]-2-methyl-1H-pyrrole-3-carboxamide;
5-[2-(4-ethylphenoxy)phenyl]-2-methyl-1H-pyrrole-3-carboxamide;
5-[2-(2,3-dihydro-1H-inden-5-yloxy)phenyl]-2-methyl-1H-pyrrole-3-carboxamide;
5-[2-(6-hydroxy-1H-benzimidazol-1-yl)phenyl]-2-methyl-1H-pyrrole-3-carboxamide;
5-[2-(5-hydroxy-1H-benzimidazol-1-yl)phenyl]-2-methyl-1H-pyrrole-3-carboxamide;
5-(2,6-difluorophenyl)-2-methyl-1H-pyrrole-3-carboxamide;
5-(2-benzylphenyl)-2-methyl-1H-pyrrole-3-carboxamide;
2-methyl-5-(3,4,5-trimethoxyphenyl)-1H-pyrrole-3-carboxamide;
5-(biphenyl-3-yl)-2-methyl-1H-pyrrole-3-carboxamide;
5-(3'-methoxybiphenyl-3-yl)-2-methyl-1H-pyrrole-3-carboxamide;
2-methyl-5-[3-(thiophen-3-yl)phenyl]-1H-pyrrole-3-carboxamide;
5-(2'-acetylbiphenyl-3-yl)-2-methyl-1H-pyrrole-3-carboxamide;
2-methyl-5-[3-(pyridin-3-yl)phenyl]-1H-pyrrole-3-carboxamide;
2-methyl-5-[3-(1H-pyrazol-4-yl)phenyl]-1H-pyrrole-3-carboxamide;
2-methyl-5-[3-(1-methyl-1H-indol-5-yl)phenyl]-1H-pyrrole-3-carboxamide;
2-methyl-5-{3-[(E)-2-phenylethenyl]phenyl}-1H-pyrrole-3-carboxamide;
2-methyl-5-{3'-[(4-methylpiperazin-1-yl)methyl]biphenyl-3-yl}-1H-pyrrole-3-carboxamide;
5-(4'-{[2-(dimethylamino)ethyl]carbamoyl}biphenyl-3-yl)-2-methyl-1H-pyrrole-3-carboxamide;
5-(5-amino-2-phenoxyphenyl)-2-methyl-1H-pyrrole-3-carboxamide;
2-methyl-5-{5-[(methylsulfonyl)amino]-2-phenoxyphenyl}-1H-pyrrole-3-carboxamide;
5-(1H-benzimidazol-4-yl)-2-methyl-1H-pyrrole-3-carboxamide;
5-(1H-indol-7-yl)-2-methyl-1H-pyrrole-3-carboxamide;
ethyl [4-(benzyloxy)-3-(4-carbamoyl-5-methyl-1H-pyrrol-2-yl)phenyl]acetate;
[4-(benzyloxy)-3-(4-carbamoyl-5-methyl-1H-pyrrol-2-yl)phenyl]acetic acid;
5-[2-(benzyloxy)-5-(2-hydroxyethyl)phenyl]-2-methyl-1H-pyrrole-3-carboxamide;
5-[2-(2,4-difluorophenoxy)-5-sulfamoylphenyl]-2-methyl-1H-pyrrole-3-carboxamide; and pharmaceutically acceptable salts thereof.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention provides for contraception in a male subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided. In certain embodiments, pharmaceutical compositions comprise a therapeutically effective amount of a compound of formula (I), or a pharmaceutically acceptable salt thereof, and a pharmaceutically acceptable carrier.

DETAILED DESCRIPTION

Disclosed herein are compounds of formula (I)

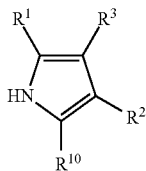

wherein $R^1$, $R^2$, and $R^{10}$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a). DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, six, or seven hydrogen atoms are replaced by halogen. The term "$C_1$-$C_3$ haloalkyl" means a $C_1$-$C_3$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, trifluoropropyl, 2,2,3,3,3-pentafluoropropyl, and 2,2,3,3,4,4,4-heptafluorobutyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl), of 1 to 4 carbon atoms, or of 2 to 3 carbon atoms ($C_2$-$C_3$ alkylenyl). Examples of alkylene and alkylenyl include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkenyl" as used herein, means a straight or branched hydrocarbon chain containing from 2 to 10 carbons and containing at least one carbon-carbon double bond, optionally substituted with 1, 2, or 3 halogen atoms. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH=CH— and —$CH_2$CH=CH—.

The term "aryl" as used herein, means phenyl or a bicyclic aryl. The bicyclic aryl is naphthyl, or a phenyl fused to a monocyclic $C_5$-$C_7$ cycloalkyl. Non-limiting examples of the aryl groups include dihydroindenyl (indanyl), indenyl, naphthyl, dihydronaphthalenyl, and tetrahydronaphthalenyl. The aryls are attached to the parent molecular moiety through any carbon atom contained within the bicyclic ring systems and can be unsubstituted or substituted.

The term "$C_3$-$C_{10}$ cycloalkyl" as used herein, refers to a radical that is a $C_3$ to $C_8$ monocyclic cyclic alkyl, or a $C_6$ to $C_{10}$ bicyclic cycloalkyl. A $C_3$ to $C_8$ monocyclic cycloalkyl is a carbocyclic ring system containing three to eight carbon atoms. Examples of monocyclic ring systems include cyclopropyl, cyclobutyl, cyclopentyl, cyclohexyl, cycloheptyl, and cyclooctyl. A bicyclic $C_6$ to $C_{10}$ cycloalkyl is a monocyclic $C_4$ to $C_6$ cycloalkyl fused to a monocyclic $C_4$ to $C_6$ cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of the $C_3$-$C_{10}$ cycloalkyl that contain such alkylene bridges include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bicyclic cycloalkyl groups can be attached to the parent molecular moiety through any substitutable atom contained within the ring system.

The term "halo" or "halogen" as used herein, means Cl, Br, I, and F.

The phrase "3- to 8-membered heterocycloalkyl" means a non-aromatic cyclic group having carbon atoms and 1 to 3 heteroatoms independently selected from S, N or O, wherein when two O atoms or one O atom and one S atom are present, the two O atoms or one O atom and one S atom are not bonded to each other, respectively. The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

A "4-membered heterocycloalkyl" is a 4-membered, monocyclic cycloalkyl ring having 3 carbon atoms and 1 heteroatom selected from the group consisting of: 1 O; 1 S; and 1 N. Illustrative examples of 4-membered heterocycloalkyls include oxetanyl, azetidinyl, and thietanyl.

A "5-membered heterocycloalkyl" is a 5-membered, monocyclic cycloalkyl ring having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

A "6-membered heterocycloalkyl" is a 6-membered, monocyclic cycloalkyl ring having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

A "7-membered heterocycloalkyl" is a 7-membered, monocyclic cycloalkyl ring having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1 O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

An "8-membered heterocycloalkyl" is a 8-membered, monocyclic cycloalkyl ring having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The monocyclic heterocycloalkyl groups may contain one or two alkylene bridges, each consisting of no more than four carbon atoms and each linking two non adjacent atoms of the ring system. Examples of such bridged heterocycloalkyls include, but are not limited to, azabicyclo[2.2.1]heptyl (including 2-azabicyclo[2.2.1]hept-2-yl), 8-azabicyclo[3.2.1]oct-8-yl, and 1-azabicyclo[2.2.2]oct-3-yl.

The term "heteroaryl" as used herein, unless otherwise denoted, means a monocyclic or 6 membered heteroaryl and a bicyclic 8 to 12 membered heteroaryl.

A "5-membered heteroaryl" is a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

A "6-membered heteroaryl" is a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

An "8- to 12-membered bicyclic heteroaryl" is a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a $C_5$-$C_8$ monocyclic cycloalkyl; (4) a 5- to 7-membered heterocycloalkyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention. Thus, the formula drawings within this specification may represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, can be prepared by methodologies known in the art, for example, through the reaction schemes depicted in schemes 1-5. The variables $R^1$, $R^2$, $R^8$, $R^9$, $R^{10}$, $R^{12}$, $R^{20}$, $R^{22}$, and the substituents of $R^{10}$, used in the following schemes have the meanings as set forth in the summary and detailed description sections, unless otherwise noted.

with ammonium acetate in acetic acid, in a solvent such as, but not limited to, ethanol and water, and at elevated temperatures (e.g. about 60° C. to about 100° C.). Hydrolysis of the ester moiety of (4) may be achieved by reaction with an acid, such as aqueous hydrochloric acid or trifluoroacetic acid, or may be achieved by reaction of (4) with a base such as lithium hydroxide or sodium hydroxide in a solvent such as, but not limited to tetrahydrofuran and water, to provide acid (5). Amides of formula I may be prepared from (5) by reaction with ammonium chloride or a substituted amine in the presence of a coupling agent such as HOBT, HATU or EDAC and a base such as diisopropylethylamine or triethylamine, and in a solvent such as tetrahydrofuran, dioxane, or dimethylformamide, at a temperature from about 0° C. to about 40° C.

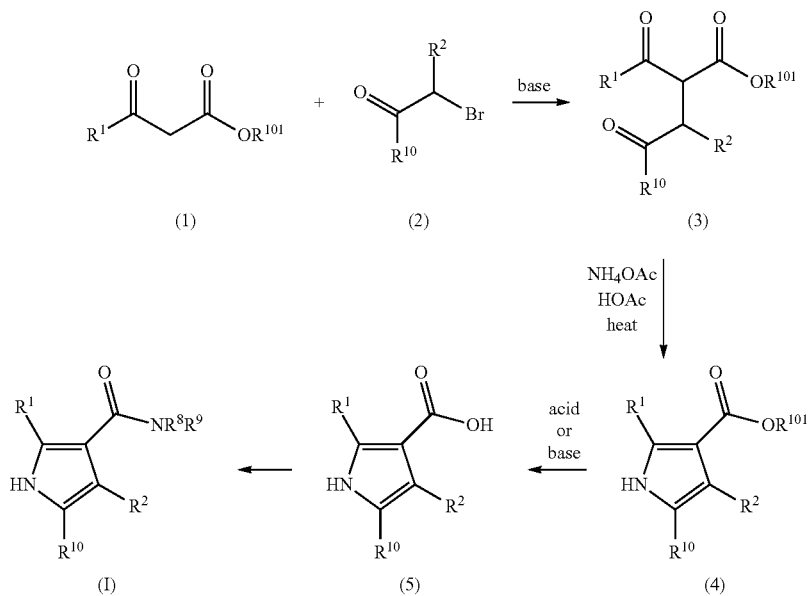

Scheme 1

Abbreviations used in the descriptions of the schemes and the specific examples have the following meanings: DMAP for 4-dimethylaminopyridine, DME for 1,2-dimethoxyethane, DMF for dimethylformamide, DMSO for dimethyl sulfoxide, EDAC or EDCI or EDC for 1-ethyl-3-[3-(dimethylamino)propyl]-carbodiimide hydrochloride, HATU for O-(7-azabenzotriazol-1-yl)-N,N,N',N'-tetramethyluronium hexafluorophosphate, HOBT for 1-hydroxybenzotriazole hydrate, HPLC for high performance liquid chromatography, $Pd_2(dba)_3$ for tris(dibenzylideneacetone)dipalladium (0), $PdCl_2(dppf)$ for [1,1'-bis(diphenylphosphino)ferrocene]dichloropalladium(II); SFC for Supercritical Fluid Chromatography, and TFA for trifluoroacetic acid, THF for tetrahydrofuran, and triflate for trifluoromethanesulfonate.

Compounds of general formula (I) may be prepared using the general procedure outlined in Scheme 1. Reaction of (1), wherein $R^{101}$ is methyl, ethyl, or tert-butyl, with compounds of formula (2) in the presence of a base, such as but not limited to, sodium hydride, in a solvent, such as tetrahydrofuran or diethyl ether, at temperature from about 0° C. to about 30° C., provides compounds of formula (3). Conversion of (3) to pyrrole (4) may be achieved by reaction of (3)

Alternatively, compounds of general formula (I) may be prepared using the general procedure as outlined in Scheme 2. Conversion of (6) to (7) wherein X is I or Br may be accomplished by reaction of (6) with N-iodosuccinamide or N-bromosuccinamide respectively in a solvent such as, but not limited to, tetrahydrofuran at temperatures ranging from about −78° C. to about 0° C. Conversion of (7), wherein X is Br or I, to compounds of general formula (I) may be achieved by reaction of (7) with a boronic acid of formula (8) or a derivative thereof (e.g. pinacol ester) under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (e.g. about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but are not limited to, carbonates or phosphates of sodium, potassium, and cesium, and cesium fluoride.

Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydrofuran, and water, or a mixture thereof.

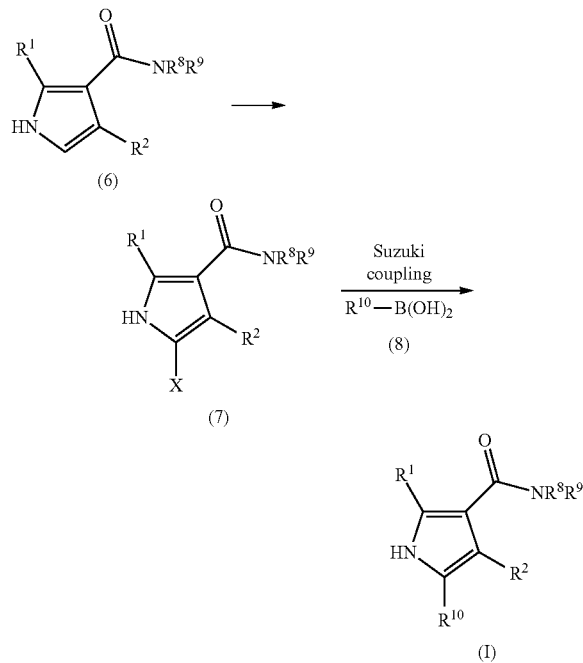

Compounds of general formula (I) wherein $R^{10}$ is a substituted phenyl wherein one of the substituents is $NR^{20}R^{22}$ or L-$R^{12}$ and L is —NH—, NHCO— or —NHSO$_2$—, may be prepared using synthetic routes such as, but not limited to, those illustrated in Scheme 3. Reduction of the nitro compounds of formula (9) to the anilines of formula (10) may be achieved with iron powder in the presence of ammonium chloride in a solvent such as, but not limited to, tetrahydrofuran, ethanol, or water, or a mixture thereof, and at a temperature from about 80° C. to about 120° C. Alternatively the reduction may be carried out with tin chloride in hydrochloric acid at a temperature from about 80° C. to about 120° C. Transformation of (9) to (10) may also be conducted in the presence of a catalyst such as platinum oxide or palladium on charcoal, in a solvent such as ethanol or methanol and under hydrogen pressure. Treatment of aniline (10) with carboxylic acids of formula $R^{12}$COOH in the presence of a coupling agent such as HATU or EDAC and a base such as diisopropylethylaminde or triethylamine, and in a solvent such as tetrahydrofuran, dioxane, or dimethylformamide, at a temperature from about 0° C. to about 40° C. provides amides of formula (11). Treatment of aniline (10) with sulfonyl chlorides of formula $R^{12}SO_2Cl$, in the presence of a base such as triethylamine or diisopropylethylamine in a solvent such as dichloromethane or tetrahydrofuran and at a temperature from about 0° C. to about 40° C. provides sulfonamides (12). Treatment of anilines (10) with a suitable aldehyde or ketone in the presence of a reducing agent such as, but not limited to, sodium triacetoxyborohydride, MP-cyanoborohydride (macroporous triethylammonium methylpolystyrene cyanoborohydride) resin, sodium cyanoborohydride or sodium borohydride and an acid, such as, but not limited to, acetic acid, in a solvent or combination of solvents such as but not limited to dichloromethane, methanol or ethanol provides anilines of formula (13). Compounds of formula (14) may be prepared by reaction of compounds of formula (10) with boronic acids of formula $R^{12}B(OH)_2$, or a derivative thereof (e.g. pinacol ester), in the presence of a catalyst such as, but not limited to, Cu(II)acetate and an acid, such as but not limited to myristic acid, and a base, such as but not limited to 2,6-lutidine, in a solvent such as, but not limited to, toluene provides compounds of formula (14).

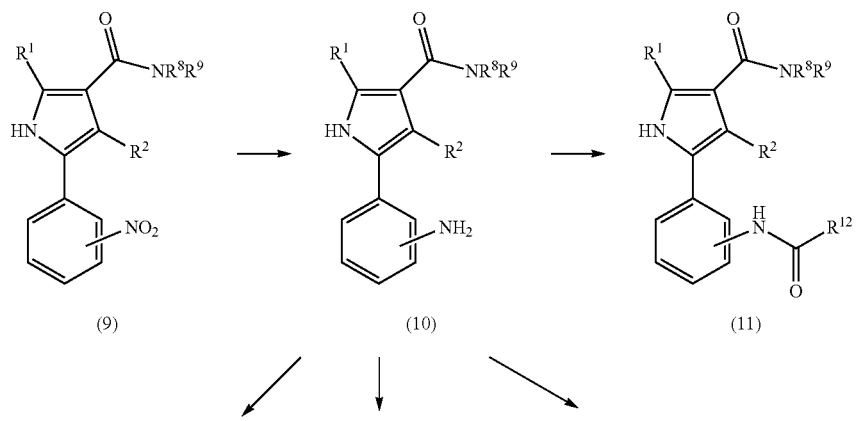

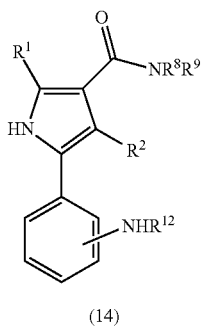

(14)

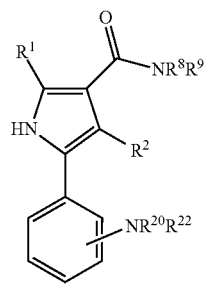

(13)

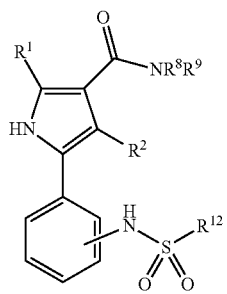

(12)

Compounds of general formula (I) wherein $R^{104}$ is aryl or heteroaryl may be prepared using synthetic routes such as, but not limited to, those illustrated in Scheme 4. Conversion of (15) wherein $R^{103}$ is the same as the group of substituents of $R^{10}$ (other than halogen) as defined in the Summary, m is 0, 1, or 2, and $R^{102}$ is Br, I, or triflate; to compounds of formula (17) may be achieved by reaction of (15) with a boronic acid of formula (16) or a derivative thereof (e.g. pinacol ester) under Suzuki coupling conditions described above.

Scheme 4

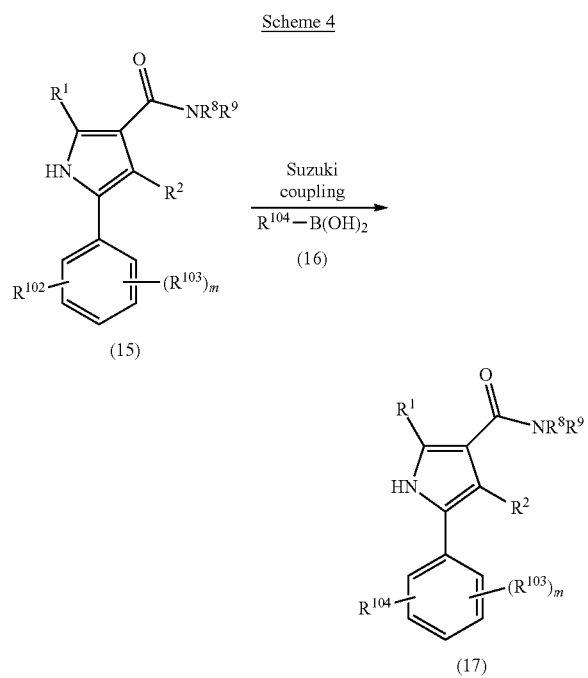

Target molecules such as (19), (20), and (21) where $R^{105}$ is the same as the group of substituents of $R^{10}$ (other than halogen) and n is 0, 1, or 2, may be prepared using the synthetic route such as, but not limited to, illustrated in Scheme 5. Displacement of the fluorine atom of (18) wherein $R^{106}$ is fluorine with an alcohol of formula $R^{12}$—OH may be accomplished in a solvent such as, but not limited to, dimethylsulfoxide, dimethylformamide, dioxane, or tetrahydrofuran and in the presence of a base such as, but not limited to, carbonate of cesium, potassium, or sodium, or sodium hydride, and at a temperature from about 40° C. to about 120° C. may provide compounds of formula (19). Alternatively, reaction of compounds of formula (18) wherein $R^{106}$ is Br, I, Cl, or triflate with an alcohol $R^{12}$OH wherein $R^{12}$ is aryl, heteroaryl, cycloalkyl, or heteroaryl as defined in the Summary, may provide compounds of formula (19). The conversion may be conducted in the presence of a catalyst such as, but not limited to, Cu(II)acetate, and an acid, such as but not limited to, picolinic acid, and a base, such as but not limited to potassium phosphate, in a solvent such as, but not limited to, dimethylsulfoxide or dimethylformamide, at temperatures ranging from about 70° C. to about 140° C. Reduction of compounds of formula (19) wherein n is 1 and $R^{105}$ is $NO_2$, to the anilines of formula (20) may be achieved with iron powder in the presence of ammonium chloride in a solvent such as, but not limited to, tetrahydrofuran, ethanol, or water, or a mixture thereof, and at a temperature from about 80° C. to about 120° C. Alternatively the reduction may be carried out with tin chloride in hydrochloric acid at a temperature from about 80° C. to about 120° C. The reduction may also be conducted in the presence of a catalyst such as platinum oxide or palladium on charcoal, in a solvent such as ethanol or methanol and under hydrogen pressure. Treatment of aniline (20) with sulfonyl chlorides of formula $R^{12}SO_2Cl$ in the presence of a base such as triethylamine or diisopropylethylamine in a solvent such as dichloromethane or tetrahydrofuran and at a temperature from about 0° C. to about 40° C. provides sulfonamides (21).

Scheme 5

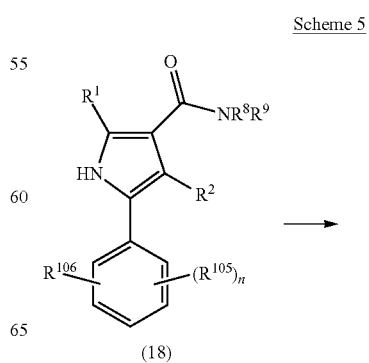

(18)

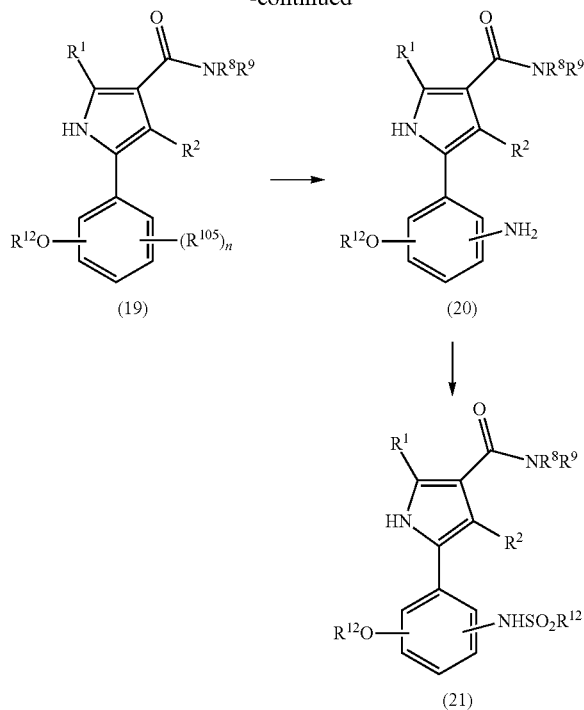

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((-)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1

5-(2-aminophenyl)-2-methyl-1H-pyrrole-3-carboxamide Example 1a tert-butyl 2-acetyl-4-(2-nitrophenyl)-4-oxobutanoate To a suspension of sodium hydride (60% dispersion in mineral oil, 2.95 g, 73.8 mmol) in anhydrous tetrahydrofuran (120 mL) under $N_2$ at 0° C. was added dropwise tert-butyl 3-oxobutanoate (10.12 mL, 61.5 mmol). The resulting mixture was stirred at 5° C. for 20 minutes, treated dropwise with a solution of 2-bromo-2'-nitroacetophenone (15 g, 61.5 mmol) in tetrahydrofuran (60 mL) and stirred at ambient temperature for 24 hours. The reaction mixture was then partitioned between ethyl acetate and saturated aqueous ammonium chloride solution, and the organic phase was washed with brine, dried (anhydrous $Na_2SO_4$), filtered and concentrated. The residue was purified by flash chromatography (silica gel, 5-45% ethyl acetate in hexanes) to provide the title compound (15.8 g, 80%).

Example 1b tert-butyl 2-methyl-5-(2-nitrophenyl)-1H-pyrrole-3-carboxylate

A mixture of Example 1a (15.8 g, 49.2 mmol) and ammonium acetate (37.9 g, 492 mmol) in acetic acid (50 mL) was heated at 80° C. for 1.5 hours, cooled and diluted with 200 mL of ice water producing a solid. The mixture was stirred for ten minutes and the solid was collected by filtration, washed repeatedly with water and dried to constant mass to give the title compound (14.3 g, 96%).

Example 1c 2-methyl-5-(2-nitrophenyl)-1H-pyrrole-3-carboxylic acid

To a solution of Example 1b (7.4 g, 24.1 mmol) in 1,4-dioxane (50 mL) was added a solution of 4 M HCl in dioxane (36 mL, 144 mmol). The resulting mixture was stirred at ambient temperature for 16 hours and concentrated. The residue was azeotroped 3×25 mL with toluene and dried to constant mass to provide the title compound (6.23 g, 100%).

Example 1d 2-methyl-5-(2-nitrophenyl)-1H-pyrrole-3-carboxamide

A mixture of Example 1c (3.0 g, 12.18 mmol), 1-hydroxybenzotriazole (2.8 g, 18.28 mmol), $N^1$-((ethylimino)methylene)-$N^3$,$N^3$-dimethylpropane-1,3-diamine hydrochloride (3.5 g, 18.28 mmol) and ammonium chloride (3.26 g, 60.9 mmol) were combined in dimethylformamide (40.6 mL), treated with N,N-diisopropylethylamine (12.77 mL, 9.45 mmol) and heated at 40° C. for 24 hours. The mixture was cooled and partitioned between ethyl acetate and water. The aqueous layer was extracted 2× with ethyl acetate. The combined ethyl acetate extracts (400 mL) were washed sequentially with 100 mL each of saturated aqueous sodium bicarbonate solution, water, 1 M hydrochloric acid solution, and brine, dried (anhydrous $Na_2SO_4$), filtered and concentrated. The residue was triturated in a minimal volume of dichloromethane and the resulting solid collected by filtration to provide the title compound (2.09 g, 70%).

Example 1e 5-(2-aminophenyl)-2-methyl-1H-pyrrole-3-carboxamide

A mixture of Example 1d (2.09 g, 8.52 mmol), iron (2.38 g, 42.6 mmol) and ammonium chloride (0.684 g, 12.78 mmol) in a solvent mixture of ethanol, tetrahydrofuran, water (21 mL, 21 mL, 7 mL) was heated at 95° C. with vigorous stirring for 1.5 hours. The reaction mixture was cooled and filtered through a tight plug of Celite rinsing repeatedly with ethanol and tetrahydrofuran. The filtrate was concentrated and the residue dissolved in ethyl acetate, washed with brine, dried (anhydrous $Na_2SO_4$) filtered and concentrated to provide the title compound (2.0 g, quantitative yield). $^1$H NMR (300 MHz, DMSO-$d_6$) δ 11.00 (s, 1H), 7.17 (dd, J=7.80, 1.36 Hz, 1H), 7.12 (s, 1H), 6.95 (m, 1H), 6.73 (dd, J=7.97, 1.19 Hz, 1H), 6.64 (d, J=2.71 Hz, 1H), 6.60 (td, J=7.38, 1.19 Hz, 1H), 6.51 (s, 1H), 5.00 (s, 2H), 2.43 (s, 3H). MS (ESI+) m/z 216.0 (M+H)$^+$.

Example 2

5-[2-(acetylamino)phenyl]-2-methyl-1H-pyrrole-3-carboxamide

Example 1e (0.022 g, 0.1 mmol) was treated with acetic anhydride (0.094 mL, 1.000 mmol) and stirred at ambient temperature for 5 hours. The reaction mixture was concentrated to half of the volume and then diluted with 2 mL of diethyl ether. The solid was collected by filtration and rinsed with additional diethyl ether. The solid was taken up in ethyl acetate, washed with saturated sodium bicarbonate solution (2×), water, and brine, dried (anhydrous $MgSO_4$), filtered, concentrated and dried in a vacuum oven at 80° C. to give the title compound (0.0188 g, 73%). $^1$H NMR (300 MHz, DMSO-$d_6$) δ 11.15 (s, 1H), 9.08 (s, 1H), 7.60 (d, J=6.74 Hz, 1H), 7.40 (m, 1H), 7.18 (m, 3H), 6.71 (d, J=2.78 Hz, 1H), 6.58 (s, 1H), 2.46 (s, 3H), 2.05 (s, 3H). MS (ESI+) m/z 257.9 (M+H)+.

Example 3

2-methyl-5-(3-nitrophenyl)-1H-pyrrole-3-carboxamide Example 3a ethyl 2-acetyl-4-(3-nitrophenyl)-4-oxobutanoate Example 3a was prepared according to the procedure used for the preparation of Example 1a, substituting ethyl 3-oxobutanoate for tert-butyl 3-oxobutanoate and 2-bromo-3'-nitroacetophenone for 2-bromo-2'-nitroacetophenone, to provide the title compound (0.594 g, 40%).

Example 3b ethyl 2-methyl-5-(3-nitrophenyl)-1H-pyrrole-3-carboxylate

Example 3b was prepared according to the procedure used for the preparation of Example 1b, substituting Example 3a for Example 1a, to provide the title compound (0.125 g, 96%).

Example 3c 2-methyl-5-(3-nitrophenyl)-1H-pyrrole-3-carboxylic acid

To Example 3b (0.130 g, 0.475 mmol) in tetrahydrofuran (2 mL) was added lithium hydroxide monohydrate (0.199 g, 4.75 mmol) and water (0.500 mL). The reaction mixture was heated overnight at 60° C., cooled to ambient temperature, acidified with 2 N aqueous hydrochloric acid solution and extracted with ethyl acetate. The organic layer was washed with brine, dried (anhydrous MgSO$_4$), filtered, concentrated and dried in a vacuum oven at 80° C. to give the title compound (0.117, 90%).

Example 3d 2-methyl-5-(3-nitrophenyl)-1H-pyrrole-3-carboxamide

Example 3c (3 g, 12.18 mmol), ammonium chloride (1.304 g, 24.37 mmol), (benzotriazol-1-yl-oxytripyrrolidinophosphonium hexafluorophosphate (9.51 g, 18.28 mmol), and 1-hydroxybenzotriazole (2.80 g, 18.28 mmol) were combined with dimethylformamide (48.7 mL), treated with N,N-diisopropylethylamine (8.51 mL, 48.7 mmol) and stirred at ambient temperature overnight. The reaction mixture was partitioned between ethyl acetate and water, and the organic phase was washed with 1 N HCl solution, water, saturated aqueous sodium bicarbonate solution, and brine, dried (anhydrous MgSO$_4$), filtered, and concentrated. The residue was triturated with methanol and the resulting solid was collected by filtration to give the title compound (1.5 g, 50%). $^1$H NMR (300 MHz, DMSO-d$_6$) δ 11.67 (s, 1H), 8.43 (t, J=2.03 Hz, 1H), 7.97 (m, 2H), 7.65 (t, J=7.97 Hz, 1H), 7.17 (s, 1H), 7.13 (d, J=2.71 Hz, 1H), 6.68 (s, 1H), 2.48 (s, 3H). MS (ESI+) m/z 246.1 (M+H)+.

Example 4

5-(3-aminophenyl)-2-methyl-1H-pyrrole-3-carboxamide

Example 4 was prepared according to the procedure used for the preparation of Example 1e, substituting Example 3d for Example 1d and purification by flash chromatography (silica gel, 0 to 14% methanol in dichloromethane), to provide the title compound (0.193, 90%). $^1$H NMR (300 MHz, DMSO-d$_6$) δ 11.13 (s, 1H), 7.11 (s, 1H), 6.99 (m, 1H), 6.73 (m, 2H), 6.70 (d, J=2.78 Hz, 1H), 6.54 (s, 1H), 6.39 (m, 1H), 5.01 (s, 2H), 2.43 (s, 3H). MS (ESI+) m/z 216.1 (M+H)+.

Example 5

5-[3-(acetylamino)phenyl]-2-methyl-1H-pyrrole-3-carboxamide

Example 5 was prepared according to the procedure used for the preparation of Example 2, substituting Example 4 for Example 1e, to provide the title compound (0.347 g, 98%). $^1$H NMR (300 MHz, DMSO-d$_6$) δ 11.28 (s, 1H), 9.90 (s, 1H), 7.83 (s, 1H), 7.27 (m, 3H), 7.20 (m, J=10.51 Hz, 1H), 6.78 (d, J=2.71 Hz, 1H), 6.56 (s, 1H), 2.45 (s, 3H), 2.05 (s, 3H). LCMS m/z 258.1 (M+H)+.

Example 6

2-methyl-5-{3-[(methylsulfonyl)amino]phenyl}-1H-pyrrole-3-carboxamide

Example 4 (0.022 g, 0.1 mmol) was dissolved in pyridine (1.0 mL), treated with methanesulfonyl chloride (0.016 mL, 0.200 mmol) and stirred at ambient temperature for 1 hour and 10 minutes. The reaction mixture was concentrated, taken up in ethyl acetate, washed with water and brine, dried (anhydrous MgSO$_4$), filtered and concentrated. The residue was purified by flash chromatography (silica gel, 2 to 20% methanol in dichloromethane) to give the title compound (0.02 g, 68%). $^1$H NMR (300 MHz, DMSO-d$_6$) δ 11.34 (s, 1H), 9.71 (s, 1H), 7.38 (m, 1H), 7.32 (m, 2H), 7.19 (s, 1H), 6.99 (m, 1H), 6.82 (d, J=2.78 Hz, 1H), 6.59 (s, 1H), 3.01 (s, 3H), 2.46 (s, 3H). MS (ESI+) m/z 294.0 (M+H)+.

Example 7

2-methyl-5-(4-nitrophenyl)-1H-pyrrole-3-carboxamide

Example 7a ethyl 2-acetyl-4-(4-nitrophenyl)-4-oxobutanoate

Example 7a was prepared according to the procedure used for the preparation of Example 1a, substituting ethyl 3-oxobutanoate for tert-butyl 3-oxobutanoate and 2-bromo- 4'-nitroacetophenone for 2-bromo-2'-nitroacetophenone, to provide the title compound (8.0 g, 83%).

Example 7b ethyl 2-methyl-5-(4-nitrophenyl)-1H-pyrrole-3-carboxylate

Example 7b was prepared according to the procedure used for the preparation of Example 1b, substituting Example 7a for Example 1a, to provide the title compound (7.3 g, 97%).

Example 7c 2-methyl-5-(4-nitrophenyl)-1H-pyrrole-3-carboxylic acid

Example 7c was prepared according to the procedure used for the preparation of Example 3c, substituting Example 7b for Example 3b, to provide the title compound (2.38 g, 88%).

Example 7d 2-methyl-5-(4-nitrophenyl)-1H-pyrrole-3-carboxamide

Example 7d was prepared according to the procedure used for the preparation of Example 3d, substituting Example 7c for Example 3c and purification by flash chromatography (silica gel, 0 to 25% methanol in dichloromethane), to provide the title compound (1.8 g, 76%). $^1$H NMR (300 MHz, DMSO-$d_6$) δ 11.72 (s, 1H), 8.24 (m, 2H), 7.77 (m, 2H), 7.22 (m, J=2.71 Hz, 2H), 6.73 (s, 1H), 2.49 (s, 3H). MS (ESI−) m/z 244.2 (M−H)$^-$.

Example 8

5-(4-aminophenyl)-2-methyl-1H-pyrrole-3-carboxamide

Example 8 was prepared according to the procedure used for the preparation of Example 1e, substituting Example 7d for Example 1d and purification by flash chromatography (silica gel, 1 to 14% methanol in dichloromethane), to provide the title compound (0.202, 47%). $^1$H NMR (300 MHz, DMSO-$d_6$) δ 10.93 (s, 1H), 7.24 (m, 2H), 6.98 (s, 1H), 6.56 (m, 3H), 6.49 (s, 1H), 5.03 (s, 2H), 2.42 (s, 3H). LCMS m/z 216.2 (M+H)$^+$.

Example 9

2-methyl-5-{4-[(methylsulfonyl)amino]phenyl}-1H-pyrrole-3-carboxamide

Example 9 was prepared according to the procedure used for the preparation of Example 6, substituting Example 8 for Example 4, to provide the title compound (0.0333 g, 57%). $^1$H NMR (300 MHz, DMSO-$d_6$) δ 11.23 (s, 1H), 9.65 (s, 1H), 7.51 (d, J=8.48 Hz, 2H), 7.19 (d, J=8.48 Hz, 2H), 7.08 (s, 1H), 6.80 (d, J=2.71 Hz, 1H), 6.57 (s, 1H), 2.98 (s, 3H), 2.45 (s, 3H). MS (ESI+) m/z 294.0 (M+H)$^+$.

Example 10

5-[4-(acetylamino)phenyl]-2-methyl-1H-pyrrole-3-carboxamide

Example 10 was prepared according to the procedure used for the preparation of Example 2, substituting Example 8 for Example 1e, to provide the title compound (0.032 g, 62%). $^1$H NMR (300 MHz, DMSO-$d_6$) δ 11.19 (s, 1H), 9.90 (s, 1H), 7.55 (m, 2H), 7.46 (m, 2H), 7.07 (s, 1H), 6.76 (d, J=2.71 Hz, 1H), 6.57 (s, 1H), 2.45 (s, 3H), 2.04 (s, 3H). MS (ESI+) m/z 258.1 (M+H)$^+$.

Example 11

5-{2-[(4-chlorobenzyl)amino]phenyl}-2-methyl-1H-pyrrole-3-carboxamide

Example 1e (0.022 g, 0.1 mmol) and 4-chlorobenzaldehyde (0.015 g, 0.110 mmol) were combined with dichloromethane (1.0 mL) and acetic acid (5.72 μL, 0.100 mmol), stirred for 20 minutes at ambient temperature and treated with sodium triacetoxyborohydride (0.032 g, 0.150 mmol). The reaction mixture was stirred at ambient temperature for 3 days, slowly basified with saturated aqueous sodium bicarbonate solution and then extracted with dichloromethane. The combined extracts were dried (anhydrous MgSO$_4$), filtered and concentrated. The residue was purified by flash chromatography (silica gel, 1 to 5% methanol in dichloromethane) to give the title compound (0.017 g, 50%). $^1$H NMR (300 MHz, DMSO-$d_6$) δ 11.09 (s, 1H), 7.40 (m, 4H), 7.16 (m, J=7.54, 1.59 Hz, 2H), 6.97 (td, J=7.74, 1.19 Hz, 1H), 6.72 (d, J=2.38 Hz, 1H), 6.61 (t, J=7.54 Hz, 2H), 6.42 (d, J=7.93 Hz, 1H), 5.74 (s, 1H), 4.37 (s, 2H), 2.45 (s, 3H). MS (ESI+) m/z 340.0 (M+H)$^+$.

Example 12

5-[2-(benzylamino)phenyl]-2-methyl-1H-pyrrole-3-carboxamide

A microwave vial was charged with stirbar, a solution of Example 1e (0.02 g, 0.093 mmol) in dichloromethane/methanol (1:1 v/v) (0.5 mL), a solution of benzaldehyde (0.0197 g, 0.186 mmol) in dichloromethane/methanol (1:1 v/v) (0.619 mL) and acetic acid (0.558 mmol, 0.032 mL). The vial was capped and placed in heater/shaker at 50° C. for 1 hour. The vial was uncapped and MP-cyanoborohydride (macroporous triethylammonium methylpolystyrene cyanoborohydride) resin (0.206 g, 2.25 mmol/g loading) was added. The vial was capped once more and placed in a heater/shaker at 60° C. overnight. Upon completion, the reaction mixture was filtered and the filtrate was concentrated to dryness and purified by reverse phase HPLC (C8(2), 5 μM 100 Å column, 10-100% acetonitrile and 0.1% TFA in water) to provide the title compound (0.019 g, 49%). $^1$H NMR (500 MHz, DMSO-$d_6$/D$_2$O) δ 11.09 (s, 1H), 7.37 (m, 2H), 7.31 (m, 2H), 7.23 (m, 1H), 7.16 (dd, J=7.63, 1.53 Hz, 1H), 6.98 (m, 1H), 6.73 (d, J=2.75 Hz, 1H), 6.61 (m, 1H), 6.49 (d, J=8.24 Hz, 1H), 4.38 (s, 2H), 2.45 (s, 3H). MS (ESI+) m/z 306.0 (M+H)$^+$.

Example 13

2-methyl-5-{2-[(tetrahydrofuran-2-ylmethyl)amino]phenyl}-1H-pyrrole-3-carboxamide To Example 1e (0.041 g, 0.19 mmol) dissolved in methanol/dichloromethane (1:1 mixture) (0.5 mL) was added sequentially tetrahydrofuran-2-carbaldehyde (0.038 g, 0.38 mmol) dissolved in methanol/dichloromethane (1:1 mixture) (0.96 mL), acetic acid (0.066 mL, 1.14 mmol) and MP-cyanoborohydride (macroporous triethylammonium methylpolystyrene cyanoborohydride) resin (0.425 g, 2.25 mmol/g loading). The resulting mixture was shaken at 60° C. overnight. The reaction was concentrated to dryness and purified by reverse phase HPLC (C8(2), 5 μM 100 Å column, 10-100% acetonitrile and 0.1% TFA in water) to provide the title compound (0.0027 g, 5%). $^1$H NMR (400 MHz, DMSO-$d_6$/$D_2O$) δ 7.14 (m, 2H), 6.69 (m, 2H), 6.63 (s, 1H), 4.91 (m, 2H), 4.06 (m, 1H), 3.63 (m, 2H), 2.44 (s, 3H), 1.97 (m, 1H), 1.80 (m, 4H), 1.62 (m, 1H). MS (ESI+) m/z 300 (M+H)$^+$.

Example 14

5-{2-[(cyclopentylmethyl)amino]phenyl}-2-methyl-1H-pyrrole-3-carboxamide

Example 14 was prepared according to the procedure used for the preparation of Example 13, substituting cyclopentanecarbaldehyde for tetrahydrofuran-2-carbaldehyde, to provide the title compound (0.0024 g, 4%). $^1$H NMR (400 MHz, DMSO-$d_6$/$D_2O$) δ 7.13 (m, 2H), 6.65 (m, 2H), 6.62 (s, 1H), 3.02 (d, J=7.78 Hz, 2H), 2.44 (s, 3H), 2.17 (m, 1H), 1.61 (m, 6H), 1.23 (m, 2H). MS (ESI+) m/z 298 (M+H)$^+$.

Example 15

5-(2-{[(4-bromothiophen-2-yl)methyl]amino}phenyl)-2-methyl-1H-pyrrole-3-carboxamide Example 15 was prepared according to the procedure used for the preparation of Example 13, substituting 4-bromothiophene-2-carbaldehyde for tetrahydrofuran-2-carbaldehyde, to provide the title compound (0.0275 g, 37%). $^1$H NMR (400 MHz, DMSO-$d_6$/$D_2O$) δ 7.44 (d, J=1.53 Hz, 1H), 7.18 (dd, J=7.63, 1.53 Hz, 1H), 7.05 (m, 2H), 6.67 (m, 3H), 4.55 (s, 2H), 2.45 (s, 3H). MS (ESI+) m/z 392 (M+H)$^+$.

Example 16

2-methyl-5-{2-[(3,4,5-trimethoxybenzyl)amino]phenyl}-1H-pyrrole-3-carboxamide

Example 16 was prepared according to the procedure used for the preparation of Example 13, substituting 3,4,5-trimethoxybenzaldehyde for tetrahydrofuran-2-carbaldehyde, to provide the title compound (0.0079 g, 10%). $^1$H NMR (400 MHz, DMSO-$d_6$/$D_2O$) δ 7.17 (dd, J=7.63, 1.53 Hz, 1H), 7.04 (m, 1H), 6.73 (s, 1H), 6.68 (s, 2H), 6.63 (m, 2H), 4.29 (s, 2H), 3.72 (s, 6H), 3.62 (s, 3H), 2.45 (s, 3H). MS (ESI+) m/z 396 (M+H)$^+$.

Example 17

2-methyl-5-{2-[(tetrahydrofuran-3-ylmethyl)amino]phenyl}-1H-pyrrole-3-carboxamide Example 17 was prepared according to the procedure used for the preparation of Example 13, substituting tetrahydrofuran-3-carbaldehyde for tetrahydrofuran-2-carbaldehyde, to provide the title compound (0.0095 g, 17%). $^1$H NMR (400 MHz, DMSO-$d_6$/$D_2O$) δ 7.13 (m, 2H), 6.70 (m, 2H), 6.61 (s, 1H), 3.77 (m, 2H), 3.63 (q, J=7.83 Hz, 1H), 3.49 (dd, J=8.54, 5.19 Hz, 1H), 3.09 (dd, J=7.02, 3.66 Hz, 2H), 2.58 (m, 1H), 2.44 (s, 3H), 1.99 (m, 1H), 1.62 (m, 1H). MS (ESI+) m/z 300 (M+H)$^+$.

Example 18

2-methyl-5-(2-{[(3R)-tetrahydrofuran-3-ylmethyl]amino}phenyl)-1H-pyrrole-3-carboxamide The product from Example 17 was chromatographed (SFC $CO_2$, Chiralpak AD-H column, 10% to 50% isopropyl alcohol and 0.1% diethylamine buffer, elution time=4.44 minutes) to afford the title compound with arbitrary stereoassigment (0.046 g, 38%). $^1$H NMR (300 MHz, DMSO-$d_6$) δ 11.05 (s, 1H) 7.05-7.19 (m, 3H) 6.54-6.72 (m, 4H) 4.98 (t, J=5.75 Hz, 1H) 3.68-3.81 (m, 2H) 3.62 (q, J=7.80 Hz, 1H) 3.49 (dd, J=8.53, 5.35 Hz, 1H) 3.05-3.12 (m, 2H) 2.56 (d, J=6.35 Hz, 1H) 2.43 (s, 3H) 1.90-2.04 (m, 1H) 1.53-1.68 (m, 1H). MS (ESI–) m/z 298 (M–H)$^+$.

Example 19

2-methyl-5-(2-{[(3S)-tetrahydrofuran-3-ylmethyl]amino}phenyl)-1H-pyrrole-3-carboxamide The product from Example 17 was chromatographed (SFC $CO_2$, Chiralpak AD-H column, 10% to 50% isopropyl alcohol and 0.1% diethylamine buffer, elution time=4.64 minutes) to afford the title compound with arbitrary stereoassigment (0.036 g, 30%). $^1$H NMR (300 MHz, DMSO-$d_6$) δ 11.05 (s, 1H) 7.05-7.19 (m, 3H) 6.54-6.72 (m, 4H) 4.98 (t, J=5.75 Hz, 1H) 3.68-3.81 (m, 2H) 3.62 (q, J=7.80 Hz, 1H) 3.49 (dd, J=8.53, 5.35 Hz, 1H) 3.05-3.12 (m, 2H) 2.56 (d, J=6.35 Hz, 1H) 2.43 (s, 3H) 1.90-2.04 (m, 1H) 1.53-1.68 (m, 1H). MS (ESI–) m/z 298 (M–H)$^+$.

Example 20

5-(2-{[(4,5-dimethylfuran-2-yl)methyl]amino}phenyl)-2-methyl-1H-pyrrole-3-carboxamide Example 20 was prepared according to the procedure used for the preparation of Example 13, substituting 4,5-dimethylfuran-2-carbaldehyde for tetrahydrofuran-2-carbaldehyde, to provide the title compound (0.0033 g, 5%). $^1$H NMR (400 MHz, DMSO-$d_6$/$D_2O$) δ 7.16 (dd, J=7.63, 1.53 Hz, 1H), 7.08 (m, 1H), 6.74 (d, J=8.24 Hz, 1H), 6.68 (t, J=7.48 Hz, 1H), 6.64 (s, 1H), 6.04 (s, 1H), 4.25 (s, 2H), 2.44 (s, 3H), 2.11 (s, 3H), 1.83 (s, 3H). MS (ESI+) m/z 324 (M+H)$^+$.

Example 21

5-(2-{[3,5-bis(trifluoromethyl)benzyl]amino}phenyl)-2-methyl-1H-pyrrole-3-carboxamide Example 21 was prepared according to the procedure used for the preparation of Example 13, substituting 3,5-bis(trifluoromethyl)benzaldehyde for tetrahydrofuran-2-carbaldehyde, to provide the title compound (0.0378 g, 45%). $^1$H NMR (400 MHz, DMSO-$d_6$/$D_2O$) δ 8.05 (s, 2H), 7.95 (s, 1H), 7.20 (dd, J=7.63, 1.53 Hz, 1H), 7.00 (m, 1H), 6.76 (s, 1H), 6.68 (td, J=7.48, 0.92 Hz, 1H), 6.46 (d, J=7.93 Hz, 1H), 4.58 (s, 2H), 2.47 (s, 3H). MS (ESI+) m/z 442 (M+H)$^+$.

Example 22

5-{2-[(2,6-difluorobenzyl)amino]phenyl}-2-methyl-1H-pyrrole-3-carboxamide

Example 22 was prepared according to the procedure used for the preparation of Example 13, substituting 2,6-difluorobenzaldehyde for tetrahydrofuran-2-carbaldehyde, to provide the title compound (0.013 g, 20%). $^1$H NMR (400 MHz, DMSO-$d_6$/$D_2O$) δ 7.35 (m, 1H), 7.15 (dd, J=7.63, 1.53 Hz, 1H), 7.07 (m, 3H), 6.78 (d, J=7.93 Hz, 1H), 6.68 (t, J=7.02 Hz, 1H), 6.62 (s, 1H), 4.46 (s, 2H), 2.43 (s, 3H). MS (ESI+) m/z 342 (M+H)$^+$.

Example 23

5-{2-[(4-fluorobenzyl)amino]phenyl}-2-methyl-1H-pyrrole-3-carboxamide

Example 23 was prepared according to the procedure used for the preparation of Example 13, substituting 4-fluorobenzaldehyde for tetrahydrofuran-2-carbaldehyde, to provide the title compound (0.0076 g, 12%). $^1$H NMR (400 MHz, DMSO-$d_6$/$D_2O$) δ 7.41 (dd, J=8.54, 5.49 Hz, 2H), 7.15 (m, 3H), 6.98 (m, 1H), 6.73 (s, 1H), 6.63 (t, J=7.48 Hz, 1H), 6.48 (d, J=7.32 Hz, 1H), 4.36 (s, 2H), 2.46 (s, 3H). MS (ESI+) m/z 324 (M+H)$^+$.

Example 24

2-methyl-5-{2-[(2-methylbenzyl)amino]phenyl}-1H-pyrrole-3-carboxamide

Example 24 was prepared according to the procedure used for the preparation of Example 13, substituting 2-methylbenzaldehyde for tetrahydrofuran-2-carbaldehyde, to provide the title compound (0.0048 g, 8%). $^1$H NMR (400 MHz, DMSO-$d_6$/$D_2O$) δ 7.17 (m, 5H), 7.02 (m, 1H), 6.71 (s, 1H), 6.65 (t, J=7.48 Hz, 1H), 6.46 (d, J=7.63 Hz, 1H), 4.33 (s, 2H), 2.46 (m, 3H), 2.31 (s, 3H). MS (ESI+) m/z 320 (M+H)$^+$.

Example 25

2-methyl-5-{2-[(3-methylbenzyl)amino]phenyl}-1H-pyrrole-3-carboxamide

Example 25 was prepared according to the procedure used for the preparation of Example 13, substituting 3-methylbenzaldehyde for tetrahydrofuran-2-carbaldehyde, to provide the title compound (0.005 g, 8%). $^1$H NMR (400 MHz, DMSO-$d_6$/$D_2O$) δ 7.18 (m, 4H), 7.01 (m, 2H), 6.73 (s, 1H), 6.63 (t, J=7.02 Hz, 1H), 6.51 (d, J=7.93 Hz, 1H), 4.34 (s, 2H), 2.45 (s, 3H), 2.28 (s, 3H). MS (ESI+) m/z 320 (M+H)$^+$.

Example 26

5-{2-[(cyclopropylmethyl)amino]phenyl}-2-methyl-1H-pyrrole-3-carboxamide

Example 26 was prepared according to the procedure used for the preparation of Example 13, substituting cyclopropanecarbaldehyde for tetrahydrofuran-2-carbaldehyde, to provide the title compound (0.005 g, 10%). $^1$H NMR (400 MHz, DMSO-$d_6$/$D_2O$) δ 7.12 (m, 2H), 6.68 (dd, J=10.38, 7.93 Hz, 2H), 6.64 (s, 1H), 2.98 (d, J=6.71 Hz, 2H), 2.45 (s, 3H), 1.09 (m, 1H), 0.45 (m, 2H), 0.22 (m, 2H). MS (ESI+) m/z 270 (M+H)$^+$.

Example 27

5-[2-(butylamino)phenyl]-2-methyl-1H-pyrrole-3-carboxamide

Example 27 was prepared according to the procedure used for the preparation of Example 13, substituting butyralde-hyde for tetrahydrofuran-2-carbaldehyde, to provide the title compound (0.0057 g, 11%). $^1$H NMR (400 MHz, DMSO-$d_6$/$D_2O$) δ 7.14 (m, 2H), 6.66 (dd, J=7.63, 3.97 Hz, 2H), 6.62 (s, 1H), 3.09 (m, 2H), 2.44 (m, 3H), 1.53 (m, 2H), 1.34 (m, 2H), 0.92 (m, 3H). MS (ESI+) m/z 272 (M+H)$^+$.

Example 28

2-methyl-5-(2-{[4-(trifluoromethyl)benzyl]amino}phenyl)-1H-pyrrole-3-carboxamide Example 28 was prepared according to the procedure used for the preparation of Example 13, substituting 4-(trifluoromethyl)benzaldehyde for tetrahydrofuran-2-carbaldehyde, to provide the title compound (0.0194 g, 27%). $^1$H NMR (400 MHz, DMSO-$d_6$/$D_2O$) δ 7.68 (m, 2H), 7.60 (m, 2H), 7.18 (dd, J=7.63, 1.53 Hz, 1H), 6.98 (m, 1H), 6.76 (s, 1H), 6.64 (t, J=7.48 Hz, 1H), 6.43 (d, J=7.63 Hz, 1H), 4.48 (s, 2H), 2.47 (s, 3H). MS (ESI+) m/z 274 (M+H)$^+$.

Example 29

2-methyl-5-{2-[(4-methylbenzyl)amino]phenyl}-1H-pyrrole-3-carboxamide

Example 29 was prepared according to the procedure used for the preparation of Example 13, substituting 4-methylbenzaldehyde for tetrahydrofuran-2-carbaldehyde, to provide the title compound (0.0029 g, 5%). $^1$H NMR (400 MHz, DMSO-$d_6$/$D_2O$) δ 7.25 (d, J=7.93 Hz, 2H), 7.14 (m, 3H), 6.99 (m, 1H), 6.72 (s, 1H), 6.62 (m, 1H), 6.50 (d, J=7.63 Hz, 1H), 4.33 (s, 2H), 2.45 (s, 3H), 2.26 (s, 3H). MS (ESI+) m/z 320 (M+H)$^+$.

Example 30

5-{2-[(4-methoxybenzyl)amino]phenyl}-2-methyl-1H-pyrrole-3-carboxamide

Example 30 was prepared according to the procedure used for the preparation of Example 13, substituting 4-methoxybenzaldehyde for tetrahydrofuran-2-carbaldehyde, to provide the title compound (0.0021 g, 3%). $^1$H NMR (400 MHz, DMSO-$d_6$/$D_2O$) δ 7.29 (d, J=8.85 Hz, 2H), 7.15 (dd, J=7.63, 1.53 Hz, 1H), 7.00 (m, 1H), 6.88 (m, 2H), 6.71 (s, 1H), 6.62 (t, J=7.48 Hz, 1H), 6.53 (d, J=8.24 Hz, 1H), 4.30 (s, 2H), 3.72 (s, 3H), 2.45 (s, 3H). MS (ESI+) m/z 336 (M+H)$^+$.

Example 31

5-{2-[(4-cyanobenzyl)amino]phenyl}-2-methyl-1H-pyrrole-3-carboxamide

Example 31 was prepared according to the procedure used for the preparation of Example 13, substituting 4-formylbenzonitrile for tetrahydrofuran-2-carbaldehyde, to provide the title compound (0.0058 g, 9%). $^1$H NMR (400 MHz, DMSO-$d_6$/$D_2O$) δ 7.77 (d, J=8.24 Hz, 2H), 7.57 (d, J=8.54 Hz, 2H), 7.18 (dd, J=7.63, 1.53 Hz, 1H), 6.97 (m, 1H), 6.76 (s, 1H), 6.64 (t, J=7.48 Hz, 1H), 6.39 (d, J=7.63 Hz, 1H), 4.48 (s, 2H), 2.47 (s, 3H). MS (ESI+) m/z 331 (M+H)$^+$.

Example 32

5-{2-[(4-bromobenzyl)amino]phenyl}-2-methyl-1H-pyrrole-3-carboxamide

Example 32 was prepared according to the procedure used for the preparation of Example 13, substituting 4-bromobenzaldehyde for tetrahydrofuran-2-carbaldehyde, to provide the title compound (0.0173 g, 24%). $^1$H NMR (400 MHz, DMSO-$d_6$/$D_2O$) δ 7.50 (d, J=8.24 Hz, 2H), 7.34 (d, J=8.24 Hz, 2H), 7.17 (dd, J=7.63, 1.53 Hz, 1H), 6.99 (m, 1H), 6.74 (s, 1H), 6.63 (t, J=7.02 Hz, 1H), 6.44 (d, J=7.93 Hz, 1H), 4.35 (s, 2H), 2.46 (s, 3H). MS (ESI+) m/z 384 (M+H)$^+$.

Example 33

5-{2-[(3,4-dichlorobenzyl)amino]phenyl}-2-methyl-1H-pyrrole-3-carboxamide

Example 33 was prepared according to the procedure used for the preparation of Example 13, substituting 3,4-dichlorobenzaldehyde for tetrahydrofuran-2-carbaldehyde, to provide the title compound (0.0017 g, 2%). $^1$H NMR (400 MHz, DMSO-$d_6$/$D_2O$) δ 7.58 (m, 2H), 7.37 (dd, J=8.24, 1.83 Hz, 1H), 7.18 (dd, J=7.63, 1.53 Hz, 1H), 7.00 (m, 1H), 6.75 (s, 1H), 6.65 (t, J=7.48 Hz, 1H), 6.42 (d, J=7.63 Hz, 1H), 4.39 (s, 2H), 2.46 (s, 3H). MS (ESI+) m/z 374 (M+H)$^+$.

Example 34

5-{2-[(2-chlorobenzyl)amino]phenyl}-2-methyl-1H-pyrrole-3-carboxamide

Example 34 was prepared according to the procedure used for the preparation of Example 13, substituting 2-chlorobenzaldehyde for tetrahydrofuran-2-carbaldehyde, to provide the title compound (0.0169 g, 26%). $^1$H NMR (400 MHz, DMSO-$d_6$/$D_2O$) δ 7.46 (m, 1H), 7.38 (m, 1H), 7.29 (m, 2H), 7.19 (dd, J=7.32, 1.53 Hz, 1H), 7.02 (m, 1H), 6.75 (s, 1H), 6.66 (t, J=7.02 Hz, 1H), 6.38 (d, J=7.63 Hz, 1H), 4.45 (s, 2H), 2.46 (s, 3H). MS (ESI+) m/z 340 (M+H)$^+$.

Example 35

5-{2-[(3-chlorobenzyl)amino]phenyl}-2-methyl-1H-pyrrole-3-carboxamide

Example 35 was prepared according to the procedure used for the preparation of Example 13, substituting 3-chlorobenzaldehyde for tetrahydrofuran-2-carbaldehyde, to provide the title compound (0.0255 g, 39%). $^1$H NMR (400 MHz, DMSO-$d_6$/$D_2O$) δ 7.40 (s, 1H), 7.35 (m, 2H), 7.28 (m, 1H), 7.18 (dd, J=7.63, 1.53 Hz, 1H), 7.00 (m, 1H), 6.75 (s, 1H), 6.64 (t, J=7.02 Hz, 1H), 6.45 (d, J=7.63 Hz, 1H), 4.40 (s, 2H), 2.47 (s, 3H). MS (ESI+) m/z 340 (M+H)$^+$.

Example 36

5-{2-[(cyclohexylmethyl)amino]phenyl}-2-methyl-1H-pyrrole-3-carboxamide

Example 36 was prepared according to the procedure used for the preparation of Example 13, substituting cyclohexanecarbaldehyde for tetrahydrofuran-2-carbaldehyde, to provide the title compound (0.0043 g, 7%). $^1$H NMR (400 MHz, DMSO-$d_6$/$D_2O$) δ 7.09 (m, 2H), 6.63 (m, 3H), 2.96 (d, J=6.71 Hz, 2H), 2.44 (s, 3H), 1.64 (m, 6H), 1.15 (m, 3H), 0.89 (m, 2H). MS (ESI+) m/z 312 (M+H)$^+$.

Example 37

5-(2-{[4-(dimethylamino)benzyl]amino}phenyl)-2-methyl-1H-pyrrole-3-carboxamide

Example 37 was prepared according to the procedure used for the preparation of Example 13, substituting 4-(dimethylamino)benzaldehyde for tetrahydrofuran-2-carbaldehyde, to provide the title compound (0.0036 g, 5%). $^1$H NMR (400 MHz, DMSO-$d_6$/$D_2O$) δ 7.06 (m, 1H), 6.94 (dd, J=7.63, 1.53 Hz, 1H), 6.82 (d, J=8.85 Hz, 2H), 6.74 (d, J=7.93 Hz, 1H), 6.60 (m, 1H), 6.55 (d, J=8.85 Hz, 2H) 3.73 (m, 2H), 2.78 (m, 6H), 2.34 (s, 3H). MS (ESI+) m/z 349 (M+H)$^+$.

Example 38

2-methyl-5-{2-[(thiophen-2-ylmethyl)amino]phenyl}-1H-pyrrole-3-carboxamide

Example 38 was prepared according to the procedure used for the preparation of Example 13, substituting thiophene-2-carbaldehyde for tetrahydrofuran-2-carbaldehyde, to provide the title compound (0.005 g, 8%). $^1$H NMR (400 MHz, DMSO-$d_6$/$D_2O$) δ 7.33 (dd, J=5.19, 1.22 Hz, 1H), 7.17 (dd, J=7.63, 1.53 Hz, 1H), 7.06 (m, 2H), 6.96 (dd, J=5.19, 3.36 Hz, 1H), 6.69 (m, 3H), 4.56 (s, 2H), 2.44 (s, 3H). MS (ESI+) m/z 312 (M+H)$^+$.

Example 39

5-{2-[(3,5-dichlorobenzyl)amino]phenyl}-2-methyl-1H-pyrrole-3-carboxamide

Example 39 was prepared according to the procedure used for the preparation of Example 13, substituting 3,5-dichlorobenzaldehyde for tetrahydrofuran-2-carbaldehyde, to provide the title compound (0.0069 g, 10%). $^1$H NMR (400 MHz, DMSO-$d_6$/$D_2O$) δ 7.42 (m, 3H), 7.19 (dd, J=7.63, 1.53 Hz, 1H), 7.03 (m, 1H), 6.75 (s, 1H), 6.66 (t, J=7.48 Hz, 1H), 6.42 (d, J=7.63 Hz, 1H), 4.40 (s, 2H), 2.47 (s, 3H). MS (ESI+) m/z 374 (M+H)$^+$.

Example 40 tert-butyl 3-({[2-(4-carbamoyl-5-methyl-1H-pyrrol-2-yl)phenyl]amino}methyl)pyrrolidine-1-carboxylate Example 1e (86 mg, 0.40 mmol), tert-butyl 3-formylpyrrolidine-1-carboxylate (88 mg, 0.44 mmol), sodium triacetoxyhydroborate (136 mg, 0.64 mmol) and acetic acid (0.023 mL, 0.40 mmol) were combined in dichloromethane (2 mL). The reaction mixture was stirred at ambient temperature for 1 hour, diluted with dichloromethane, washed with saturated sodium bicarbonate solution and brine. The organic layer was dried with anhydrous sodium sulfate, filtered and concentrated. The residue was purified by flash chromatography (silica gel, 2-4% methanol in dichloromethane) to afford the title compound (124 mg, 78%). $^1$H NMR (300 MHz, DMSO-$d_6$) δ 11.05 (s, 1H) 7.01-7.23 (m, 3H) 6.49-6.74 (m, 4H) 4.97 (s, br, 1H) 3.33-3.45 (m, 2H) 3.16-3.25 (m, 1H) 3.07-3.16 (m, 2H) 2.91-3.02 (m, 1H) 2.43 (s, 3H) 1.87-1.97 (m, 1H) 1.52-1.67 (m, 1H) 1.31-1.42 (m, 10H). MS (ESI+) m/z 399 (M+H)$^+$.

Example 41 tert-butyl 4-({[2-(4-carbamoyl-5-methyl-1H-pyrrol-2-yl)phenyl]amino}methyl)piperidine-1-carboxylate Example 41 was prepared according to the procedure used for the preparation of Example 40, substituting tert-butyl 4-formylpiperidine-1-carboxylate for tert-butyl 3-formylpyrrolidine-1-carboxylate, to provide the title compound (128 mg, 78%). ¹H NMR (300 MHz, DMSO-d₆) δ 11.04 (s, 1H) 7.00-7.22 (m, 3H) 6.53-6.70 (m, 4H) 4.97 (t, J=5.95 Hz, 1H) 3.94 (d, J=13.09 Hz, 2H) 3.01 (t, J=6.35 Hz, 2H) 2.59-2.73 (m, 2H) 2.43 (s, 3H) 1.63-1.83 (m, 3H) 1.38 (s, 9H) 0.93-1.10 (m, 2H). MS (ESI+) m/z 413 (M+H)⁺.

Example 42

2-methyl-5-{2-[(pyrrolidin-3-ylmethyl)amino]phenyl}-1H-pyrrole-3-carboxamide

To the product from Example 40 (119 mg, 0.299 mmol) in dioxane (2 mL) was added 4.0 M hydrogen chloride in dioxane (2 mL, 8 mmol) and the reaction mixture was stirred at ambient temperature for 30 minutes. The reaction mixture was concentrated and azeotroped with dioxane. The residue was triturated with dichloromethane to afford the title compound (99 mg, 89%) as a hydrochloric acid salt. ¹H NMR (300 MHz, DMSO-d₆) δ 11.11 (s, 1H) 9.17 (s, 1H) 9.03 (s, 1H) 7.04-7.30 (m, 2H) 6.56-6.84 (m, 3H) 3.05-3.31 (m, 5H) 2.88-3.03 (m, 1H) 2.58-2.67 (m, 1H) 2.44 (s, 3H) 1.94-2.10 (m, 1H) 1.53-1.75 (m, 1H). MS (ESI+) m/z 299 (M+H)⁺.

Example 43

2-methyl-5-{2-[(piperidin-4-ylmethyl)amino]phenyl}-1H-pyrrole-3-carboxamide

Example 43 was prepared according to the procedure used for the preparation of Example 42, substituting the product from Example 41 for the product from Example 40, to provide the title compound (89 mg, 77%) as a hydrochloric acid salt. ¹H NMR (300 MHz, DMSO-d₆) δ 11.11 (s, 1H) 8.71-8.88 (m, 1H) 8.43-8.69 (m, 1H) 7.04-7.21 (m, 2H) 6.54-6.77 (m, 3H) 3.25 (d, J=11.90 Hz, 2H) 3.05 (d, J=6.35 Hz, 2H) 2.71-2.91 (m, 2H) 2.44 (s, 3H) 1.75-1.96 (m, 3H) 1.28-1.47 (m, 2H). MS (ESI+) m/z 313 (M+H)⁺.

Example 44 tert-butyl 4-(2-{[2-(4-carbamoyl-5-methyl-1H-pyrrol-2-yl)phenyl]amino}ethyl)piperidine-1-carboxylate Example 44 was prepared according to the procedure used for the preparation of Example 40, substituting tert-butyl 4-(2-oxoethyl)piperidine-1-carboxylate for tert-butyl 3-formylpyrrolidine-1-carboxylate, to provide the title compound (94 mg, 55%). ¹H NMR (300 MHz, DMSO-d₆) δ 11.04 (s, 1H) 6.99-7.20 (m, 3H) 6.50-6.71 (m, 4H) 4.80 (t, J=5.59 Hz, 1H) 3.85-3.96 (m, 2H) 3.08-3.16 (m, 2H) 2.60-2.75 (m, 2H) 2.43 (s, 3H) 1.61-1.71 (m, 2H) 1.46-1.58 (m, 3H) 1.38 (s, 9H) 0.92-1.10 (m, 2H). MS (ESI+) m/z 427 (M+H)⁺.

Example 45 tert-butyl [cis-4-({[2-(4-carbamoyl-5-methyl-1H-pyrrol-2-yl)phenyl]amino}methyl)cyclohexyl]carbamate Example 45 was prepared according to the procedure used for the preparation of Example 40, substituting tert-butyl (1s,4s)-4-formylcyclohexylcarbamate for tert-butyl 3-formylpyrrolidine-1-carboxylate, to provide the title compound (137 mg, 80%). ¹H NMR (300 MHz, DMSO-d₆) δ 11.04 (s, 1H) 7.03-7.20 (m, 3H) 6.49-6.73 (m, 5H) 4.87 (t, J=5.59 Hz, 1H) 3.43-3.51 (m, 1H) 3.00 (t, J=6.27 Hz, 2H) 2.43 (s, 3H) 1.63-1.72 (m, 1H) 1.40-1.59 (m, 8H) 1.38 (s, 9H). MS (ESI+) m/z 427 (M+H)⁺.

Example 46 tert-butyl [trans-4-({[2-(4-carbamoyl-5-methyl-1H-pyrrol-2-yl)phenyl]amino}methyl)cyclohexyl]carbamate Example 46 was prepared according to the procedure used for the preparation of Example 40, substituting tert-butyl (1r,4r)-4-formylcyclohexylcarbamate for tert-butyl 3-formylpyrrolidine-1-carboxylate, to provide the title compound (131 mg, 77%). ¹H NMR (300 MHz, DMSO-d₆) δ 11.04 (s, 1H) 7.01-7.20 (m, 3H) 6.46-6.71 (m, 5H) 4.93 (t, J=5.76 Hz, 1H) 3.10-3.21 (m, 1H) 2.95 (t, J=6.27 Hz, 2H) 2.43 (s, 3H) 1.71-1.82 (m, 4H) 1.45-1.54 (m, 1H) 1.36 (s, 9H) 0.87-1.19 (m, 4H). MS (ESI+) m/z 427 (M+H)⁺.

Example 47

2-methyl-5-(2-{[2-(piperidin-4-yl)ethyl]amino}phenyl)-1H-pyrrole-3-carboxamide

Example 47 was prepared according to the procedure used for the preparation of Example 42, substituting the product from Example 44 for the product from Example 40, to provide the title compound (49 mg, 61%) as a hydrochloric acid salt. ¹H NMR (300 MHz, DMSO-d₆) δ 11.18 (s, 1H) 8.70-8.83 (m, 1H) 8.41-8.58 (m, 1H) 7.09-7.26 (m, 2H) 6.71-6.87 (m, 2H) 6.66 (d, J=2.78 Hz, 1H) 3.23 (d, J=12.29 Hz, 2H) 3.13 (t, J=7.34 Hz, 2H) 2.72-2.89 (m, 2H) 2.44 (s, 3H) 1.81 (d, J=13.48 Hz, 2H) 1.47-1.66 (m, 3H) 1.22-1.41 (m, 2H). MS (ESI+) m/z 327 (M+H)⁺.

Example 48

5-(2-{[(cis-4-aminocyclohexyl)methyl]amino}phenyl)-2-methyl-1H-pyrrole-3-carboxamide Example 48 was prepared according to the procedure used for the preparation of Example 42, substituting the product from Example 45 for the product from Example 40, to provide the title compound (119 mg, 99%) as a hydrochloric acid salt. ¹H NMR (300 MHz, DMSO-d₆) δ 11.11 (s, 1H) 7.89 (s, 2H) 7.04-7.21 (m, 2H) 6.55-6.76 (m, 3H) 3.12-3.24 (m, 1H) 3.04 (d, J=7.14 Hz, 2H) 2.44 (s, 3H) 1.73-1.84 (m, 1H) 1.59-1.69 (m, 4H) 1.46-1.58 (m, 4H). MS (ESI+) m/z 327 (M+H)⁺.

Example 49

5-(2-{[(trans-4-aminocyclohexyl)methyl]amino}phenyl)-2-methyl-1H-pyrrole-3-carboxamide Example 49 was prepared according to the procedure used for the preparation of Example 42, substituting the product from Example 46 for the product from Example 40, to provide the title compound (109 mg, 95%) as a hydrochloric acid salt. ¹H NMR (300 MHz, DMSO-d₆) δ 11.16 (s, 1H) 7.94 (s, 2H) 7.01-7.27 (m, 2H) 6.68-6.79 (m, 2H) 6.64 (d, J=2.78 Hz, 1H) 2.85-3.00 (m, 3H) 2.44 (s, 3H) 1.95 (d, J=10.31 Hz, 2H) 1.82 (d, J=11.90 Hz, 2H) 1.49-1.62 (m, 1H) 1.18-1.36 (m, 2H) 0.93-1.09 (m, 2H). MS (ESI+) m/z 327 (M+H)⁺.

Example 50 tert-butyl [4-({[2-(4-carbamoyl-5-methyl-1H-pyrrol-2-yl)phenyl]amino}methyl)phenyl]carbamate Example 50 was prepared according to the procedure used for the preparation of Example 40, substituting tert-butyl 4-formylphenylcarbamate for tert-butyl 3-formylpyrrolidine-1-carboxylate, to provide the title compound (119 mg, 71%). $^1$H NMR (300 MHz, DMSO-$d_6$) δ 11.06 (s, 1H) 9.23 (s, 1H) 7.34-7.40 (m, 2H) 7.22-7.27 (m, 2H) 7.11-7.18 (m, 2H) 6.92-7.02 (m, 1H) 6.70 (d, J=2.71 Hz, 1H) 6.54-6.64 (m, 2H) 6.49 (d, J=8.14 Hz, 1H) 5.56 (t, J=5.93 Hz, 1H) 4.29 (d, J=5.76 Hz, 2H) 2.45 (s, 3H) 1.46 (s, 9H). MS (ESI+) m/z 421 (M+H)$^+$.

Example 51 tert-butyl [3-({[2-(4-carbamoyl-5-methyl-1H-pyrrol-2-yl)phenyl]amino}methyl)phenyl]carbamate Example 51 was prepared according to the procedure used for the preparation of Example 40, substituting tert-butyl 3-formylphenylcarbamate for tert-butyl 3-formylpyrrolidine-1-carboxylate, to provide the title compound (103 mg, 61%). $^1$H NMR (300 MHz, DMSO-$d_6$) δ 11.07 (s, 1H) 9.29 (s, 1H) 7.48 (s, 1H) 7.29 (d, J=8.33 Hz, 1H) 7.13-7.20 (m, 2H) 7.09 (s, 1H) 6.92-7.01 (m, 2H) 6.72 (d, J=2.78 Hz, 1H) 6.56-6.65 (m, 2H) 6.45 (d, J=7.54 Hz, 1H) 5.65 (t, J=6.15 Hz, 1H) 4.32 (d, J=5.95 Hz, 2H) 2.45 (s, 3H) 1.45 (s, 9H). MS (ESI+) m/z 421 (M+H)$^+$.

Example 52

5-{2-[(4-aminobenzyl)amino]phenyl}-2-methyl-1H-pyrrole-3-carboxamide

Example 52 was prepared according to the procedure used for the preparation of Example 42, substituting Example 50 for Example 40, to provide the title compound (92 mg, 87%) as a hydrochloric acid salt. $^1$H NMR (300 MHz, DMSO-$d_6$) δ 11.13 (s, 1H) 10.17 (s, 2H) 7.49 (d, J=8.48 Hz, 2H) 7.32 (d, J=8.48 Hz, 2H) 7.17 (dd, J=7.46, 1.36 Hz, 1H) 6.92-7.01 (m, 1H) 6.76 (d, J=2.37 Hz, 1H) 6.62 (t, J=7.12 Hz, 1H) 6.44 (d, J=8.14 Hz, 1H) 4.41 (s, 2H) 2.46 (s, 3H). MS (ESI+) m/z 321 (M+H)$^+$.

Example 53

5-{2-[(3-aminobenzyl)amino]phenyl}-2-methyl-1H-pyrrole-3-carboxamide

Example 53 was prepared according to the procedure used for the preparation of Example 42, substituting Example 51 for Example 40, to provide the title compound (65 mg, 72%) as a hydrochloric acid salt. $^1$H NMR (300 MHz, DMSO-$d_6$) δ 11.12 (s, 1H) 10.04 (s, 2H) 7.35-7.49 (m, 3H) 7.14-7.24 (m, 2H) 6.92-7.00 (m, 1H) 6.78 (d, J=2.38 Hz, 1H) 6.62 (t, J=6.94 Hz, 1H) 6.42 (d, J=7.54 Hz, 1H) 4.44 (s, 2H) 2.46 (s, 3H). MS (ESI+) m/z 321 (M+H)$^+$.

Example 54

5-{2-[(4-hydroxybenzyl)amino]phenyl}-2-methyl-1H-pyrrole-3-carboxamide

Example 54 was prepared according to the procedure used for the preparation of Example 40, substituting 4-hydroxybenzaldehyde for tert-butyl 3-formylpyrrolidine-1-carboxylate. Purification by flash chromatography (silica gel, 4-5% methanol in dichloromethane) afforded the title compound (55 mg, 43%). $^1$H NMR (300 MHz, DMSO-$d_6$) δ11.06 (s, 1H) 9.21 (s, 1H) 7.09-7.22 (m, 4H) 6.93-7.02 (m, 1H) 6.44-6.77 (m, 6H) 5.48 (t, J=5.93 Hz, 1H) 4.24 (d, J=6.10 Hz, 2H) 2.44 (s, 3H). MS (ESI+) m/z 322 (M+H)$^+$.

Example 55

5-[2-({[5-(hydroxymethyl)furan-2-yl]methyl}amino)phenyl]-2-methyl-1H-pyrrole-3-carboxamide Example 55 was prepared according to the procedure used for the preparation of Example 40, substituting 5-(hydroxymethyl)furan-2-carbaldehyde for tert-butyl 3-formylpyrrolidine-1-carboxylate. Purification by flash chromatography (silica gel, 4-5% methanol in dichloromethane) afforded the title compound (39 mg, 30%). $^1$H NMR (300 MHz, DMSO-$d_6$) δ11.06 (s, 1H) 7.00-7.22 (m, 3H) 6.54-6.79 (m, 4H) 6.08-6.28 (m, 2H) 5.40 (t, J=6.10 Hz, 1H) 5.12 (t, J=5.76, 1H) 4.26-4.39 (m, 4H) 2.44 (s, 3H). MS (ESI−) m/z 324 (M−H)$^+$.

Example 56

5-{2-[(1H-indol-5-ylmethyl)amino]phenyl}-2-methyl-1H-pyrrole-3-carboxamide

Example 56a tert-butyl 5-((2-(4-carbamoyl-5-methyl-1H-pyrrol-2-yl)phenylamino)methyl)-1H-indole-1-carboxylate Example 56a was prepared according to the procedure used for the preparation of Example 40, substituting tert-butyl 5-formyl-1H-indole-1-carboxylate for tert-butyl 3-formylpyrrolidine-1-carboxylate, to provide the title compound (113 mg, 64%).

Example 56b

5-{2-[(1H-indol-5-ylmethyl)amino]phenyl}-2-methyl-1H-pyrrole-3-carboxamide

Example 56b was prepared according to the procedure used for the preparation of Example 42, substituting Example 56a for Example 40. Purification by reverse phase HPLC (C18, 20-95% acetonitrile in 10 mM ammonium acetate/water) afforded the title compound (21 mg, 25%). $^1$H NMR (300 MHz, DMSO-$d_6$) δ 11.08 (s, 1H) 10.99 (s, 1H) 7.52 (s, 1H) 7.26-7.35 (m, 2H) 7.06-7.19 (m, 3H) 6.89-7.00 (m, 1H) 6.73 (d, J=2.38 Hz, 1H) 6.50-6.64 (m, 3H) 6.33-6.36 (m, 1H) 5.58 (t, J=5.75 Hz, 1H) 4.42 (d, J=5.55 Hz, 2H) 2.44 (s, 3H). MS (ESI+) m/z 345 (M+H)$^+$.

Example 57

5-{2-[(cyclopentylmethyl){4-[3-(dimethylamino)propoxy]benzyl}amino]phenyl}-2-methyl-1H-pyrrole-3-carboxamide Example 14 (30 mg, 0.1 mmol), 4-(3-(dimethylamino)propoxy)benzaldehyde (41 mg, 0.2 mmol) and acetic acid (0.058 mL, 1.0 mmol) were combined in the mixture of methanol/dichloromethane (1:1, 1.7 mL). The reaction mixture was shaken at 50° C. for 40 minutes. MP-cyanoborohydride (macroporous triethylammonium methylpolystyrene cyanoborohydride) resin (163 mg, 0.35 mmol) was added. The resulting mixture was shaken at 50° C. overnight, filtered, and concentrated. The residue was purified by reverse phase HPLC (C8(2), 5 µM 100 Å column, 10-100% acetonitrile and 0.1% TFA in water) to afford the title compound (14 mg, 19%) as a trifluoroacetic acid salt. $^1$H NMR (400 MHz, DMSO-d$_6$) δ 7.47 (d, J=7.32 Hz, 1H) 7.09-7.28 (m, 3H) 7.08 (d, J=8.54 Hz, 2H) 6.85-6.96 (m, 1H) 6.82 (d, J=8.54 Hz, 2H) 3.92-4.13 (m, 4H) 3.15-3.24 (m, 2H) 2.75-2.92 (m, 8H) 2.44-2.48 (m, 3H) 2.01-2.14 (m, 2H) 1.89-1.99 (m, 1H) 1.32-1.59 (m, 6H) 0.94-1.04 (m, 2H). MS (ESI+) m/z 489 (M+H)$^+$.

Example 58

5-(2-{[(1-acetyl-1H-indol-3-yl)methyl](cyclopentylmethyl)amino}phenyl)-2-methyl-1H-pyrrole-3-carboxamide Example 58 was prepared according to the procedure used for the preparation of Example 57, substituting 1-acetyl-1H-indole-3-carbaldehyde for 4-(3-(dimethylamino)propoxy)benzaldehyde, to provide the title compound (9.7 mg, 17%) as a trifluoroacetic acid salt. $^1$H NMR (400 MHz, DMSO-d$_6$) δ 8.24 (d, J=8.24 Hz, 1H) 7.53 (s, 1H) 7.48 (dd, J=7.17, 1.68 Hz, 1H) 7.08-7.34 (m, 6H) 6.87-6.94 (m, 1H) 4.24 (s, 2H) 2.97 (s, 2H) 2.54 (s, 3H) 2.34 (s, 3H) 1.99-2.09 (m, 1H) 1.33-1.67 (m, 6H) 1.02-1.14 (m, 2H). MS (ESI+) m/z 469 (M+H)$^+$.

Example 59

5-(2-{[4-(acetylamino)benzyl](cyclopentylmethyl)amino}phenyl)-2-methyl-1H-pyrrole-3-carboxamide Example 59 was prepared according to the procedure used for the preparation of Example 57, substituting N-(4-formylphenyl)acetamide for 4-(3-(dimethylamino)propoxy)benzaldehyde, to provide the title compound (11.6 mg, 21%) as a trifluoroacetic acid salt. $^1$H NMR (400 MHz, DMSO-d$_6$) δ 7.41-7.52 (m, 3H) 7.09-7.32 (m, 3H) 7.07 (d, J=8.54 Hz, 3H) 3.97-4.15 (m, 2H) 2.87 (s, 2H) 2.45 (s, 3H) 2.02 (s, 3H) 1.88-1.97 (m, 1H) 1.31-1.59 (m, 6H) 0.95-1.05 (m, 2H). MS (ESI+) m/z 445 (M+H)$^+$.

Example 60

5-{2-[(cyclopentylmethyl)(thiophen-2-ylmethyl)amino]phenyl}-2-methyl-1H-pyrrole-3-carboxamide Example 60 was prepared according to the procedure used for the preparation of Example 57, substituting thiophene-2-carbaldehyde for 4-(3-(dimethylamino)propoxy)benzaldehyde, to provide the title compound (14 mg, 27%) as a trifluoroacetic acid salt. $^1$H NMR (400 MHz, DMSO-d$_6$) δ 7.52 (dd, J=7.78, 1.68 Hz, 1H) 7.39 (d, J=3.97 Hz, 1H) 7.09-7.23 (m, 3H) 6.94 (dd, J=5.04, 3.51 Hz, 2H) 6.88 (d, J=3.05 Hz, 1H) 4.25 (s, 2H) 2.88 (d, J=6.41 Hz, 2H) 2.48 (s, 3H) 1.89-2.02 (m, 1H) 1.31-1.64 (m, 6H) 1.01-1.11 (m, 2H). MS (ESI−) m/z 392 (M−H)$^+$.

Example 61

5-{2-[(cyclopentylmethyl)(4-methoxybenzyl)amino]phenyl}-2-methyl-1H-pyrrole-3-carboxamide Example 61 was prepared according to the procedure used for the preparation of Example 57, substituting 4-methoxybenzaldehyde for 4-(3-(dimethylamino)propoxy)benzaldehyde, to provide the title compound (9.4 mg, 18%) as a trifluoroacetic acid salt. $^1$H NMR (400 MHz, DMSO-d$_6$) δ 7.47 (d, J=7.32 Hz, 1H) 7.01-7.40 (m, 5H) 6.76-7.01 (m, 3H) 3.97-4.15 (m, 2H) 3.70 (s, 3H) 2.87 (s, 2H) 2.45 (s, 3H) 1.93 (s, 1H) 1.29-1.62 (m, 6H) 0.95-1.05 (m, 2H). MS (ESI+) m/z 418 (M+H)$^+$.

Example 62

5-[2-(cyclohexylamino)phenyl]-2-methyl-1H-pyrrole-3-carboxamide

Example 62 was prepared according to the procedure used for the preparation of Example 11, substituting cyclohexanone for 4-chlorobenzaldehyde and purification by preparative HPLC (C8(2) 5 µm 100 Å column, 10-100% acetonitrile and 0.1% TFA in water), to provide the title compound (0.043 g, 73%). $^1$H NMR (300 MHz, DMSO-d$_6$) δ 11.06 (s, 1H), 7.11 (m, 3H), 6.65 (m, 4H), 4.69 (s, 1H), 3.29 (m, 1H), 2.43 (s, 3H), 1.93 (m, 2H), 1.62 (m, 3H), 1.27 (m, 5H). MS (ESI+) m/z 298.0 (M+H)$^+$.

Example 63

2-methyl-5-[2-(tetrahydrofuran-3-ylamino)phenyl]-1H-pyrrole-3-carboxamide

Example 63 was prepared according to the procedure used for the preparation of Example 11, substituting dihydrofuran-3(2H)-one for 4-chlorobenzaldehyde, to provide the title compound (0.0138 g, 24%). $^1$H NMR (300 MHz, DMSO-d$_6$) δ 11.07 (s, 1H), 7.13 (m, 3H), 6.68 (m, 2H), 6.63 (d, J=2.78 Hz, 1H), 6.58 (s, 1H), 4.82 (d, J=6.74 Hz, 1H), 4.08 (m, 1H), 3.91 (dd, J=8.72, 5.95 Hz, 1H), 3.81 (q, J=7.27 Hz, 1H), 3.70 (td, J=8.23, 5.75 Hz, 1H), 3.56 (dd, J=8.72, 3.57 Hz, 1H), 2.44 (s, 3H), 2.24 (m, 1H), 1.78 (m, 1H). MS (ESI+) m/z 286.0 (M+H)$^+$.

Example 64

2-methyl-5-[2-(pyrrolidin-3-ylamino)phenyl]-1H-pyrrole-3-carboxamide

Example 64a tert-butyl 3-((2-(4-carbamoyl-5-methyl-1H-pyrrol-2-yl)phenyl)amino)pyrrolidine-1-carboxylate Example 64a was prepared according to the procedure used for the preparation of Example 11, substituting tert-butyl 3-oxopyrrolidine-1-carboxylate for 4-chlorobenzaldehyde, to provide the title compound.

Example 64b 2-methyl-5-[2-(pyrrolidin-3-ylamino)phenyl]-1H-pyrrole-3-carboxamide Example 64a in 1,4-dioxane (5 mL) and methanol (1 mL) was treated with a hydrochloric acid solution (4 N in 1,4-dioxane) (1 mL, 4.00 mmol) and stirred at ambient temperature for 1.5 hours. The reaction mixture was concentrated to dryness and purified by reverse phase HPLC (C8(2), 5 µM 100 Å column, 10-100% acetonitrile and 0.1% TFA in water) to give the title compound (0.0316 g, 40%). $^1$H NMR (300 MHz, DMSO-d$_6$) δ 11.05 (s, 1H), 8.72 (s, 1H), 7.16 (m, 3H), 6.68 (m, 4H), 4.98 (m, 1H), 4.20 (m, 1H), 3.33 (m, 2H), 3.18 (m, 2H), 2.45 (s, 3H), 2.30 (m, 1H), 1.93 (m, 1H). MS (ESI+) m/z 285.0 (M+H)$^+$.

Example 65

2-methyl-5-[2-(piperidin-4-ylamino)phenyl]-1H-pyrrole-3-carboxamide

Example 65a tert-butyl 4-((2-(4-carbamoyl-5-methyl-1H-pyrrol-2-yl)phenyl)amino)piperidine-1-carboxylate Example 65a was prepared according to the procedure used for the preparation of Example 11, substituting tert-butyl 4-oxopiperidine-1-carboxylate for 4-chlorobenzaldehyde, to provide the title compound (0.05 g, 62%).

Example 65b 2-methyl-5-[2-(piperidin-4-ylamino)phenyl]-1H-pyrrole-3-carboxamide Example 65b was prepared according to the procedure used for the preparation of Example 64b, substituting Example 65a for Example 64a, to provide the title compound (0.047 g, 91%). $^1$H NMR (300 MHz, DMSO-d$_6$) δ 11.09 (s, 1H), 8.50 (m, 1H), 8.19 (m, 1H), 7.14 (m, 3H), 6.77 (d, J=7.93 Hz, 1H), 6.66 (m, 3H), 4.67 (s, 1H), 3.62 (m, 1H), 3.29 (d, J=13.09 Hz, 2H), 3.03 (m, 2H), 2.44 (s, 3H), 2.10 (d, J=11.50 Hz, 2H), 1.54 (m, 2H). MS (ESI+) m/z 299.0 (M+H)$^+$.

Example 66

5-[2-(cyclobutylamino)phenyl]-2-methyl-1H-pyrrole-3-carboxamide

Example 66 was prepared according to the procedure used for the preparation of Example 75, substituting cyclobutanone for 2-fluorocyclohexanone, to provide the title compound (0.0066 g, 13%). $^1$H NMR (400 MHz, DMSO-d$_6$/D$_2$O) δ 7.15 (m, 2H), 6.69 (m, 2H), 6.58 (d, J=7.5 Hz, 1H), 3.91 (m, 1H), 2.72 (d, J=18.2 Hz, 2H), 2.40 (d, J=34.4 Hz, 3H), 1.75 (d, J=8.4 Hz, 2H), 1.22 (m, 2H). MS (ESI+) m/z 270 (M+H)$^+$.

Example 67

5-[2-(2,3-dihydro-1H-inden-1-ylamino)phenyl]-2-methyl-1H-pyrrole-3-carboxamide

Example 67 was prepared according to the procedure used for the preparation of Example 75, substituting 2,3-dihydro-1H-inden-1-one for 2-fluorocyclohexanone, to provide the title compound (0.0106 g, 17%). $^1$H NMR (400 MHz, DMSO-d$_6$/D$_2$O) δ 7.32 (m, 3H), 7.16 (m, 3H), 6.94 (d, J=8.2 Hz, 1H), 6.73 (t, J=7.4 Hz, 1H), 6.60 (s, 1H), 5.04 (t, J=7.3 Hz, 1H), 2.92 (m, 2H), 2.62 (m, 1H), 2.40 (m, 3H), 1.80 (m, 1H). MS (ESI+) m/z 332 (M+H)$^+$.

Example 68

2-methyl-5-[2-(tetrahydro-2H-thiopyran-4-ylamino)phenyl]-1H-pyrrole-3-carboxamide Example 68 was prepared according to the procedure used for the preparation of Example 75, substituting dihydro-2H-thiopyran-4(3H)-one for 2-fluorocyclohexanone, to provide the title compound (0.0137 g, 23%). $^1$H NMR (400 MHz, DMSO-d$_6$/D$_2$O) δ 7.17 (m, 2H), 6.79 (m, 2H), 6.64 (s, 1H), 3.35 (ddd, J=10.3, 7.0, 3.3 Hz, 1H), 2.77 (m, 2H), 2.64 (d, J=13.9 Hz, 2H), 2.46 (d, J=10.0 Hz, 3H), 2.20 (m, 2H), 1.54 (m, 2H). MS (ESI+) m/z 316 (M+H)$^+$.

Example 69

5-[2-(2,3-dihydro-1H-inden-2-ylamino)phenyl]-2-methyl-1H-pyrrole-3-carboxamide

Example 69 was prepared according to the procedure used for the preparation of Example 75, substituting 1H-inden-2(3H)-one for 2-fluorocyclohexanone, to provide the title compound (0.0082 g, 13%). $^1$H NMR (400 MHz, DMSO-d$_6$/D$_2$O) δ 7.27 (m, 1H), 7.20 (m, 2H), 7.12 (m, 3H), 6.88 (d, J=8.1 Hz, 1H), 6.75 (dd, J=10.7, 4.2 Hz, 1H), 6.57 (s, 1H), 4.35 (p, J=6.7 Hz, 1H), 3.35 (dd, J=15.9, 7.2 Hz, 2H), 2.87 (dd, J=15.9, 5.7 Hz, 2H), 2.42 (s, 3H). MS (ESI+) m/z 332 (M+H)$^+$.

Example 70

2-methyl-5-[2-(tetrahydro-2H-pyran-4-ylamino)phenyl]-1H-pyrrole-3-carboxamide

Example 70 was prepared according to the procedure used for the preparation of Example 75, substituting dihydro-2H-pyran-4(3H)-one for 2-fluorocyclohexanone, to provide the title compound (0.0209 g, 38%). $^1$H NMR (400 MHz, DMSO-d$_6$/D$_2$O) δ 7.18 (m, 2H), 6.88 (d, J=8.0 Hz, 1H), 6.80 (dd, J=10.9, 4.1 Hz, 1H), 6.66 (s, 1H), 3.86 (dd, J=8.3, 3.1 Hz, 2H), 3.53 (m, 1H), 3.41 (m, 2H), 2.45 (s, 3H), 1.90 (d, J=12.5 Hz, 2H), 1.52 (m, 2H). MS (ESI+) m/z 300 (M+H)$^+$.

Example 71

5-[2-(1-azabicyclo[2.2.2]oct-3-ylamino)phenyl]-2-methyl-1H-pyrrole-3-carboxamide Example 71 was prepared according to the procedure used for the preparation of Example 75, substituting quinuclidin-3-one for 2-fluorocyclohexanone, to provide the title compound (0.0105 g, 16%). $^1$H NMR (400 MHz, DMSO-d$_6$/D$_2$O) δ 7.22 (dd, J=7.5, 1.5 Hz, 1H), 7.12 (m, 1H), 6.75 (dd, J=23.0, 15.4 Hz, 1H), 6.67 (d, J=9.1 Hz, 2H), 3.88 (s, 1H), 3.26 (m, 4H), 3.05 (d, J=12.4 Hz, 1H), 2.57 (s, 1H), 2.46 (d, J=2.0 Hz, 3H), 2.37 (d, J=7.8 Hz, 1H), 2.27 (d, J=12.7 Hz, 1H), 1.94 (d, J=8.5 Hz, 2H), 1.79 (s, 1H). MS (ESI+) m/z 325 (M+H)$^+$.

Example 72

2-methyl-5-{2-[tricyclo[3.3.1.1$^{3,7}$]dec-2-ylamino]phenyl}-1H-pyrrole-3-carboxamide Example 72 was prepared according to the procedure used for the preparation of Example 75, substituting adamantanone for 2-fluorocyclohexanone, to provide the title compound (0.0105 g, 16%). $^1$H NMR (400 MHz, DMSO-d$_6$/D$_2$O) δ 7.12 (m, 2H), 6.69 (dd, J=11.8, 4.5 Hz, 3H), 3.55 (s, 1H), 2.45 (s, 3H), 1.95 (s, 2H), 1.83 (s, 4H), 1.74 (d, J=13.1 Hz, 4H), 1.70 (s, 2H), 1.53 (d, J=12.0 Hz, 2H). MS (ESI+) m/z 350 (M+H)$^+$.

Example 73

5-[2-(cycloheptylamino)phenyl]-2-methyl-1H-pyrrole-3-carboxamide

Example 73 was prepared according to the procedure used for the preparation of Example 75, substituting cycloheptanone for 2-fluorocyclohexanone, to provide the title compound (0.0145 g, 25%). $^1$H NMR (400 MHz, DMSO-d$_6$/D$_2$O) δ 7.19 (m, 2H), 6.79 (m, 2H), 6.63 (s, 1H), 3.42 (d, J=3.9 Hz, 1H), 2.45 (s, 3H), 1.90 (dd, J=13.1, 3.6 Hz, 2H), 1.54 (m, 10H) MS (ESI+) m/z 312 (M+H)$^+$.

Example 74

2-methyl-5-[2-(1,2,3,4-tetrahydronaphthalen-2-ylamino)phenyl]-1H-pyrrole-3-carboxamide Example 74 was prepared according to the procedure used for the preparation of Example 75, substituting 3,4-dihydronaphthalen-2(1H)-one for 2-fluorocyclohexanone, to provide the title compound (0.0095 g, 15%). $^1$H NMR (400 MHz, DMSO-d$_6$/D$_2$O) δ 7.18 (dt, J=12.2, 4.1 Hz, 2H), 7.09 (m, 5H), 6.86 (t, J=8.5 Hz, 1H), 6.76 (m, 1H), 6.58 (s, 1H), 3.11 (dd, J=16.1, 4.6 Hz, 1H), 2.87 (m, 2H), 2.75 (dt, J=18.1, 10.4 Hz, 2H), 2.43 (s, 3H), 2.13 (t, J=12.1 Hz, 1H), 1.72 (m, 1H). MS (ESI+) m/z 346 (M+H)$^+$.

Example 75

5-{2-[(2-fluorocyclohexyl)amino]phenyl}-2-methyl-1H-pyrrole-3-carboxamide

A 4 mL vial was charged with a stirbar, a solution of Example 1e (0.04 g, 0.18 mmol) in dichloromethane (1 mL), a solution of 2-fluorocylcohexanone (0.025 g, 0.22 mmol) in dichloromethane (1 mL), and acetic acid (0.053 mL, 0.92 mmol), and sodium triacetoxyborohydride (0.06 g, 0.27 mmol). The vial was capped and allowed to stir at ambient temperature for 16 hours. Upon completion, the crude material was filtered, dried, and purified by reverse phase HPLC (C8(2), 5 μM 100 Å column, 10-100% acetonitrile and 0.1% TFA in water) to afford the title compound (0.0023 g, 4%). $^1$H NMR (400 MHz, DMSO-d$_6$/D$_2$O) δ 7.13 (m, 2H), 6.78 (d, J=8.1 Hz, 1H), 6.67 (d, J=7.5 Hz, 1H), 6.60 (s, 1H), 4.85 (d, J=52.2 Hz, 1H), 3.55 (d, J=18.3 Hz, 1H), 2.45 (d, J=7.9 Hz, 3H), 1.97 (m, 1H), 1.77 (m, 4H), 1.47 (m, 4H). MS (ESI+) m/z 316 (M+H)$^+$.

Example 76

2-methyl-5-{2-[(phenylacetyl)amino]phenyl}-1H-pyrrole-3-carboxamide

A solution of Example 1e (0.065 g, 0.3 mmol) and diisopropylethylamine (0.105 mL, 0.6 mmol) in tetrahydrofuran (1.5 mL) was treated dropwise with phenacyl chloride (0.048 mL, 0.36 mmol), stirred for 1 hour, and partitioned between ethyl acetate and brine. The organic layer was separated and concentrated. Purification by reverse phase HPLC (C8(2), 5 μM 100 Å column, 10-100% acetonitrile and 0.1% TFA in water) afforded the title compound (0.035 g, 35%) $^1$H NMR (300 MHz, DMSO-d$_6$) δ 11.09-11.13 (m, 1H) 9.15-9.20 (m, 1H) 7.57-7.65 (m, 1H) 7.36-7.42 (m, 1H) 7.15-7.35 (m, 7H) 6.98 (s, 1H) 6.66 (d, J=2.71 Hz, 1H) 6.59-6.63 (m, 1H) 3.64-3.74 (m, 2H) 2.43-2.46 (m, 3H). MS (ESI−) m/z 332 (M−H)$^+$.

Example 77

2-methyl-5-[2-(phenylamino)phenyl]-1H-pyrrole-3-carboxamide

To a mixture of Example 1e (0.043 g, 0.2 mmol), phenylboronic acid (0.037 g, 0.300 mmol), copper (II) acetate (7.27 mg, 0.040 mmol), and myristic acid (0.018 g, 0.080 mmol) was added toluene (1.0 mL) and 2,6-lutidine (0.047 mL, 0.400 mmol). The reaction mixture was left open to the air and stirred vigorously overnight at ambient temperature. The reaction mixture was diluted with ethyl acetate, washed with saturated aqueous sodium bicarbonate solution, water and brine, dried (anhydrous MgSO$_4$), filtered and concentrated. The residue was purified by flash chromatography (silica gel, 3% methanol in dichloromethane) to provide the title compound (0.33 g, 57%). $^1$H NMR (300 MHz, DMSO-d$_6$) δ 11.07 (s, 1H), 7.39 (dd, J=7.63, 1.53 Hz, 1H), 7.19 (m, 5H), 6.99 (m, 4H), 6.81 (m, 1H), 6.75 (d, J=2.71 Hz, 1H), 6.53 (s, 1H), 2.43 (s, 3H). MS (ESI+) m/z 291.9 (M+H)$^+$.

Example 78

2-methyl-5-{2-[(phenylsulfonyl)amino]phenyl}-1H-pyrrole-3-carboxamide

To the mixture of Example 1e (0.20 g, 0.929 mmol) and DMAP (0.114 g, 0.929 mmol) in dioxane (10 mL) was added benzenesulfonyl chloride (0.164 g, 0.929 mmol). The mixture was heated at 60° C. for 4 hours. The reaction mixture was directly purified by preparative thin layer chromatography (silica gel, dichloromethane/methanol, 12/1) to provide the title compound (0.056 g, 17% yield). $^1$H NMR (400 MHz, DMSO-d$_6$) δ 10.90 (s, 1H), 9.35 (s, 1H), 7.64-7.56 (m, 3H), 7.45 (t, J=7.6 Hz, 2H), 7.32 (dd, J=7.6, 1.2 Hz, 1H), 7.22-7.18 (m, 1H), 7.15-7.11 (m, 1H), 7.03-7.01 (m, 1H), 6.94 (s, 1H), 6.64 (d, J=2.4 Hz, 2H), 2.42 (s, 3H). MS (ESI+) m/z 356.8 (M+H)

Example 79

5-{2-[(cyclohexylsulfonyl)amino]phenyl}-2-methyl-1H-pyrrole-3-carboxamide

Example 79 was prepared according to the procedure used for the preparation of Example 78, substituting cyclohexanesulfonyl chloride for benzenesulfonyl chloride, to provide the title compound. $^1$H NMR (400 MHz, DMSO-d$_6$) δ 11.13 (s, 1H), 8.53 (s, 1H), 7.40-7.36 (m, 2H), 7.30-7.26 (m, 2H), 7.01 (s, 1H), 6.71 (d, J=2.4 Hz, 2H), 2.62-2.56 (m, 1H), 2.45 (s, 3H), 1.78-1.75 (m, 2H), 1.64-1.61 (m, 2H), 1.52-1.49 (m, 1H), 1.21-0.95 (m, 5H). MS (ESI+) m/z 362.2 (M+H)

Example 80

2-methyl-5-{2-[(pyridin-3-ylsulfonyl)amino]phenyl}-1H-pyrrole-3-carboxamide

A mixture of Example 1e (0.10 g, 0.465 mmol) and triethylamine (0.097 mL, 0.70 mmol) was stirred in THF (10 mL). To this mixture was added pyridine-3-sulfonyl chloride (0.082 g, 0.465 mmol). The reaction mixture was heated to 60° C. for 3 hours. The reaction was quenched by the addition of brine (10 mL), diluted with water, and extracted with ethyl acetate. The combined organics were dried over anhydrous sodium sulfate, filtered and concentrated. The residue was dissolved in dichloromethane and purified by flash chromatography (silica gel, 0.5-10% methanol/dichloromethane gradient) to provide the title compound (0.036 g, 22% yield). $^1$H NMR (400 MHz, DMSO-$d_6$) δ 11.12 (s, 1H), 9.67 (s, 1H), 8.68 (d, J=1.6 Hz, 2H), 7.93-7.90 (m, 1H), 7.42-7.39 (m, 1H), 7.35-7.32 (m, 1H), 7.13-7.06 (m, 3H), 6.94 (s, 1H), 6.65 (d, J=2.0 Hz, 2H), 2.40 (s, 3H). MS (ESI+): m/z 357.1 (M+H).

Example 81

5-(2-{[(4-chlorophenyl)sulfonyl]amino}phenyl)-2-methyl-1H-pyrrole-3-carboxamide

Example 81 was prepared according to the procedure used for the preparation of Example 80, substituting 4-chlorobenzene-1-sulfonyl chloride for pyridine-3-sulfonyl chloride, to provide the title compound. $^1$H NMR (400 MHz, DMSO-$d_6$) δ 10.81 (s, 1H), 7.54 (s, 1H), 7.53-7.50 (m, 2H), 7.47-7.44 (m, 2H), 7.31 (dd, J=7.6, 1.6 Hz, 1H), 7.26-7.22 (m, 1H), 7.20-7.16 (m, 1H), 7.09 (dd, J=8.0, 1.2 Hz, 1H), 6.90 (s, 1H), 6.62 (d, J=2.4 Hz, 2H), 2.41 (s, 3H). MS (ESI+) m/z 390.0 (M+H)

Example 82

2-methyl-5-(2-{[(3,3,3-trifluoropropyl)sulfonyl]amino}phenyl)-1H-pyrrole-3-carboxamide Example 82 was prepared according to the procedure used for the preparation of Example 80, substituting 3,3,3-trifluoropropane-1-sulfonyl chloride for pyridine-3-sulfonyl chloride, to provide the title compound. $^1$H NMR (400 MHz, DMSO-$d_6$) δ 11.25 (s, 1H), 9.14 (s, 1H), 7.44-7.41 (m, 1H), 7.38-7.35 (m, 1H), 7.28-7.26 (m, 2H), 6.99 (s, 1H), 6.79 (d, J=2.4 Hz, 1H), 6.63 (s, 1H), 3.11-3.07 (m, 2H), 2.44 (s, 5H). MS (ESI+) m/z 376.1 (M+H).

Example 83

5-{2-[(benzylsulfonyl)amino]phenyl}-2-methyl-1H-pyrrole-3-carboxamide

Example 83 was prepared according to the procedure used for the preparation of Example 80, substituting phenylmethanesulfonyl chloride for pyridine-3-sulfonyl chloride, to provide the title compound. $^1$H NMR (400 MHz, DMSO-$d_6$) δ 11.30 (s, 1H), 8.67 (s, 1H), 7.42-7.39 (m, 1H), 7.32-7.31 (m, 4H), 7.26-7.25 (m, 2H), 7.19-7.18 (m, 2H), 7.04 (s, 1H), 6.75 (d, J=1.6 Hz, 1H), 6.63 (s, 1H), 4.30 (s, 2H), 2.44 (s, 3H). MS (ESI+) m/z 370.0 (M+H).

Example 84

5-(2-{[(2,4-difluorophenyl)sulfonyl]amino}-phenyl)-2-methyl-1H-pyrrole-3-carboxamide A mixture of Example 1e (0.30 g, 1.39 mmol) and dimethylaminopyridine (0.255 g, 2.09 mmol) was stirred in 1,4-dioxane (10 mL). To this mixture was added 2,4-difluorobenzene-1-sulfonyl chloride (0.326 g, 1.53 mmol). The reaction mixture was heated at 60° C. for 3 hours and then cooled to ambient temperature. The reaction was quenched by the addition of brine, diluted with water, and extracted with ethyl acetate. The combined organics were dried over anhydrous sodium sulfate, filtered and concentrated. The residue was dissolved in dichloromethane and purified by flash chromatography (silica gel, 0.5-10% methanol in dichloromethane gradient) to provide the title compound (0.35 g, 13% yield). $^1$H NMR (400 MHz, DMSO-$d_6$) δ 10.84 (s, 1H), 9.65 (s, 1H), 7.46 (q, J=8.4 Hz, 1H), 7.30-7.12 (m, 5H), 7.06-7.02 (m, 1H), 6.78-6.69 (m, 1H), 6.61 (s, 1H), 6.50 (d, J=2 Hz, 1H), 2.40 (s, 3H). MS (ESI) m/z 392.0 (M+H).

Example 85

5-(2-{[(4-chlorobenzyl)sulfonyl]amino}phenyl)-2-methyl-1H-pyrrole-3-carboxamide

Example 85 was prepared according to the procedure used for the preparation of Example 80, substituting (4-chlorophenyl)methanesulfonyl chloride for pyridine-3-sulfonyl chloride, to provide the title compound. $^1$H NMR (400 MHz, DMSO-$d_6$) δ 11.21 (s, 1H), 8.68 (s, 1H), 7.41-7.33 (m, 4H), 7.26 (d, J=8.4 Hz, 2H), 7.21-7.19 (m, 2H), 7.04 (s, 1H), 6.75 (d, J=2.4 Hz, 1H), 6.65 (s, 1H), 4.35 (s, 2H), 2.44 (s, 3H). MS (ESI+) m/z 404.0 (M+H).

Example 86

2-methyl-5-(2-{[(2,2,2-trifluoroethyl)sulfonyl]amino}phenyl)-1H-pyrrole-3-carboxamide Example 86 was prepared according to the procedure used for the preparation of Example 80, substituting 2,2,2-trifluoroethanesulfonyl chloride for pyridine-3-sulfonyl chloride, to provide the title compound. $^1$H NMR (400 MHz, DMSO-$d_6$) δ 11.16 (s, 1H), 9.52 (s, 1H), 7.46-7.39 (m, 2H), 7.31-7.25 (m, 2H), 6.99 (s, 1H), 6.76 (d, J=2.8 Hz, 1H), 6.64 (s, 1H), 4.24-4.16 (q, J=10.0 Hz, 2H), 2.45 (s, 3H). MS (ESI+) m/z 362.0 (M+H).

Example 87

5-{2-[(cyclopentylsulfonyl)amino]phenyl}-2-methyl-1H-pyrrole-3-carboxamide

Example 87 was prepared according to the procedure used for the preparation of Example 80, substituting cyclopentanesulfonyl chloride for pyridine-3-sulfonyl chloride, to provide the title compound. $^1$H NMR 400 MHz, CDCl$_3$) δ 9.13 (s, 1H), 7.51 (d, J=7.6 Hz, 1H), 7.38-7.30 (m, 2H), 7.22 (t, J=7.6 Hz, 1H), 7.17 (s, 1H), 6.42 (d, J=2.8 Hz, 1H), 5.63 (s, 2H), 3.65-3.61 (m, 1H), 2.57 (s, 3H), 2.08-1.97 (m, 4H), 1.87-1.77 (m, 2H), 1.67-1.60 (m, 2H). MS (ESI) m/z 348.0 (M+H).

Example 88

5-(2-{[(4-hydroxyphenyl)sulfonyl]amino}phenyl)-2-methyl-1H-pyrrole-3-carboxamide A mixture of Example 1e (0.10 g, 0.465 mmol) and triethylamine (0.097 mL, 0.697 mmol) was stirred in THF (10 mL). To the mixture was added 4-hydroxybenzene-1-sulfonyl chloride (0.089 g, 0.465 mmol). The reaction mixture was heated at 60° C. for 3 hours. The reaction was quenched by the addition of brine (10 mL), diluted with water, and extracted with ethyl acetate. The combined organics were dried over anhydrous sodium sulfate, filtered and concentrated. The residue was dissolved in dichloromethane and purified by flash chromatography (silica gel, 0.5-10% methanol in dichloromethane gradient) to provide the title compound (0.12 g, 8.6% yield). $^1$H NMR (400

MHz, CD₃OD) δ 7.28-7.22 (m, 3H), 7.14-7.05 (m, 3H), 6.62 (d, J=8.8 Hz, 2H), 6.41 (s, 1H), 2.39 (s, 3H), 2.05 (s, 1H). MS (ESI+) m/z 372.0 (M+H).

Example 89

2-methyl-5-(2-phenoxyphenyl)-1H-pyrrole-3-carboxamide

Example 89a tert-butyl 2-acetyl-4-oxo-4-(2-phenoxyphenyl)butanoate

Example 89a was prepared according to the procedure used for the preparation of Example 1a, substituting 2-bromo-1-(2-phenoxyphenyl)ethanone for 2-bromo-2'-nitroacetophenone, to provide the title compound (0.338 g, 89%).

Example 89b tert-butyl 2-methyl-5-(2-phenoxyphenyl)-1H-pyrrole-3-carboxylate Example 89b was prepared according to the procedure used for the preparation of Example 1b, substituting Example 89a for Example 1a, to provide the title compound (0.285 g, 89%).

Example 89c 2-methyl-5-(2-phenoxyphenyl)-1H-pyrrole-3-carboxylic acid

Example 89c was prepared according to the procedure used for the preparation of Example 1c, substituting Example 89b for Example 1b, to provide the title compound (0.26 g, 100%).

Example 89d 2-methyl-5-(2-phenoxyphenyl)-1H-pyrrole-3-carboxamide

Example 89d was prepared according to the procedure used for the preparation of Example 1d, substituting Example 89c for Example 1c, to provide the title compound (0.026 g, 55%). $^1$H NMR (300 MHz, DMSO-d₆) δ 11.13 (s, 1H), 7.69 (m, 1H), 7.34 (m, 2H), 7.19 (m, 2H), 7.08 (m, 2H), 6.97 (m, 2H), 6.91 (m, 2H), 6.54 (s, 1H), 2.43 (s, 3H). MS (ESI+) m/z 293.1 (M+H)⁺.

Example 90

5-(2,4-dimethylphenyl)-2-methyl-1H-pyrrole-3-carboxamide

Example 90a tert-butyl 2-acetyl-4-(2,4-dimethylphenyl)-4-oxobutanoate

Example 90a was prepared according to the procedure used for the preparation of Example 1a, substituting 2-bromo-1-(2,4-dimethylphenyl)ethanone for 2-bromo-2'-nitroacetophenone, to provide the title compound (0.609 g, 91%).

Example 90b tert-butyl 5-(2,4-dimethylphenyl)-2-methyl-1H-pyrrole-3-carboxylate Example 90b was prepared according to the procedure used for the preparation of Example 1b, substituting Example 90a for Example 1a, to provide the title compound (0.581 g, 99%).

Example 90c 5-(2,4-dimethylphenyl)-2-methyl-1H-pyrrole-3-carboxylic acid

Example 90c was prepared according to the procedure used for the preparation of Example 1c, substituting Example 90b for Example 1b, to provide the title compound (0.43 g, 93%).

Example 90d 5-(2,4-dimethylphenyl)-2-methyl-1H-pyrrole-3-carboxamide

Example 90d was prepared according to the procedure used for the preparation of Example 1d, substituting Example 90c for Example 1c, to provide the title compound (0.03 g, 60%). $^1$H NMR (300 MHz, DMSO-d₆) δ 10.99 (s, 1H), 7.27 (d, J=7.80 Hz, 1H), 7.11 (s, 1H), 7.04 (m, 2H), 6.57 (d, J=3.05 Hz, 1H), 6.52 (s, 1H), 2.44 (s, 3H), 2.36 (s, 3H), 2.27 (s, 3H). MS (ESI+) m/z 229.1 (M+H)⁺.

Example 91

5-(2-amino-6-phenoxyphenyl)-2-methyl-1H-pyrrole-3-carboxamide

Example 91a 2-(1-ethoxyvinyl)-1-fluoro-3-nitrobenzene

A mixture of 2-bromo-1-fluoro-3-nitrobenzene (1.364 g, 6.20 mmol) and dichlorobis(triphenylphosphine)palladium (II) (0.435 g, 0.620 mmol) was degassed and flushed with nitrogen. 1,4-Dioxane (15.5 mL) and tributyl(1-ethoxyvinyl)tin (2.51 mL, 7.44 mmol) were added sequentially under nitrogen. The resulting mixture was heated at 95° C. for 4.5 hours and then cooled to ambient temperature. A solution of potassium fluoride (1.4 g in 12 mL water) was added followed by the addition of ethyl acetate. The mixture was stirred overnight and was then filtered through diatomaceous earth, rinsing with 500 mL of ethyl acetate. The filtrate was washed with water and brine, dried (anhydrous MgSO₄), filtered and concentrated. The residue was purified by flash chromatography (silica gel, 2 to 20% ethyl acetate in hexanes) to provide the title compound (0.91 g, 70%).

Example 91b 1-(2-fluoro-6-nitrophenyl)ethanone

Example 91a (0.91 g, 4.31 mmol) in tetrahydrofuran (21.54 mL) was treated with a hydrochloric acid solution (2

M aqueous) (4.31 mL, 8.62 mmol) and stirred at ambient temperature overnight. The reaction mixture was diluted with ethyl acetate, neutralized with saturated sodium bicarbonate solution, washed with water and brine, dried (anhydrous MgSO$_4$), filtered and concentrated. The residue was purified by flash chromatography (silica gel, 2 to 15% ethyl acetate in hexanes) to provide the title compound (0.775 g, 98%).

Example 91c 1-(2-nitro-6-phenoxyphenyl)ethanone

Example 91b, phenol (0.029 g, 0.310 mmol) and cesium carbonate (2.76 g, 8.46 mmol) were combined with dimethylformamide (21 mL), heated at 50° C. for three hours and then stirred overnight at ambient temperature. The reaction mixture was partitioned between ethyl acetate and water, and the organic phase was washed with brine, dried (anhydrous MgSO$_4$), filtered and concentrated. The residue was purified by flash chromatography (silica gel, 1 to 10% ethyl acetate in hexanes) to provide the title compound (1.06 g, 97%).

Example 91d 2-bromo-1-(2-nitro-6-phenoxyphenyl)ethanone

To a solution of Example 91c (0.99 g, 3.86 mmol) in acetic acid (5.14 mL) was added a solution of bromine (0.238 mL, 4.63 mmol) in acetic acid (5.14 mL). The resulting mixture was heated at 100° C. for 4 hours. Additional bromine (0.238 mL, 4.63 mmol) was added and heating was continued for another 2 hours at 100° C. The reaction mixture was cooled to ambient temperature, partitioned between ethyl acetate and water, and the organic phase was washed with aqueous sodium carbonate solution and brine, dried (anhydrous MgSO$_4$), filtered and concentrated. The residue was purified by flash chromatography (silica gel, 0 to 12% ethyl acetate in hexanes) to provide a mixture of mono- and di-brominated products. The mixture of products was dissolved in tetrahydrofuran (5 mL), treated with diethyl phosphite (0.523 mL, 4.05 mmol) and triethylamine (0.565 mL, 4.05 mmol), and stirred at ambient temperature for 2 hours and 20 minutes. The reaction mixture was partitioned between ethyl acetate and water, and the organic phase was washed with brine, dried (anhydrous MgSO$_4$), filtered and concentrated. The residue was purified by flash chromatography (silica gel, 2 to 14% ethyl acetate in hexanes) to provide the title compound (0.695 g, 54%).

Example 91e tert-butyl 2-acetyl-4-(2-nitro-6-phenoxyphenyl)-4-oxobutanoate

A suspension of sodium hydride (60% oil dispersion) (0.079 g, 1.971 mmol) in tetrahydrofuran (6.16 mL) at 0° C. was treated dropwise with tert-butyl 3-oxobutanoate (0.300 mL, 1.806 mmol) and stirred for 30 minutes. The resulting mixture was then treated with a solution of Example 91d (0.69 g, 1.642 mmol) in tetrahydrofuran (2.053 mL) and stirred, allowing the temperature to rise slowly toward ambient temperature. After 9 hours, the reaction mixture was cooled to 0° C., and additional tert-butyl 3-oxobutanoate (0.300 mL, 1.806 mmol) and sodium hydride (60% oil dispersion) (0.079 g, 1.971 mmol) were added and the mixture was stirred overnight. The reaction mixture was partitioned between ethyl acetate and saturated aqueous ammonium chloride solution, and the organic phase was washed with brine, dried (anhydrous MgSO$_4$), filtered and concentrated. The residue was purified by flash chromatography (silica gel, 5 to 10% ethyl acetate in hexanes). The purest fractions containing the title compound were combined, concentrated and subjected to a second purification by flash chromatography (silica gel, 2 to 12% ethyl acetate in hexanes) to provide the title compound (0.466 g, 69%).

Example 91f tert-butyl 2-methyl-5-(2-nitro-6-phenoxyphenyl)-1H-pyrrole-3-carboxylate Example 91f was prepared according to the procedure used for the preparation of Example 1b, substituting Example 91e for Example 1a, to provide the title compound (0.253 g, 94%).

Example 91g 2-methyl-5-(2-nitro-6-phenoxyphenyl)-1H-pyrrole-3-carboxylic acid

Example 91g was prepared according to the procedure used for the preparation of Example 1c, substituting Example 91f for Example 1b, to provide the title compound (0.375 g, 99%).

Example 91h 2-methyl-5-(2-nitro-6-phenoxyphenyl)-1H-pyrrole-3-carboxamide

Example 91h was prepared according to the procedure used for the preparation of Example 1d, substituting Example 91g for Example 1c, to provide the title compound (0.155 g, 42%).

Example 91i 5-(2-amino-6-phenoxyphenyl)-2-methyl-1H-pyrrole-3-carboxamide

Example 91i was prepared according to the procedure used for the preparation of Example 1e, substituting Example 91h for Example 1d and purification by flash chromatography (silica gel, 0 to 5% methanol in dichloromethane), to provide the title compound (0.105 g, 76%). $^1$H NMR (300 MHz, DMSO-d$_6$) δ 10.85 (s, 1H), 7.28 (m, 2H), 7.00 (m, 3H), 6.89 (m, 2H), 6.53 (dd, J=8.14, 1.02 Hz, 1H), 6.43 (m, J=2.71 Hz, 2H), 6.06 (dd, J=7.80, 1.02 Hz, 1H), 5.01 (s, 2H), 2.37 (s, 3H). MS (ESI+) m/z 308.0 (M+H)$^+$.

Example 92

5-[4-(3,5-dimethyl-1,2-oxazol-4-yl)phenyl]-2-methyl-1H-pyrrole-3-carboxamide

Example 92a ethyl 2-acetyl-4-(4-bromophenyl)-4-oxobutanoate

Example 92a was prepared according to the procedure used for the preparation of Example 1a, substituting ethyl 3-oxobutanoate for tert-butyl 3-oxobutanoate and 2-bromo-1-(4-bromophenyl)ethanone for 2-bromo-2'-nitroacetophenone, to provide the title compound (5.05 g, 77%).

Example 92b ethyl 5-(4-bromophenyl)-2-methyl-1H-pyrrole-3-carboxylate

Example 92b was prepared according to the procedure used for the preparation of Example 1b, substituting Example 92a for Example 1a, to provide the title compound (4.27 g, 90%).

Example 92c 5-(4-bromophenyl)-2-methyl-1H-pyrrole-3-carboxylic acid

Example 92c was prepared according to the procedure used for the preparation of Example 3c, substituting Example 92b for Example 3b, to provide the title compound (2.65 g, 90%).

Example 92d 5-(4-bromophenyl)-2-methyl-1H-pyrrole-3-carboxamide

Example 92d was prepared according to the procedure used for the preparation of Example 1d, substituting Example 92c for Example 1c, to provide the title compound (2.37 g, 90%).

Example 92e

5-[4-(3,5-dimethyl-1,2-oxazol-4-yl)phenyl]-2-methyl-1H-pyrrole-3-carboxamide

Example 92d (0.028 g, 0.1 mmol), 3,5-dimethylisoxazol-4-ylboronic acid (0.0202 g, 0.143 mmol) and bis(triphenylphosphine)palladium(II) chloride (7.02 mg, 10.00 μmol) were combined in a microwave vial equipped with a magnetic stirbar. The vial was capped, degassed and flushed with nitrogen. 1,4-Dioxane (0.667 mL), ethanol (0.333 mL) and 2 M aqueous sodium carbonate solution (0.1 mL, 0.2 mmol) were added via syringe under nitrogen. The reaction mixture was heated in a microwave reactor at 130° C. for 20 minutes. The reaction mixture was then partitioned between ethyl acetate and water, and the organic phase was washed with water and brine, dried (anhydrous $MgSO_4$), filtered and concentrated. The residue was purified by flash chromatography (silica gel, 0 to 10% methanol in dichloromethane) to provide the title compound (0.02 g, 68%). $^1$H NMR (300 MHz, DMSO-$d_6$) δ 11.39 (s, 1H), 7.64 (d, J=8.33 Hz, 2H), 7.38 (d, J=8.33 Hz, 2H), 7.15 (s, 1H), 6.94 (d, J=2.78 Hz, 1H), 6.65 (s, 1H), 2.48 (s, 3H), 2.42 (s, 3H), 2.25 (s, 3H). MS (ESI+) m/z 296.1 (M+H)$^+$.

Example 93 methyl N-({5-[4-(3,5-dimethyl-1,2-oxazol-4-yl)phenyl]-2-methyl-1H-pyrrol-3-yl}carbonyl)-beta-alaninate Example 93a ethyl 5-(4-(3,5-dimethylisoxazol-4-yl)phenyl)-2-methyl-1H-pyrrole-3-carboxylate Example 93a was prepared according to the procedure used for the preparation of Example 92e, substituting Example 92b for Example 92d, to provide the title compound (0.09 g, 37%).

Example 93b 5-(4-(3,5-dimethylisoxazol-4-yl)phenyl)-2-methyl-1H-pyrrole-3-carboxylic acid Example 93b was prepared according to the procedure used for the preparation of Example 3c, substituting Example 93a for Example 3b, to provide the title compound (0.284 g, 86%).

Example 93c methyl N-({5-[4-(3,5-dimethyl-1,2-oxazol-4-yl)phenyl]-2-methyl-1H-pyrrol-3-yl}carbonyl)-beta-alaninate Example 93c was prepared according to the procedure used for the preparation of Example 1d, substituting Example 93b for Example 1c and methyl 3-aminopropanoate hydrochloride for ammonium chloride, to provide the title compound (0.034 g, 53%) after purification by reverse phase HPLC (C8(2), 5 μM 100 Å column, 10-100% acetonitrile and 0.1% TFA in water). $^1$H NMR (300 MHz, DMSO-$d_6$) δ 11.39 (s, 1H), 7.71 (t, J=5.75 Hz, 1H), 7.65 (m, J=8.33 Hz, 2H), 7.38 (m, J=8.73 Hz, 2H), 6.90 (d, J=2.78 Hz, 1H), 3.61 (s, 3H), 3.42 (q, J=6.74 Hz, 2H), 2.55 (t, J=7.14 Hz, 2H), 2.47 (s, 3H), 2.42 (s, 3H), 2.25 (s, 3H). MS (ESI+) m/z 382.0 (M+H)$^+$.

Example 94 methyl N-({5-[4-(3,5-dimethyl-1,2-oxazol-4-yl)phenyl]-2-methyl-1H-pyrrol-3-yl}carbonyl)glycinate Example 94 was prepared according to the procedure used for the preparation of Example 1d, substituting Example 93b for Example 1c and methyl 2-aminoacetate hydrochloride for ammonium chloride, to provide the title compound (0.029 g, 47%) after purification by reverse phase HPLC (C8(2), 5 μM 100 Å column, 10-100% acetonitrile and 0.1% TFA in water). $^1$H NMR (300 MHz, DMSO-$d_6$) δ 11.46 (s, 1H), 8.10 (t, J=5.75 Hz, 1H), 7.66 (m, J=8.33 Hz, 2H), 7.39 (m, J=8.33 Hz, 2H), 6.96 (d, J=2.38 Hz, 1H), 3.93 (d, J=5.55 Hz, 2H), 3.65 (s, 3H), 2.48 (s, 3H), 2.43 (s, 3H), 2.25 (s, 3H). MS (ESI+) m/z 367.9 (M+H)$^+$.

Example 95

5-[4-(3,5-dimethyl-1,2-oxazol-4-yl)phenyl]-N-hydroxy-2-methyl-1H-pyrrole-3-carboxamide Example 93b (0.05 g, 0.169 mmol), O-(7-azabenzotriazol-1-yl)-N,N,N',N'-tetramethyluronium hexafluorophosphate (0.071 g, 0.186 mmol), and N,N-diisopropylethylamine (0.059 mL, 0.337 mmol) were combined and dissolved in dimethylformamide (0.422 mL). A solution of hydroxylamine hydrochloride (0.023 g, 0.337 mmol) and N,N-diisopropylethylamine (0.059 mL, 0.337 mmol) in dimethylformamide (0.422 mL) was added and the mixture was stirred at 40° C. overnight. The reaction mixture was partitioned between ethyl acetate and water, and the organic phase was washed with saturated aqueous sodium bicarbonate solution, water and brine, dried (anhydrous $MgSO_4$), filtered and concentrated. The residue was purified by reverse phase HPLC (C8(2), 5 μM 100 Å column, 10-100% acetonitrile and 0.1% TFA in water) to provide the title compound (0.017 g, 32%). $^1$H NMR (400 MHz, DMSO-$d_6$) δ 11.43 (s, 1H), 10.38 (s, 1H), 7.63 (m, J=8.54 Hz, 2H), 7.38 (m, J=8.24 Hz, 2H), 6.80 (d, J=2.75 Hz, 1H), 2.48 (s, 3H), 2.42 (s, 3H), 2.25 (s, 3H).

Example 96 ethyl N-benzyl-N-({5-[4-(3,5-dimethyl-1,2-oxazol-4-yl)phenyl]-2-methyl-1H-pyrrol-3-yl}carbonyl)-beta-alaninate Example 96 was prepared according to the procedure used for the preparation of Example 1d, substituting Example 93b for Example 1c and ethyl 3-(benzylamino)propanoate for ammonium chloride, to provide the title compound (0.041 g, 45%) after purification by reverse phase HPLC (C8(2), 5 μM 100 Å column, 10-100% acetonitrile and 0.1% TFA in water). $^1$H NMR (300 MHz, DMSO-$d_6$) δ 11.42 (s, 1H), 7.63 (m, 2H), 7.33 (m, 7H), 6.53 (s, 1H), 4.71 (s, 2H), 4.03 (q, J=7.12 Hz, 2H), 3.56 (t, J=6.27 Hz, 2H), 2.60 (t, J=7.12 Hz, 2H), 2.40 (s, 3H), 2.33 (s, 3H), 2.23 (s, 3H), 1.15 (t, J=7.12 Hz, 3H). MS (ESI+) m/z 486.0 $(M+H)^+$.

Example 97

2-methyl-5-{4'-[(4-methylpiperazin-1-yl)methyl]biphenyl-4-yl}-1H-pyrrole-3-carboxamide A microwave vial was charged with a stirbar, a solution of Example 92d (0.020 g, 0.072 mmol) in ethanol (1.0 mL), a solution of 1-methyl-4-(4-(4,4,5,5-tetramethyl-1,3,2-dioxaborolan-2-yl)benzyl)piperazine (0.027 g, 0.086 mmol) in ethanol (0.287 mL), a 1 M aqueous solution of cesium carbonate (0.215 mL, 0.215 mmol), and Siliacat-DPP immobilized Pd catalyst (0.0265 g, 0.27 mmol/g loading). The reaction vial was capped and placed in a microwave reactor at 120° C. for 20 minutes. Upon completion, the reaction mixture was filtered, concentrated to dryness, and purified by reverse phase HPLC (C8(2), 5 μM 100 Å column, 10-100% acetonitrile and 0.1% TFA in water) to provide the title compound (0.019 g, 43%). $^1$H NMR (500 MHz, DMSO-$d_6$/$D_2O$) δ 11.54 (d, J=1.83 Hz, 1H), 7.80 (d, J=8.24 Hz, 2H), 7.72 (q, J=8.54 Hz, 4H), 7.57 (d, J=8.24 Hz, 2H), 6.95 (d, J=2.44 Hz, 1H), 4.25 (s, 2H), 3.93 (m, 2H), 3.37 (m, J=46.38 Hz, 6H), 2.87 (s, 3H), 2.49 (s, 3H). MS (ESI+) m/z 389.1 $(M+H)^+$.

Example 98

5-(3'-hydroxybiphenyl-4-yl)-2-methyl-1H-pyrrole-3-carboxamide

Example 98 was prepared according to the procedure used for the preparation of Example 97, substituting 3-(4,4,5,5-tetramethyl-1,3,2-dioxaborolan-2-yl)phenol for 1-methyl-4-(4-(4,4,5,5-tetramethyl-1,3,2-dioxaborolan-2-yl)benzyl)piperazine, to provide the title compound (0.0137, 39%). $^1$H NMR (400 MHz, DMSO-$d_6$/$D_2O$) δ 11.46 (s, 1H), 7.64 (m, 4H), 7.28 (t, J=7.78 Hz, 1H), 7.12 (d, J=7.63 Hz, 1H), 7.07 (m, J=1.83 Hz, 1H), 6.93 (d, J=2.44 Hz, 1H), 6.77 (dd, J=7.93, 2.14 Hz, 1H), 2.48 (s, 3H). MS (ESI+) m/z 292.9 $(M+H)^+$.

Example 99

2-methyl-5-(3',4',5'-trimethoxybiphenyl-4-yl)-1H-pyrrole-3-carboxamide

Example 99 was prepared according to the procedure used for the preparation of Example 97, substituting 3,4,5-trimethoxyphenylboronic acid for 1-methyl-4-(4-(4,4,5,5-tetramethyl-1,3,2-dioxaborolan-2-yl)benzyl)piperazine, to provide the title compound (0.0143 g, 32%). $^1$H NMR (400 MHz, DMSO-$d_6$/$D_2O$) δ 7.68 (m, 4H), 6.94 (s, 3H), 3.87 (s, 6H), 3.70 (m, 3H), 2.49 (s, 3H). MS (ESI+) m/z 367 $(M+H)^+$ Example 100

5-[4-(furan-3-yl)phenyl]-2-methyl-1H-pyrrole-3-carboxamide

Example 100 was prepared according to the procedure used for the preparation of Example 97, substituting furan-3-ylboronic acid for 1-methyl-4-(4-(4,4,5,5-tetramethyl-1,3,2-dioxaborolan-2-yl)benzyl)piperazine, to provide the title compound (0.0025 g, 8%). $^1$H NMR (400 MHz, DMSO-$d_6$/$D_2O$) δ 8.16 (s, 1H), 7.72 (s, 1H), 7.60 (m, 4H), 6.96 (s, 1H), 6.89 (s, 1H), 2.47 (s, 3H). MS (ESI+) m/z 267 $(M+H)^+$.

Example 101

2-methyl-5-[4-(thiophen-3-yl)phenyl]-1H-pyrrole-3-carboxamide

Example 101 was prepared according to the procedure used for the preparation of Example 97, substituting thiophen-3-ylboronic acid for 1-methyl-4-(4-(4,4,5,5-tetramethyl-1,3,2-dioxaborolan-2-yl)benzyl)piperazine, to provide the title compound (0.0104 g, 30%). $^1$H NMR (400 MHz, DMSO-$d_6$/$D_2O$) δ 7.84 (d, J=2.75 Hz, 1H), 7.73 (d, J=8.24 Hz, 2H), 7.61 (m, 4H), 6.91 (s, 1H), 2.48 (s, 3H). MS (ESI+) m/z 283 $(M+H)^+$.

Example 102

2-methyl-5-[4-(pyridin-4-yl)phenyl]-1H-pyrrole-3-carboxamide

Example 102 was prepared according to the procedure used for the preparation of Example 97, substituting pyridin-4-ylboronic acid for 1-methyl-4-(4-(4,4,5,5-tetramethyl-1,3,2-dioxaborolan-2-yl)benzyl)piperazine, to provide the title compound (0.010 g, 21%). $^1$H NMR (400 MHz, DMSO-$d_6$/$D_2O$) δ 8.84 (d, J=6.41 Hz, 2H), 8.38 (d, J=6.41 Hz, 2H), 8.07 (d, J=8.55 Hz, 2H), 7.82 (d, J=8.24 Hz, 2H), 7.12 (d, J=1.83 Hz, 1H), 2.51 (s, 3H). MS (ESI+) m/z 278 $(M+H)^+$.

Example 103

2-methyl-5-[4-(1-methyl-1H-pyrazol-4-yl)phenyl]-1H-pyrrole-3-carboxamide

Example 103 was prepared according to the procedure used for the preparation of Example 97, substituting 1-methyl-4-(4,4,5,5-tetramethyl-1,3,2-dioxaborolan-2-yl)-1H-pyrazole for 1-methyl-4-(4-(4,4,5,5-tetramethyl-1,3,2-dioxaborolan-2-yl)benzyl)piperazine, to provide the title compound (0.0086 g, 25%). $^1$H NMR (400 MHz, DMSO-d$_6$/D$_2$O) δ 11.39 (s, 1H), 7.57 (m, 3H), 7.37 (t, J=7.63 Hz, 2H), 7.18 (t, J=7.48 Hz, 1H), 6.86 (t, J=3.05 Hz, 1H), 2.57 (s, 3H), 2.46 (s, 3H). MS (ESI+) m/z 281 (M+H)$^+$.

Example 104

5-[3'-(dimethylcarbamoyl)biphenyl-4-yl]-2-methyl-1H-pyrrole-3-carboxamide

Example 104 was prepared according to the procedure used for the preparation of Example 97, substituting N,N-dimethyl-3-(4,4,5,5-tetramethyl-1,3,2-dioxaborolan-2-yl)benzamide for 1-methyl-4-(4-(4,4,5,5-tetramethyl-1,3,2-dioxaborolan-2-yl)benzyl)piperazine, to provide the title compound (0.024 g, 57%). $^1$H NMR (400 MHz, DMSO-d$_6$/D$_2$O) δ 11.49 (s, 1H), 7.78 (d, J=7.93 Hz, 1H), 7.71 (m, 5H), 7.55 (t, J=7.78 Hz, 1H), 7.37 (d, J=7.63 Hz, 1H), 6.96 (d, J=1.53 Hz, 1H), 3.03 (s, 3H), 2.96 (s, 3H), 2.49 (s, 3H). MS (ESI+) m/z 348 (M+H)$^+$.

Example 105

2-methyl-5-[3'-(morpholin-4-yl)biphenyl-4-yl]-1H-pyrrole-3-carboxamide

Example 105 was prepared according to the procedure used for the preparation of Example 97, substituting 3-morpholinophenylboronic acid hydrochloride for 1-methyl-4-(4-(4,4,5,5-tetramethyl-1,3,2-dioxaborolan-2-yl)benzyl)piperazine, to provide the title compound (0.007 g, 15%). $^1$H NMR (400 MHz, DMSO-d$_6$/D$_2$O) δ 7.67 (m, 4H), 7.37 (m, 1H), 7.23 (s, 1H), 7.18 (d, J=7.63 Hz, 1H), 6.99 (dd, J=8.09, 1.98 Hz, 1H), 6.93 (s, 1H), 3.80 (m, 4H), 3.22 (m, 4H), 2.48 (s, 3H). MS (ESI+) m/z 362 (M+H)$^+$.

Example 106

5-{3'-[(furan-2-ylmethyl)carbamoyl]biphenyl-4-yl}-2-methyl-1H-pyrrole-3-carboxamide Example 106 was prepared according to the procedure used for the preparation of Example 97, substituting 3-(furan-2-ylmethylcarbamoyl)phenylboronic acid for 1-methyl-4-(4-(4,4,5,5-tetramethyl-1,3,2-dioxaborolan-2-yl)benzyl)piperazine, to provide the title compound (0.0201 g, 41%). $^1$H NMR (400 MHz, DMSO-d$_6$/D$_2$O) δ 8.17 (s, 1H), 7.86 (dd, J=15.87, 7.63 Hz, 2H), 7.77 (m, 2H), 7.71 (m, 2H), 7.58 (m, 2H), 6.96 (d, J=2.44 Hz, 1H), 6.42 (s, 1H), 6.33 (d, J=3.05 Hz, 1H), 4.52 (s, 2H), 2.49 (s, 3H). MS (ESI+) m/z 400 (M+H)$^+$.

Example 107

5-{4-[(1E)-3-methoxyprop-1-en-1-yl]phenyl}-2-methyl-1H-pyrrole-3-carboxamide

Example 107 was prepared according to the procedure used for the preparation of Example 97, substituting (E)-2-(3-methoxyprop-1-enyl)-4,4,5,5-tetramethyl-1,3,2-dioxaborolane for 1-methyl-4-(4-(4,4,5,5-tetramethyl-1,3,2-dioxaborolan-2-yl)benzyl)piperazine, to provide the title compound (0.0053, 16%). $^1$H NMR (400 MHz, DMSO-d$_6$/D$_2$O) δ 7.61 (m, 2H), 7.46 (m, 2H), 6.89 (d, J=2.14 Hz, 1H), 6.59 (d, J=15.87 Hz, 1H), 6.34 (m, 1H), 4.05 (d, J=6.10 Hz, 2H), 3.29 (s, 3H), 2.46 (s, 3H). MS (ESI+) m/z 271 (M+H)$^+$.

Example 108

5-[4'-(dimethylcarbamoyl)biphenyl-4-yl]-2-methyl-1H-pyrrole-3-carboxamide

Example 108 was prepared according to the procedure used for the preparation of Example 97, substituting (4-(dimethylcarbamoyl)phenyl)boronic acid for 1-methyl-4-(4-(4,4,5,5-tetramethyl-1,3,2-dioxaborolan-2-yl)benzyl)piperazine, to provide the title compound (0.0011 g, 3%). $^1$H NMR (400 MHz, DMSO-d$_6$/D$_2$O) δ 7.74 (m, 6H), 7.50 (d, J=7.93 Hz, 2H), 6.96 (s, 1H), 3.00 (m, 6H), 2.48 (s, 3H). MS (ESI+) m/z 348.0 (M+H)$^+$.

Example 109

2-methyl-5-[4-(pyrimidin-5-yl)phenyl]-1H-pyrrole-3-carboxamide

Example 109 was prepared according to the procedure used for the preparation of Example 97, substituting pyrimidin-5-ylboronic acid for 1-methyl-4-(4-(4,4,5,5-tetramethyl-1,3,2-dioxaborolan-2-yl)benzyl)piperazine, to provide the title compound (0.0052 g, 15%). $^1$H NMR (400 MHz, DMSO-d$_6$/D$_2$O) δ 9.17 (m, 3H), 7.84 (d, J=8.24 Hz, 2H), 7.74 (d, J=8.24 Hz, 2H), 7.00 (d, J=2.44 Hz, 1H), 2.49 (s, 3H). MS (ESI+) m/z 279 (M+H)$^+$.

Example 110

2-methyl-5-{4'-[(methylsulfonyl)amino]biphenyl-4-yl}-1H-pyrrole-3-carboxamide

Example 110 was prepared according to the procedure used for the preparation of Example 97, substituting N-(4-(4,4,5,5-tetramethyl-1,3,2-dioxaborolan-2-yl)phenyl)methanesulfonamide for 1-methyl-4-(4-(4,4,5,5-tetramethyl-1,3,2-dioxaborolan-2-yl)benzyl)piperazine, to provide the title compound (0.0062 g, 14%). $^1$H NMR (400 MHz, DMSO-d$_6$/D$_2$O) δ 7.68 (m, 6H), 7.31 (m, 2H), 6.92 (s, 1H), 3.02 (m, 3H), 2.48 (s, 3H). MS (ESI+) m/z 370 (M+H)$^+$.

Example 111

5-[4-(1-benzyl-1H-pyrazol-4-yl)phenyl]-2-methyl-1H-pyrrole-3-carboxamide

Example 111 was prepared according to the procedure used for the preparation of Example 97, substituting 1-benzyl-4-(4,4,5,5-tetramethyl-1,3,2-dioxaborolan-2-yl)-1H-pyrazole for 1-methyl-4-(4-(4,4,5,5-tetramethyl-1,3,2-dioxaborolan-2-yl)benzyl)piperazine, to provide the title compound (0.0023 g, 5%). $^1$H NMR (400 MHz, DMSO-d$_6$/D$_2$O) δ 8.27 (s, 1H), 7.92 (s, 1H), 7.57 (m, 4H), 7.34 (m, 5H), 6.86 (d, J=1.83 Hz, 1H), 5.35 (s, 2H), 2.47 (s, 3H). MS (ESI+) m/z 357 (M+H)$^+$.

Example 112

5-[4-(3,5-dimethyl-1H-pyrazol-4-yl)phenyl]-2-methyl-1H-pyrrole-3-carboxamide

Example 112 was prepared according to the procedure used for the preparation of Example 97, substituting 3,5- dimethyl-4-(4,4,5,5-tetramethyl-1,3,2-dioxaborolan-2-yl)-1H-pyrazole for 1-methyl-4-(4-(4,4,5,5-tetramethyl-1,3,2-dioxaborolan-2-yl)benzyl)piperazine, to provide the title compound (0.0041 g, 11%). $^1$H NMR (400 MHz, DMSO-$d_6$/$D_2O$) δ 7.62 (d, J=8.24 Hz, 2H), 7.31 (d, J=8.24 Hz, 2H), 6.89 (d, J=1.53 Hz, 1H), 2.48 (s, 3H), 2.25 (s, 6H). MS (ESI+) m/z 295 (M+H)$^+$.

Example 113

2-methyl-5-[4-(quinolin-6-yl)phenyl]-1H-pyrrole-3-carboxamide

Example 113 was prepared according to the procedure used for the preparation of Example 97, substituting 6-(4,4,5,5-tetramethyl-1,3,2-dioxaborolan-2-yl)quinoline for 1-methyl-4-(4-(4,4,5,5-tetramethyl-1,3,2-dioxaborolan-2-yl)benzyl)piperazine, to provide the title compound (0.0066 g, 12%). $^1$H NMR (400 MHz, DMSO-$d_6$/$D_2O$) δ 9.07 (d, J=4.88 Hz, 1H), 8.85 (d, J=8.24 Hz, 1H), 8.52 (s, 1H), 8.38 (d, J=8.85 Hz, 1H), 8.23 (d, J=8.85 Hz, 1H), 7.92 (d, J=8.24 Hz, 2H), 7.85 (dd, J=8.39, 4.73 Hz, 1H), 7.77 (d, J=8.24 Hz, 2H), 7.01 (d, J=1.53 Hz, 1H), 2.50 (s, 3H). MS (ESI+) m/z 328 (M+H)$^+$.

Example 114

2-methyl-5-{4'-[(4-methylpiperazin-1-yl)carbonyl]biphenyl-4-yl}-1H-pyrrole-3-carboxamide Example 114 was prepared according to the procedure used for the preparation of Example 97, substituting 4-(4-methylpiperazine-1-carbonyl)phenylboronic acid for 1-methyl-4-(4-(4,4,5,5-tetramethyl-1,3,2-dioxaborolan-2-yl)benzyl)piperazine, to provide the title compound (0.0087 g, 14%). $^1$H NMR (400 MHz, DMSO-$d_6$/$D_2O$) δ 7.82 (d, J=7.93 Hz, 2H), 7.73 (m, 4H), 7.56 (d, J=8.24 Hz, 2H), 6.96 (d, J=2.14 Hz, 1H), 3.32 (m, 8H), 2.85 (s, 3H), 2.49 (s, 3H). MS (ESI+) m/z 401 (M+H)$^+$.

Example 115

5-(2-bromophenyl)-2-methyl-1H-pyrrole-3-carboxamide

Example 115a 2-bromo-1-(2-bromophenyl)ethanone 1-(2-Bromophenyl)ethanone (21.35 g, 107 mmol) in benzene (101 mL) was treated dropwise over 10 minutes with a solution of bromine (5.25 mL, 102 mmol) in benzene (33.5 mL) and then concentrated to dryness upon completion of the addition. The residue was purified by flash chromatography (silica gel, 1 to 7% ethyl acetate in hexanes) to provide the title compound and unreacted 1-(2-bromophenyl)ethanone as an inseparable mixture (87:13) (25.3 g, 74%).

Example 115b tert-butyl 2-acetyl-4-(2-bromophenyl)-4-oxobutanoate

Example 115b was prepared according to the procedure used for the preparation of Example 1a, substituting Example 115a for 2-bromo-2'-nitroacetophenone, to provide the title compound (8.66 g, 75%).

Example 115c tert-butyl 5-(2-bromophenyl)-2-methyl-1H-pyrrole-3-carboxylate

Example 115c was prepared according to the procedure used for the preparation of Example 1b, substituting Example 115b for Example 1a, to provide the title compound (8.63 g, 99%).

Example 115d 5-(2-bromophenyl)-2-methyl-1H-pyrrole-3-carboxylic acid

Example 115d was prepared according to the procedure used for the preparation of Example 1c, substituting Example 115c for Example 1b, to provide the title compound (1.61 g, 82%).

Example 115e 5-(2-bromophenyl)-2-methyl-1H-pyrrole-3-carboxamide

Example 115e was prepared according to the procedure used for the preparation of Example 1d, substituting Example 115d for Example 1c, to provide the title compound (1.08 g, 75%). $^1$H NMR (300 MHz, DMSO-$d_6$) δ 11.21 (s, 1H), 7.68 (dd, J=7.93, 1.19 Hz, 1H), 7.47 (m, 1H), 7.41 (td, J=7.54, 1.19 Hz, 1H), 7.18 (m, 2H), 6.88 (d, J=2.78 Hz, 1H), 6.58 (s, 1H), 2.45 (s, 3H). MS (ESI+) m/z 279.0 (M+H)$^+$.

Example 116

5-[2-(4-chlorophenoxy)phenyl]-2-methyl-1H-pyrrole-3-carboxamide

Example 115e (0.028 g, 0.1 mmol), 4-chlorophenol (0.026 g, 0.200 mmol), copper(I) iodide (1.905 mg, 10.00 mmol), picolinic acid (2.462 mg, 0.020 mmol), tribasic potassium phosphate (0.042 g, 0.200 mmol) and dimethyl sulfoxide (0.4 mL) were combined, flushed with nitrogen and heated at 95° C. for 22 hours. The reaction mixture was cooled to ambient temperature, partitioned between ethyl acetate and water, and the organic phase was washed with aqueous saturated sodium bicarbonate solution, water and brine, dried (anhydrous MgSO$_4$), filtered and concentrated. The residue was purified by reverse phase HPLC (C8(2), 5 μM 100 Å column, 10-100% acetonitrile and 0.1% TFA in water) to provide the title compound (0.010 g, 31%). $^1$H NMR (300 MHz, DMSO-$d_6$) δ 11.15 (s, 1H), 7.70 (m, 1H), 7.37 (m, 2H), 7.23 (m, 2H), 7.07 (s, 1H), 6.97 (m, 3H), 6.89 (d, J=2.78 Hz, 1H), 6.55 (s, 1H), 2.43 (s, 3H). MS (ESI+) m/z 327.1 (M+H)$^+$.

Example 117

5-[2-(2-fluorophenoxy)phenyl]-2-methyl-1H-pyrrole-3-carboxamide

Example 117 was prepared according to the procedure used for the preparation of Example 116, substituting 2-fluorophenol for 4-chlorophenol, to provide the title compound (0.036 g, 58%). $^1$H NMR (300 MHz, DMSO-$d_6$) δ 11.15 (s, 1H), 7.68 (m, 1H), 7.39 (m, 1H), 7.16 (m, 6H), 6.97 (d, J=2.78 Hz, 1H), 6.72 (m, 1H), 6.55 (s, 1H), 2.47 (s, 3H). MS (ESI+) m/z 311.1 (M+H)$^+$.

Example 118

5-[2-(1H-indol-6-yloxy)phenyl]-2-methyl-1H-pyrrole-3-carboxamide

A microwave vial containing a magnetic stirbar was charged with Example 115e (0.028 g, 0.1 mmol), 1H-indol-6-ol (0.027 g, 0.200 mmol), copper(I) iodide (0.0019 g, 0.010 mmol), tribasic potassium phosphate (0.064 g, 0.300 mmol) and picolinic acid (2.462 mg, 0.020 mmol), capped, degassed and flushed with nitrogen. Dimethyl sulfoxide (0.8 mL) was added via syringe under a nitrogen atmosphere and the reaction mixture was heated in a microwave reactor at 120° C. for 25 minutes. The reaction mixture was partitioned between ethyl acetate and water, and the organic phase was washed with aqueous saturated sodium bicarbonate solution, water and brine, dried (anhydrous MgSO$_4$), filtered and concentrated. The residue was purified by flash chromatography (silica gel, 87:10:3 dichloromethane/ethyl acetate/methanol). The material was further purified by reverse phase HPLC (C8(2), 5 μM 100 Å column, 10-100% acetonitrile and 0.1% TFA in water) to provide the title compound (0.011 g, 16%). $^1$H NMR (400 MHz, DMSO-$d_6$) δ 11.11 (s, 1H), 10.97 (s, 1H), 7.67 (m, 1H), 7.52 (d, J=8.24 Hz, 1H), 7.28 (t, J=2.75 Hz, 1H), 7.13 (m, 2H), 7.08 (s, 1H), 6.98 (d, J=2.44 Hz, 1H), 6.94 (d, J=1.53 Hz, 1H), 6.84 (m, 1H), 6.80 (dd, J=8.54, 2.14 Hz, 1H), 6.53 (s, 1H), 6.40 (m, 1H), 2.45 (s, 3H). MS (ESI+) m/z 331.9 (M+H)$^+$.

Example 119

5-[2-(4-aminophenoxy)phenyl]-2-methyl-1H-pyrrole-3-carboxamide

Example 119a tert-butyl (4-(2-(4-carbamoyl-5-methyl-1H-pyrrol-2-yl)phenoxy)phenyl)carbamate Example 119a was prepared according to the procedure used for the preparation of Example 118, substituting tert-butyl 4-hydroxyphenylcarbamate for 1H-indol-6-ol, to provide the title compound (0.061 g, 75%).

Example 119b

5-[2-(4-aminophenoxy)phenyl]-2-methyl-1H-pyrrole-3-carboxamide

Example 119b was prepared according to the procedure used for the preparation of Example 64b, substituting Example 119a for Example 64a, to provide the title compound (0.04 g, 64%). $^1$H NMR (300 MHz, DMSO-$d_6$) δ 11.15 (s, 1H), 9.10 (s, 2H), 7.70 (m, 1H), 7.22 (m, 4H), 6.98 (m, 4H), 6.88 (d, J=2.78 Hz, 1H), 6.56 (s, 1H), 2.43 (s, 3H). MS (ESI−) m/z 306.2 (M−H)$^-$.

Example 120

2-methyl-5-[2-(pyridin-4-yloxy)phenyl]-1H-pyrrole-3-carboxamide

Example 120 was prepared according to the procedure used for the preparation of Example 118, substituting pyridine-4-ol for 1H-indol-6-ol, to provide the title compound (0.029 g, 36%). $^1$H NMR (300 MHz, DMSO-$d_6$) δ 11.37 (s, 1H), 8.32 (d, J=7.54 Hz, 2H), 7.68 (m, 2H), 7.58 (m, 1H), 7.49 (m, 1H), 6.97 (d, J=7.14 Hz, 2H), 6.91 (s, 1H), 6.60 (s, 1H), 5.79 (d, J=2.78 Hz, 1H), 2.40 (s, 3H). MS (ESI+) m/z 294.0 (M+H)$^+$.

Example 121

5-[2-(4-benzylphenoxy)phenyl]-2-methyl-1H-pyrrole-3-carboxamide

A microwave vial was charged with a stirbar, a solution of Example 115e (0.02 g, 0.072 mmol) in dimethyl sulfoxide (0.5 mL), a solution of 4-benzylphenol (0.0268 g, 0.143 mmol) in dimethyl sulfoxide (0.477 mL), copper(I) iodide (0.00273 g, 0.00144 mmol), picolinic acid (0.00265 g, 0.00216 mmol) and ground tribasic potassium phosphate (0.0304 g, 0.144 mmol). The reaction vial was capped, flushed with nitrogen and heated in a microwave reactor at 140° C. for 30 minutes. Upon completion, the reaction mixture was filtered, and the residue was concentrated to dryness and purified by reverse phase HPLC (C8(2), 5 μM 100 Å column, 10-100% acetonitrile and 0.1% TFA in water) to provide the title compound (0.0064 g, 23%). $^1$H NMR (500 MHz, DMSO-$d_6$/$D_2$O) δ 7.66 (m, 1H), 7.29 (t, J=7.63 Hz, 2H), 7.23 (m, 3H), 7.19 (m, 4H), 6.91 (m, 3H), 6.88 (m, 1H), 3.90 (s, 2H), 2.43 (s, 3H). MS (ESI+) m/z 383.0 (M+H)$^+$.

Example 122

2-methyl-5-[2-(4-phenoxyphenoxy)phenyl]-1H-pyrrole-3-carboxamide

Example 122 was prepared according to the procedure used for the preparation of Example 121, substituting 4-phenoxyphenol for 4-benzylphenol, to provide the title compound (0.0024 g, 9%). $^1$H NMR (500 MHz, DMSO-$d_6$/$D_2$O) δ 7.67 (dd, J=7.48, 1.98 Hz, 1H), 7.39 (t, J=7.78 Hz, 2H), 7.21 (m, 2H), 7.12 (t, J=7.32 Hz, 1H), 7.03 (s, 4H), 6.98 (d, J=8.54 Hz, 2H), 6.92 (m, 2H), 2.45 (s, 3H). MS (ESI+) m/z 385.0 (M+H)$^+$.

Example 123

5-[2-(4-cyanophenoxy)phenyl]-2-methyl-1H-pyrrole-3-carboxamide

Example 123 was prepared according to the procedure used for the preparation of Example 121, substituting 4-hydroxybenzonitrile for 4-benzylphenol, to provide the title compound (0.0025 g, 11%). $^1$H NMR (500 MHz, DMSO-$d_6$/$D_2$O) δ 7.81 (d, J=8.24 Hz, 2H), 7.32 (d, J=8.54 Hz, 2H), 7.07 (m, 2H), 6.73 (t, J=7.48 Hz, 1H), 6.65 (m, 2H), 2.34 (s, 3H). MS (ESI+) m/z 318.0 (M+H)$^+$.

Example 124

5-[2-(4-cyclopentylphenoxy)phenyl]-2-methyl-1H-pyrrole-3-carboxamide

Example 124 was prepared according to the procedure used for the preparation of Example 121, substituting 4-cyclopentylphenol for 4-benzylphenol, to provide the title compound (0.005 g, 19%). $^1$H NMR (500 MHz, DMSO-$d_6$/$D_2$O) δ 7.67 (m, 1H), 7.23 (d, J=8.54 Hz, 2H), 7.19 (m, 2H), 6.91 (m, 4H), 2.93 (m, 1H), 2.44 (s, 3H), 1.99 (m, 2H), 1.75 (m, 2H), 1.63 (m, 2H), 1.49 (m, 2H). MS (ESI+) m/z 361.0 (M+H)+.

Example 125

5-[2-(isoquinolin-5-yloxy)phenyl]-2-methyl-1H-pyrrole-3-carboxamide

Example 125 was prepared according to the procedure used for the preparation of Example 121, substituting isoquinolin-5-ol for 4-benzylphenol, to provide the title compound (0.0065 g, 26%). $^1$H NMR (500 MHz, DMSO-$d_6$/$D_2O$) δ 11.35 (s, 1H), 9.71 (s, 1H), 8.63 (m, 2H), 8.10 (d, J=8.24 Hz, 1H), 7.79 (t, J=8.09 Hz, 1H), 7.75 (dd, J=7.93, 1.53 Hz, 1H), 7.35 (m, 1H), 7.30 (td, J=7.63, 1.53 Hz, 1H), 7.19 (d, J=7.93 Hz, 1H), 7.06 (d, J=7.93 Hz, 1H), 6.90 (d, J=2.75 Hz, 1H), 2.38 (s, 3H). MS (ESI+) m/z 344.0 (M+H)+.

Example 126

2-methyl-5-[2-(pyridin-3-yloxy)phenyl]-1H-pyrrole-3-carboxamide

Example 126 was prepared according to the procedure used for the preparation of Example 121, substituting pyridin-3-ol for 4-benzylphenol, to provide the title compound (0.007 g, 33%). $^1$H NMR (500 MHz, DMSO-$d_6$/$D_2O$) δ 11.33 (s, 1H), 8.41 (d, 2H), 7.74 (dd, J=7.48, 1.68 Hz, 1H), 7.62 (m, 2H), 7.32 (m, 2H), 7.10 (m, 1H), 6.90 (d, J=2.75 Hz, 1H), 2.43 (s, 3H). MS (ESI+) m/z 293.9 (M+H)+.

Example 127

5-[2-(3-cyanophenoxy)phenyl]-2-methyl-1H-pyrrole-3-carboxamide

Example 127 was prepared according to the procedure used for the preparation of Example 121, substituting 3-hydroxybenzonitrile for 4-benzylphenol, to provide the title compound (0.0015 g, 7%). $^1$H NMR (500 MHz, DMSO-$d_6$/$D_2O$) δ 7.72 (dd, J=7.32, 1.83 Hz, 1H), 7.53 (m, 2H), 7.39 (s, 1H), 7.29 (m, 3H), 7.06 (d, J=7.32 Hz, 1H), 6.88 (d, J=2.14 Hz, 1H), 2.43 (s, 3H). MS (ESI+) m/z 317.9 (M+H)+.

Example 128

2-methyl-5-[2-(quinolin-5-yloxy)phenyl]-1H-pyrrole-3-carboxamide

Example 128 was prepared according to the procedure used for the preparation of Example 121, substituting quinolin-5-ol for 4-benzylphenol, to provide the title compound (0.006 g, 24%). $^1$H NMR (500 MHz, DMSO-$d_6$/$D_2O$) δ 11.33 (s, 1H), 9.07 (m, 1H), 9.00 (d, J=8.54 Hz, 1H), 7.78 (m, 4H), 7.30 (m, 2H), 7.02 (d, J=7.93 Hz, 1H), 6.91 (d, J=2.75 Hz, 1H), 6.86 (d, J=7.63 Hz, 1H), 2.38 (s, 3H). MS (ESI+) m/z 343.9 (M+H)+.

Example 129

5-[2-(4-chloro-2-fluorophenoxy)phenyl]-2-methyl-1H-pyrrole-3-carboxamide

Example 129 was prepared according to the procedure used for the preparation of Example 121, substituting 4-chloro-2-fluorophenol for 4-benzylphenol, to provide the title compound (0.006 g, 24%). $^1$H NMR (500 MHz, DMSO-$d_6$/$D_2O$) δ 11.25 (s, 1H), 7.68 (m, 1H), 7.60 (dd, J=10.68, 2.14 Hz, 1H), 7.29 (d, J=8.54 Hz, 1H), 7.19 (d, J=4.27 Hz, 2H), 7.11 (t, J=8.85 Hz, 1H), 6.94 (d, J=2.44 Hz, 1H), 6.81 (m, 1H), 2.46 (s, 3H). MS (ESI+) m/z 344.9 (M+H)+.

Example 130

5-[2-(1H-indol-5-yloxy)phenyl]-2-methyl-1H-pyrrole-3-carboxamide

Example 130 was prepared according to the procedure used for the preparation of Example 121, substituting 1H-indol-5-ol for 4-benzylphenol, to provide the title compound (0.0031 g, 13%). $^1$H NMR (500 MHz, DMSO-$d_6$/$D_2O$) δ 11.17 (s, 1H), 7.64 (dd, J=7.17, 1.68 Hz, 1H), 7.43 (d, J=8.54 Hz, 1H), 7.36 (d, J=2.44 Hz, 1H), 7.16 (d, J=2.14 Hz, 1H), 7.11 (m, 2H), 6.99 (d, J=2.44 Hz, 1H), 6.88 (dd, J=8.70, 1.98 Hz, 1H), 6.76 (m, 1H), 6.40 (d, J=3.05 Hz, 1H), 2.46 (s, 3H). MS (ESI+) m/z 332.0 (M+H)+.

Example 131

2-methyl-5-[2-(pyridin-2-yloxy)phenyl]-1H-pyrrole-3-carboxamide

Example 131 was prepared according to the procedure used for the preparation of Example 121, substituting pyridin-2-ol for 4-benzylphenol, to provide the title compound (0.0035 g, 17%). $^1$H NMR (500 MHz, DMSO-$d_6$/$D_2O$) δ 7.63 (d, J=7.93 Hz, 1H), 7.54 (m, 2H), 7.41 (m, 2H), 7.28 (d, J=7.63 Hz, 1H), 6.48 (d, J=9.46 Hz, 1H), 6.35 (t, J=6.56 Hz, 1H), 5.83 (s, 1H), 2.39 (s, 3H). MS (ESI-) m/z 291.9 (M+H)+.

Example 132

2-methyl-5-{2-[4-(methylsulfonyl)phenoxy]phenyl}-1H-pyrrole-3-carboxamide

Example 132 was prepared according to the procedure used for the preparation of Example 121, substituting 4-(methylsulfonyl)phenol for 4-benzylphenol, to provide the title compound (0.0053 g, 20%). $^1$H NMR (500 MHz, DMSO-$d_6$/$D_2O$) δ 7.88 (d, J=8.54 Hz, 2H), 7.40 (d, J=8.54 Hz, 2H), 7.06 (dd, J=7.48, 1.98 Hz, 2H), 6.74 (m, 1H), 6.66 (d, J=7.93 Hz, 1H), 6.64 (s, 1H), 3.21 (s, 3H), 2.35 (s, 3H). MS (ESI+) m/z 371.0 (M+H)+.

Example 133 methyl 3-{2-[2-(4-carbamoyl-5-methyl-1H-pyrrol-2-yl)phenoxy]phenyl}propanoate Example 133 was prepared according to the procedure used for the preparation of Example 121, substituting methyl 3-(2-hydroxyphenyl)propanoate for 4-benzylphenol, to provide the title compound (0.0015 g, 5.5%). $^1$H NMR (500 MHz, DMSO-$d_6$/$D_2O$) δ 11.21 (s, 1H), 7.69 (m, 1H), 7.35 (d, J=7.63 Hz, 1H), 7.23 (m, 1H), 7.13 (m, 3H), 6.95 (d, J=2.44 Hz, 1H), 6.78 (d, J=8.24 Hz, 1H), 6.67 (m, 1H), 3.53

(s, 3H), 2.89 (t, J=7.63 Hz, 2H), 2.64 (t, J=7.63 Hz, 2H), 2.47 (s, 3H). MS (ESI+) m/z 379.0 (M+H)$^+$.

Example 134

2-methyl-5-[2-(3-methylphenoxy)phenyl]-1H-pyrrole-3-carboxamide

Example 134 was prepared according to the procedure used for the preparation of Example 121, substituting m-cresol for 4-benzylphenol, to provide the title compound (0.0049 g, 22%). $^1$H NMR (500 MHz, DMSO-d$_6$/D$_2$O) δ 11.20 (s, 1H), 7.68 (m, 1H), 7.22 (m, 3H), 6.92 (m, 3H), 6.78 (m, 2H), 2.44 (s, 3H), 2.26 (s, 3H). MS (ESI+) m/z 306.9 (M+H)$^+$.

Example 135

5-{2-[4-(1H-imidazol-1-yl)phenoxy]phenyl}-2-methyl-1H-pyrrole-3-carboxamide

Example 135 was prepared according to the procedure used for the preparation of Example 121, substituting 4-(1H-imidazol-1-yl)phenol for 4-benzylphenol, to provide the title compound (0.0112 g, 44%). $^1$H NMR (500 MHz, DMSO-d$_6$/D$_2$O) δ 9.49 (s, 1H), 8.11 (s, 1H), 7.82 (s, 1H), 7.75 (dd, J=7.32, 2.14 Hz, 1H), 7.71 (d, J=8.85 Hz, 2H), 7.33 (m, 2H), 7.13 (m, 3H), 6.92 (d, J=2.14 Hz, 1H), 2.43 (s, 3H). MS (ESI+) m/z 359.0 (M+H)$^+$.

Example 136

2-methyl-5-[2-(5,6,7,8-tetrahydronaphthalen-1-yloxy)phenyl]-1H-pyrrole-3-carboxamide Example 136 was prepared according to the procedure used for the preparation of Example 121, substituting 5,6,7,8-tetrahydronaphthalen-1-ol for 4-benzylphenol, to provide the title compound (0.0023 g, 9%). $^1$H NMR (500 MHz, DMSO-d$_6$/D$_2$O) δ 7.66 (dd, J=7.17, 2.29 Hz, 1H), 7.11 (m, 3H), 6.97 (s, 1H), 6.93 (d, J=7.63 Hz, 1H), 6.64 (d, J=7.93 Hz, 1H), 6.60 (m, 1H), 2.76 (m, 2H), 2.61 (m, 2H), 2.47 (s, 3H), 1.70 (m, 4H). MS (ESI+) m/z 347.0 (M+H)$^+$.

Example 137

5-[2-(4-methoxyphenoxy)phenyl]-2-methyl-1H-pyrrole-3-carboxamide

Example 137 was prepared according to the procedure used for the preparation of Example 121, substituting 4-methoxyphenol for 4-benzylphenol, to provide the title compound (0.0071 g, 31%). $^1$H NMR (500 MHz, DMSO-d$_6$/D$_2$O) δ 11.18 (s, 1H), 7.64 (dd, J=7.17, 1.98 Hz, 1H), 7.16 (m, 2H), 6.95 (m, 4H), 6.80 (m, 1H), 3.73 (m, 3H), 2.45 (s, 3H). MS (ESI+) m/z 322.9 (M+H)$^+$.

Example 138

5-[2-(2-benzylphenoxy)phenyl]-2-methyl-1H-pyrrole-3-carboxamide

Example 138 was prepared according to the procedure used for the preparation of Example 121, substituting 2-benzylphenol for 4-benzylphenol, to provide the title compound (0.0062 g, 23%). $^1$H NMR (500 MHz, DMSO-d$_6$/D$_2$O) δ 11.13 (s, 1H), 7.66 (dd, J=7.32, 1.83 Hz, 1H), 7.29 (d, J=7.63 Hz, 1H), 7.18 (m, 9H), 6.93 (d, J=2.75 Hz, 1H), 6.80 (d, J=7.93 Hz, 1H) 6.56 (m, 1H), 3.97 (s, 2H), 2.44 (s, 3H). MS (ESI+) m/z 383.0 (M+H)$^+$.

Example 139

2-methyl-5-[2-(naphthalen-2-yloxy)phenyl]-1H-pyrrole-3-carboxamide

Example 139 was prepared according to the procedure used for the preparation of Example 121, substituting naphthalen-2-ol for 4-benzylphenol, to provide the title compound (0.0069 g, 28%). $^1$H NMR (500 MHz, DMSO-d$_6$/D$_2$O). δ 11.26 (s, 1H), 7.95 (d, J=8.85 Hz, 1H), 7.89 (d, J=7.93 Hz, 1H), 7.74 (m, 2H), 7.45 (m, 2H), 7.36 (dd, J=9.00, 2.29 Hz, 1H), 7.26 (m, 3H), 7.03 (m, 1H), 6.96 (d, J=2.44 Hz, 1H), 2.43 (s, 3H). MS (ESI+) m/z 343.0 (M+H)$^+$.

Example 140

2-methyl-5-[2-(naphthalen-1-yloxy)phenyl]-1H-pyrrole-3-carboxamide

Example 140 was prepared according to the procedure used for the preparation of Example 121, substituting naphthalen-1-ol for 4-benzylphenol, to provide the title compound (0.003.8 g, 16%). $^1$H NMR (500 MHz, DMSO-d$_6$/D$_2$O) δ 8.18 (d, J=7.93 Hz, 1H), 7.98 (d, J=7.93 Hz, 1H), 7.72 (m, 2H), 7.57 (m, 2H), 7.45 (t, J=7.93 Hz, 1H), 7.20 (m, 2H), 7.01 (s, 1H), 6.87 (d, J=7.63 Hz, 1H), 6.79 (d, J=8.24 Hz, 1H), 2.42 (s, 3H). MS (ESI+) m/z 343.0 (M+H)$^+$.

Example 141

5-[2-(4-fluorophenoxy)phenyl]-2-methyl-1H-pyrrole-3-carboxamide

Example 141 was prepared according to the procedure used for the preparation of Example 121, substituting 4-fluorophenol for 4-benzylphenol, to provide the title compound (0.0065 g, 29%). $^1$H NMR (500 MHz, DMSO-d$_6$/D$_2$O) δ 7.67 (m, 1H), 7.20 (m, 4H), 7.02 (m, 2H), 6.92 (s, 1H), 6.89 (m, 1H), 2.44 (s, 3H). MS (ESI+) m/z 310.9 (M+H)$^+$.

Example 142

5-[2-(3-chlorophenoxy)phenyl]-2-methyl-1H-pyrrole-3-carboxamide

Example 142 was prepared according to the procedure used for the preparation of Example 121, substituting 3-chlorophenol for 4-benzylphenol, to provide the title compound (0.0054 g, 23%). $^1$H NMR (500 MHz, DMSO-d$_6$/D$_2$O) δ 11.26 (s, 1H), 7.71 (m, 1H), 7.35 (t, J=8.09 Hz, 1H), 7.28 (m, 2H), 7.12 (d, J=7.93 Hz, 1H), 7.05 (m, 1H), 6.98 (s, 1H), 6.91 (m, 2H), 2.43 (s, 3H). MS (ESI+) m/z 326.9 (M+H)$^+$.

Example 143

5-[2-(4-ethylphenoxy)phenyl]-2-methyl-1H-pyrrole-3-carboxamide

Example 143 was prepared according to the procedure used for the preparation of Example 121, substituting 4-ethylphenol for 4-benzylphenol, to provide the title compound (0.0041 g, 18%). $^1$H NMR (500 MHz, DMSO-d$_6$/D$_2$O) δ

11.19 (s, 1H), 7.67 (dd, J=6.87, 2.29 Hz, 1H), 7.19 (m, 4H), 6.90 (m, 4H), 2.57 (m, 2H), 2.44 (s, 3H), 1.16 (t, J=7.48 Hz, 3H). MS (ESI+) m/z 321.0 (M+H)+.

Example 144

5-[2-(2,3-dihydro-1H-inden-5-yloxy)phenyl]-2-methyl-1H-pyrrole-3-carboxamide

Example 144 was prepared according to the procedure used for the preparation of Example 121, substituting 2,3-dihydro-1H-inden-5-ol for 4-benzylphenol, to provide the title compound (0.007 g, 29%). $^1$H NMR (500 MHz, DMSO-d$_6$/D$_2$O) δ 7.66 (m, 1H), 7.18 (m, 3H), 6.92 (d, J=2.14 Hz, 1H), 6.88 (m, 1H), 6.81 (s, 1H), 6.76 (m, 1H), 2.80 (t, J=7.32 Hz, 4H), 2.44 (s, 3H), 2.01 (m, 2H). MS (ESI+) m/z 333.0 (M+H)+.

Example 145

5-[2-(6-hydroxy-1H-benzimidazol-1-yl)phenyl]-2-methyl-1H-pyrrole-3-carboxamide

A microwave vial containing a magnetic stirbar was charged with Example 115e (0.056 g, 0.2 mmol), 1H-benzo[d]imidazol-6-ol (0.040 g, 0.300 mmol), copper(I) iodide (0.0038 g, 0.02 mmol), tribasic potassium phosphate (0.127 g, 0.600 mmol) and picolinic acid (0.0049 mg, 0.040 mmol), capped, degassed and flushed with nitrogen. Dimethyl sulfoxide (1.6 mL) was added via syringe under a nitrogen atmosphere and the resulting mixture was heated in a microwave reactor at 120° C. for 25 minutes. Dimethyl sulfoxide was removed on high vacuum at 50° C. The residue was slurried in methanol and filtered through a 10 g plug of diatomaceous earth, rinsing with additional methanol. The filtrate was concentrated and then purified by flash chromatography (silica gel, 0 to 20% methanol in dichloromethane to provide a mixture of Examples 145 and 146. Examples 145 and 146 were separated by reverse phase HPLC (C8(2), 5 μM 100 Å column, 10-100% acetonitrile and 0.1% TFA in water). $^1$H NMR (500 MHz, DMSO-d$_6$) δ 11.31 (s, 1H), 9.80 (s, 1H), 9.00 (s, 1H), 7.78 (dd, J=7.93, 1.22 Hz, 1H), 7.68 (m, 2H), 7.58 (m, 1H), 7.51 (td, J=7.55, 1.37 Hz, 1H), 6.93 (dd, J=8.85, 2.14 Hz, 1H), 6.72 (s, 1H), 6.50 (s, 1H), 6.43 (d, J=1.83 Hz, 1H), 5.63 (d, J=2.75 Hz, 1H), 2.34 (s, 3H). LCMS m/z 333.2 (M+H)+.

Example 146

5-[2-(5-hydroxy-1H-benzimidazol-1-yl)phenyl]-2-methyl-1H-pyrrole-3-carboxamide

Example 146 was prepared as described in Example 145. $^1$H NMR (500 MHz, DMSO-d$_6$) δ 11.28 (d, J=1.22 Hz, 1H), 9.91 (s, 1H), 9.20 (s, 1H), 7.77 (dd, J=7.93, 1.22 Hz, 1H), 7.69 (td, J=7.55, 1.37 Hz, 1H), 7.60 (dd, J=7.78, 1.07 Hz, 1H), 7.52 (td, J=7.55, 1.37 Hz, 1H), 7.13 (d, J=2.14 Hz, 1H), 6.98 (d, J=8.85 Hz, 1H), 6.87 (dd, J=9.00, 2.29 Hz, 1H), 6.77 (s, 1H), 6.50 (s, 1H), 5.69 (d, J=2.75 Hz, 1H), 2.33 (s, 3H). LCMS m/z 333.2 (M+H)+.

Example 147

5-(2,6-difluorophenyl)-2-methyl-1H-pyrrole-3-carboxamide

Example 147a tert-butyl 2-acetyl-4-(2,6-difluorophenyl)-4-oxobutanoate

To a suspension of sodium hydride (60% dispersion in mineral oil, 0.204 g, 5.11 mmol) in anhydrous tetrahydrofuran (21 mL) under nitrogen at 0° C. was added dropwise tertbutylacetoacetate (0.7 mL, 4.25 mmol). The mixture was stirred at 5° C. for 20 minutes and treated dropwise with a solution of 2-bromo-1-(2,6-difluorophenyl)ethanone (Syn-Quest 1.0 g, 4.25 mmol) in 2 mL tetrahydrofuran. The mixture was stirred for 24 hours at ambient temperature and partitioned between ethyl acetate and saturated ammonium chloride. The ethyl acetate layer was washed with brine, dried (anhydrous Na$_2$SO$_4$), filtered and concentrated. Purification by chromatography (silica gel, 0-20% ethyl acetate in hexane afforded the title compound (1.07 g, 81%).

Example 147b tert-butyl 5-(2,6-difluorophenyl)-2-methyl-1H-pyrrole-3-carboxylate A mixture of the product from Example 147a (1.0 g, 3.2 mmol) and ammonium acetate (2.47 g, 32 mmol) in acetic acid (10 mL) was heated at 80° C. for 1.5 hours. The mixture was concentrated and the residue was diluted with water and ethyl acetate and treated with 5% aqueous NaHCO$_3$ to a constant pH of 8. The ethyl acetate layer was washed with brine, dried (anhydrous Na$_2$SO$_4$), filtered and concentrated to afford the title compound (1.0 g, 99%).

Example 147c 5-(2,6-difluorophenyl)-2-methyl-1H-pyrrole-3-carboxylic acid

A solution of the product from Example 147b (1.07 g, 3.65 mmol) in dioxane (10 mL) was treated with 4M HCl in dioxane (9.12 mL, 36.5 mmol) and stirred at ambient temperature for 24 hours. The amber solution was concentrated and azeotroped 3×20 mL with toluene to afford the title compound (0.83 g 96%).

Example 147d 5-(2,6-difluorophenyl)-2-methyl-1H-pyrrole-3-carboxamide

A mixture of the product from Example 147c (0.25 g, 1.05 mmol), HOBT (0.24 g 1.58 mmol), 1-ethyl-3-(3-dimethylaminopropyl) carbodiimide (0.30 g, 1.58 mmol) and ammonium chloride (0.28 g, 5.27 mmol) were combined in dimethylformamide (5.3 mL), treated with diisopropylethylamine (1.47 mL, 8.4 mmol) and heated at 40° C. for 24 hours. The mixture was cooled and partitioned between ethyl acetate and water. The organic layer was washed repeatedly with brine, dried (anhydrous Na$_2$SO$_4$), filtered and concentrated. Purification by reverse phase HPLC (C8 (2), 5 μM 100 Å column, 10-100% acetonitrile and 0.1% TFA in water) afforded the title compound (0.120 g, 48%)

$^1$H NMR (300 MHz, DMSO-$d_6$) δ 9.02 (s, 1H) 7.07-7.21 (m, 1H) 6.83-7.05 (m, 3H) 5.72 (s, 2H) 2.64 (s, 3H). MS (ESI+) m/z 237 (M+H)$^+$.

Example 148

5-(2-benzylphenyl)-2-methyl-1H-pyrrole-3-carboxamide

Example 115e (0.028 g, 0.1 mmol), palladium(II) acetate (0.0022 g, 0.01 mmol) and 2-dicyclohexylphosphino-2',6'-dimethoxybiphenyl (0.0082 g, 0.020 mmol) were combined in a microwave vial equipped with a magnetic stirbar. The vial was capped and purged with nitrogen. Tetrahydrofuran (0.2 mL) was added via syringe under nitrogen and the resulting mixture was stirred for 10 minutes. Benzylzinc(II) bromide (0.800 mL, 0.400 mmol) was added via syringe under nitrogen and the mixture was stirred at ambient temperature overnight. The reaction mixture was then partitioned between ethyl acetate and water, and the organic phase was washed with brine, dried (anhydrous MgSO$_4$), filtered through a plug of diatomaceous earth and concentrated. The residue was purified by reverse phase HPLC (C8(2), 5 μM 100 Å column, 10-100% acetonitrile and 0.1% TFA in water) to provide the title compound. $^1$H NMR (300 MHz, DMSO-$d_6$) δ 11.11 (s, 1H), 7.35 (dd, J=7.34, 1.39 Hz, 1H), 7.21 (m, 5H), 7.07 (m, 4H), 6.59 (d, J=2.78 Hz, 1H), 6.55 (s, 1H), 4.14 (s, 2H), 2.45 (s, 3H). MS (ESI+) m/z 291.0 (M+H)$^+$.

Example 149

2-methyl-5-(3,4,5-trimethoxyphenyl)-1H-pyrrole-3-carboxamide

Example 149a 2-methyl-1H-pyrrole-3-carboxylic acid

Lithium hydroxide (1.563 g, 65.3 mmol) in water (20 mL) was added into ethyl 2-methyl-1H-pyrrole-3-carboxylate (2.0 g, 13.06 mmol) in dioxane (20 mL). The reaction mixture was heated under reflux for 4 hours, cooled, and partitioned with ethyl acetate and 1 M HCl. The organic layer was washed with brine, dried with anhydrous sodium sulfate, filtered and evaporated to give the title compound (1.513 g, 93%).

Example 149b 2-methyl-1H-pyrrole-3-carboxamide

Example 149a (0.86 g, 6.87 mmol), O-(7-azabenzotriazol-1-yl)-N,N,N',N'-tetramethyluronium hexafluorophosphate (HATU, 3.14 g, 8.25 mmol), N,N-diisopropylethylamine (3.60 mL, 20.62 mmol) and 0.5 M ammonia in dioxane (27.5 mL, 13.8 mmol) were combined in dimethylformamide (15 mL). The reaction mixture was stirred at ambient temperature for 1 hour and concentrated. The residue was purified by flash chromatography (silica gel, 5-10% methanol in dichloromethane) to afford the title compound (628 mg, 74%).

Example 149c 5-iodo-2-methyl-1H-pyrrole-3-carboxamide

Example 149b (470 mg, 3.79 mmol) in tetrahydrofuran (10 mL) was cooled to −78° C. and N-iodosuccinimide (852 mg, 3.79 mmol) in tetrahydrofuran (5 mL) was added. The reaction mixture was stirred at this temperature for 30 minutes and concentrated at 0° C. The residue was purified by flash chromatography (silica gel, 5% methanol in dichloromethane) to afford the title compound (670 mg, 71%).

Example 149d 2-methyl-5-(3,4,5-trimethoxyphenyl)-1H-pyrrole-3-carboxamide

Example 149c (100 mg, 0.400 mmol), 3,4,5-trimethoxyphenylboronic acid (93 mg, 0.440 mmol), bis(triphenylphosphine)palladium(II) chloride (14.04 mg, 0.020 mmol) and 2 M aqueous sodium carbonate (0.60 mL, 1.20 mmol) were combined in 1,2-dimethoxyethane (1 mL)/ethanol (1 mL). The reaction mixture was purged with nitrogen for 5 minutes and heated by microwave at 100° C. for 30 minutes. The reaction mixture was partitioned with ethyl acetate and water. The organic layer was washed with brine, dried with anhydrous sodium sulfate, filtered and evaporated. The residue was triturated with methanol/dichloromethane (5%) to afford the title compound (13 mg, 11%). $^1$H NMR (300 MHz, DMSO-$d_6$) δ 11.23 (s, 1H) 7.06 (s, 1H) 6.81-6.91 (m, 3H) 6.59 (s, 1H) 3.82 (s, 6H) 3.65 (s, 3H) 2.47 (s, 3H). MS (ESI+) m/z 291 (M+H)$^+$.

Example 150

5-(biphenyl-3-yl)-2-methyl-1H-pyrrole-3-carboxamide

Example 150a tert-butyl 2-acetyl-4-(3-bromophenyl)-4-oxobutanoate

Example 150a was prepared according to the procedure used for the preparation of Example 1a, substituting 2-bromo-1-(3-bromophenyl)ethanone for 2-bromo-2'-nitroacetophenone. Purification by flash chromatography (silica gel, 10-20% ethyl acetate in hexane) afforded the title compound (21.4 g, 86%).

Example 150b tert-butyl 5-(3-bromophenyl)-2-methyl-1H-pyrrole-3-carboxylate

Example 150b was prepared according to the procedure used for the preparation of Example 1b, substituting Example 150a for Example 1a, to provide the title compound (18.3 g, 91%).

Example 150c 5-(3-bromophenyl)-2-methyl-1H-pyrrole-3-carboxylic acid

To Example 150b (9.41 g, 28 mmol) was added 4 M hydrogen chloride in dioxane (80 mL, 320 mmol). The reaction mixture was stirred at ambient temperature for 28 hours and concentrated. The residue was azeotroped with toluene twice and triturated with dichloromethane/hexane (1:2) to provide the title compound (7.19 g, 92%).

Example 150d

5-(3-bromophenyl)-2-methyl-1H-pyrrole-3-carboxamide

Example 150d was prepared according to the procedure used for the preparation of Example 1d, substituting Example 150c for Example 1c. Purification by trituration (dichloromethane)) afforded the title compound (2.12 g, 76%).

Example 150e

5-(biphenyl-3-yl)-2-methyl-1H-pyrrole-3-carboxamide

Example 150d (30 mg, 0.10 mmol), phenylboronic acid (15 mg, 0.13 mmol), cesium carbonate (70 mg, 0.21 mmol) and Silicat resin (40 mg, 0.01 mmol) were combined in ethanol (2 mL) and water (0.2 mL). The mixture was heated by at 120° C. for 30 minutes. The crude material was filtered, and the eluant was concentrated and purified by reverse phase HPLC (C8(2), 5 μM 100 Å column, 10-100% acetonitrile and 0.1% TFA in water) to afford the title compound (5.4 mg, 18%). $^1$H NMR (400 MHz, DMSO-$d_6$) δ 11.50 (s, 1H), 7.89 (s, 1H), 7.67-7.79 (m, 2H), 7.56-7.65 (m, 1H), 7.44-7.55 (m, 4H), 7.35-7.43 (m, 1H), 6.99 (d, J=2.7 Hz, 1H), 2.49 (s, 3H). MS (ESI+) m/z 277 (M+H)$^+$.

Example 151

5-(3'-methoxybiphenyl-3-yl)-2-methyl-1H-pyrrole-3-carboxamide

Example 151 was prepared according to the procedure used for the preparation of Example 150e, substituting 3-methoxyphenylboronic acid for phenylboronic acid, to provide the title compound (7.2 mg, 22%). $^1$H NMR (400 MHz, DMSO-$d_6$) δ 7.88 (s, 1H), 7.52-7.63 (m, 1H), 7.44-7.51 (m, 2H), 7.43 (t, J=5.7 Hz, 1H), 7.30 (d, J=8.1 Hz, 1H), 7.19-7.28 (m, 1H), 6.86-7.04 (m, 2H), 3.85 (s, 3H), 2.49 (s, 3H). MS (ESI+) m/z 307 (M+H)$^+$.

Example 152

2-methyl-5-[3-(thiophen-3-yl)phenyl]-1H-pyrrole-3-carboxamide

Example 152 was prepared according to the procedure used for the preparation of Example 150e, substituting 3-thiophene boronic acid for phenylboronic acid, to provide the title compound (3.6 mg, 12%). $^1$H NMR (400 MHz, DMSO-$d_6$) δ 11.46 (s, 1H), 7.93 (d, J=1.5 Hz, 1H), 7.87 (dd, J=2.9, 1.3 Hz, 1H), 7.67 (dd, J=5.0, 2.9 Hz, 1H), 7.61 (dd, J=5.0, 1.3 Hz, 1H), 7.47-7.54 (m, 2H), 7.41 (t, J=7.7 Hz, 1H), 2.49 (s, 3H). MS (ESI+) m/z 283 (M+H)$^+$.

Example 153

5-(2'-acetylbiphenyl-3-yl)-2-methyl-1H-pyrrole-3-carboxamide

Example 153 was prepared according to the procedure used for the preparation of Example 150e, substituting 2-acetylphenylboronic acid for phenylboronic acid, to provide the title compound (3.4 mg, 10%). $^1$H NMR (400 MHz, DMSO-$d_6$) δ 11.46 (s, 1H), 7.63 (t, J=6.0 Hz, 2H), 7.60 (d, J=7.5 Hz, 1H), 7.54 (dd, J=3.7, 1.4 Hz, 1H), 7.51 (dd, J=7.9, 1.4 Hz, 1H), 7.45-7.49 (m, 1H), 7.43 (d, J=7.7 Hz, 1H), 7.07 (d, J=7.7 Hz, 1H), 6.94 (d, J=2.6 Hz, 1H), 2.47 (s, 3H), 2.18 (s, 3H). MS (ESI+) m/z 319 (M+H)$^+$.

Example 154

2-methyl-5-[3-(pyridin-3-yl)phenyl]-1H-pyrrole-3-carboxamide

Example 154 was prepared according to the procedure used for the preparation of Example 150e, substituting 3-pyridine boronic acid for phenylboronic acid, to provide the title compound (2.9 mg, 10%). $^1$H NMR (400 MHz, DMSO-$d_6$) δ 11.53 (s, 1H), 9.12 (d, J=1.9 Hz, 1H), 8.77 (dd, J=5.3, 1.2 Hz, 1H), 8.60 (d, J=8.2 Hz, 1H), 7.99 (s, 1H), 7.91 (dd, J=8.1, 5.3 Hz, 1H), 7.70 (d, J=7.5 Hz, 1H), 7.50-7.63 (m, 2H), 7.02 (d, J=2.5 Hz, 1H), 2.50 (s, 3H). MS (ESI+) m/z 278 (M+H)$^+$.

Example 155

2-methyl-5-[3-(1H-pyrazol-4-yl)phenyl]-1H-pyrrole-3-carboxamide

Example 155 was prepared according to the procedure used for the preparation of Example 150e, substituting 4-(4,4,5,5-tetramethyl-1,3,2-dioxaborolan-2-yl)-1H-pyrazole for phenylboronic acid, to provide the title compound (1.4 mg, 5%). $^1$H NMR (400 MHz, DMSO-$d_6$) δ 11.41 (s, 1H), 8.08 (s, 2H), 7.83 (s, 1H), 7.22-7.60 (m, 3H), 6.94 (d, J=1.5 Hz, 1H), 2.49 (s, 3H). MS (ESI+) m/z 267 (M+H)$^+$.

Example 156

2-methyl-5-[3-(1-methyl-1H-indol-5-yl)phenyl]-1H-pyrrole-3-carboxamide

Example 156 was prepared according to the procedure used for the preparation of Example 150e, substituting 1-methyl-5-(4,4,5,5-tetramethyl-1,3,2-dioxaborolan-2-yl)-1H-indole for phenylboronic acid, to provide the title compound (13.6 mg, 38%). $^1$H NMR (400 MHz, DMSO-$d_6$) δ 11.47 (d, J=15.7 Hz, 1H), 7.88 (t, J=18.5 Hz, 2H), 7.53 (d, J=8.9 Hz, 2H), 7.50 (t, J=7.3 Hz, 2H), 7.40-7.47 (m, 1H), 7.36 (s, 1H), 6.97 (t, J=5.2 Hz, 1H), 3.83 (s, 3H), 2.46-2.51 (m, 3H). MS (ESI+) m/z 330 (M+H)$^+$.

Example 157

2-methyl-5-{3-[(E)-2-phenylethenyl]phenyl}-1H-pyrrole-3-carboxamide

Example 157 was prepared according to the procedure used for the preparation of Example 150e, substituting (E)-4,4,5,5-tetramethyl-2-styryl-1,3,2-dioxaborolane for phenylboronic acid, to provide the title compound (8.1 mg, 25%). $^1$H NMR (400 MHz, DMSO-$d_6$) δ 11.46 (s, 1H), 7.84 (s, 1H), 7.59 (dd, J=29.3, 4.5 Hz, 2H), 7.47-7.51 (m, 1H), 7.36-7.46 (m, 5H), 7.25-7.34 (m, 3H), 6.95 (d, J=2.6 Hz, 1H), 2.49 (s, 3H). MS (ESI+) m/z 303 (M+H)$^+$.

Example 158

2-methyl-5-{3'-[(4-methylpiperazin-1-yl)methyl]biphenyl-3-yl}-1H-pyrrole-3-carboxamide Example 158 was prepared according to the procedure used for the preparation of Example 150e, substituting 1-methyl-4-(3-(4,4,5,5-tetramethyl-1,3,2-dioxaborolan-2-yl)benzyl)piperazine for phenylboronic acid, to provide the title compound (11 mg, 17%) as a trifluoroacetic acid salt. $^1$H NMR (400 MHz, DMSO-$d_6$) δ 11.50 (s, 1H), 7.88 (s, 1H), 7.76 (d, J=7.4 Hz, 2H), 7.51-7.63 (m, 2H), 7.47 (dd, J=17.8, 6.3 Hz, 3H), 6.98 (d, J=2.5 Hz, 1H), 4.05 (s, 2H), 3.32 (s, 4H), 2.82 (s, 4H), 2.49 (s, 3H). MS (ESI+) m/z 389 (M+H)$^+$.

Example 159

5-(4'-{[2-(dimethylamino)ethyl]carbamoyl}biphenyl-3-yl)-2-methyl-1H-pyrrole-3-carboxamide Example 159 was prepared according to the procedure used for the preparation of Example 150e, substituting 4-(2-(dimethylamino)ethylcarbamoyl)phenylboronic acid for phenylboronic acid, to provide the title compound (9.5 mg, 18%) as a trifluoroacetic acid salt. $^1$H NMR (400 MHz, DMSO-$d_6$) δ 11.52 (s, 1H), 7.97 (t, J=9.7 Hz, 3H), 7.88 (d, J=8.5 Hz, 2H), 7.62 (d, J=7.5 Hz, 1H), 7.46-7.58 (m, 2H), 6.99 (d, J=2.7 Hz, 1H), 3.66 (t, J=5.9 Hz, 1H), 3.30 (t, J=6.0 Hz, 2H), 2.87 (s, 6H), 2.50 (s, 3H). MS (ESI+) m/z 391 (M+H)$^+$.

Example 160

5-[3-(1,3-benzodioxol-5-yloxy)phenyl]-2-methyl-1H-pyrrole-3-carboxamide

Example 150d (40 mg, 0.143 mmol), benzo[d][1,3]dioxol-5-ol (240 mg, 0.859 mmol), copper(I) iodide (27.3 mg, 0.143 mmol), picolinic acid (21.2 mg, 0.172 mmol) and tripotassium phosphate (91.3 mg, 0.430 mmol) were combined in DMSO (3 mL). The reaction mixture was heated by microwave at 150° C. for 45 minutes. The crude material was filtered, and the eluant was concentrated and purified by reverse phase HPLC (C8(2), 5 μM 100 Å column, 10-100% acetonitrile and 0.1% TFA in water) to afford the title compound (0.0237 g, 49%). $^1$H NMR (400 MHz, DMSO-$d_6$) δ 7.30-7.37 (m, 2H), 7.20 (s, 1H), 6.92 (d, J=8.54 Hz, 1H), 6.87 (d, J=2.75 Hz, 1H), 6.71-6.75 (m, 2H), 6.51 (dd, J=8.54, 2.44 Hz, 1H), 6.03 (s, 2H), 2.45 (s, 3H). MS (ESI+) m/z 337 (M+H)$^+$.

Example 161

5-(5-amino-2-phenoxyphenyl)-2-methyl-1H-pyrrole-3-carboxamide

Example 161a 5-(2-fluoro-5-nitrophenyl)-2-methyl-1H-pyrrole-3-carboxamide

Example 161a was prepared according to the procedure used for the preparation of Example 92e, substituting Example 149c for Example 92d and 2-fluoro-5-nitrophenylboronic acid for 3,5-dimethylisoxazol-4-ylboronic acid, to provide the title compound (0.059 g, 45%).

Example 161b 2-methyl-5-(5-nitro-2-phenoxyphenyl)-1H-pyrrole-3-carboxamide

Example 161b was prepared according to the procedure used for the preparation of Example 91c, substituting Example 161a for Example 91b, to provide the title compound (0.060 g, 80%).

Example 161c 5-(5-amino-2-phenoxyphenyl)-2-methyl-1H-pyrrole-3-carboxamide

Example 161c was prepared according to the procedure used for the preparation of Example 1e, substituting Example 161b for Example 1d, to provide the title compound (0.0533 g, 54%). $^1$H NMR (300 MHz, DMSO-$d_6$) δ 11.15 (s, 1H), 7.32 (m, 3H), 7.06 (m, 3H), 6.92 (m, 5H), 6.58 (s, 2H), 2.42 (s, 3H). MS (ESI+) m/z 308.3 (M+H)$^+$.

Example 162

2-methyl-5-{5-[(methylsulfonyl)amino]-2-phenoxyphenyl}-1H-pyrrole-3-carboxamide

Example 161c (0.031 g, 0.1 mmol) in dichloromethane (1.0 mL) was treated sequentially with methanesulfonyl chloride (0.017 mL, 0.220 mmol) and triethylamine (0.035 mL, 0.250 mmol), stirred at ambient temperature for 1 hour and then concentrated to dryness. The residue was dissolved in 1,4-dioxane (1.0 mL), treated with 1 N aqueous sodium hydroxide solution (1.0 mL) and heated at 50° C. for 1 hour. The reaction mixture was then cooled to ambient temperature and neutralized with 2 N aqueous hydrochloric acid solution. The resulting mixture was partitioned between ethyl acetate and water, and the organic layer was washed with brine, dried (anhydrous MgSO$_4$), filtered and concentrated. The residue was purified by flash chromatography (silica gel, 0 to 10% methanol in dichloromethane). The material was further purified by reverse phase HPLC (C8(2), 5 μM 100 Å column, 10-100% acetonitrile and 0.1% TFA in water) to provide the title compound (0.0173 g, 45%). $^1$H NMR (300 MHz, DMSO-$d_6$) δ 11.14 (s, 1H), 9.62 (s, 1H), 7.46 (d, J=2.78 Hz, 1H), 7.33 (m, 2H), 7.05 (m, 3H), 6.95 (m, 3H), 6.86 (d, J=2.78 Hz, 1H), 6.55 (s, 1H), 3.02 (s, 3H), 2.43 (s, 3H). LCMS m/z 386.2 (M+H)$^+$.

Example 163

5-(1H-benzimidazol-4-yl)-2-methyl-1H-pyrrole-3-carboxamide

A 5 mL microwave reaction vessel equipped with a stirbar was charged with Example 149c (0.055 g, 0.220 mmol), 1H-benzo[d]imidazol-4-ylboronic acid (0.062 g, 0.383 mmol), 2 M aqueous sodium carbonate (1.6 mL, 3.20 mmol) and bis(triphenylphosphine)palladium(II) dichloride (0.010 g, 0.014 mmol) in ethanol (1.4 mL)/DME (1.4 mL) and sealed. The mixture was heated to 120° C. for 30 minutes in a Biotage Initiator 2 monomode microwave reactor, and then cooled to ambient temperature. The mixture was shaken in a separatory funnel with 75 mL ethyl acetate and 50 mL water. The organics were dried over anhydrous sodium sulfate, filtered, and concentrated. The residue was purified by reverse phase HPLC (C18, 0-100% CH$_3$CN/10 mM ammonium acetate in water) to afford the title compound. $^1$H NMR (300 MHz, CDCl$_3$) δ ppm 7.52 (m, 1H), 7.31 (m, 2H), 6.91 (s, 1H), 6.85 (s, 1H), 2.61 (s, 3H). MS (DCI+) m/z 241.1 (M+H)$^+$, 258.2 (M+NH$_4$)$^+$.

Example 164

5-(1H-indol-7-yl)-2-methyl-1H-pyrrole-3-carboxamide

Example 164 was prepared according to the procedure used for the preparation of Example 163, substituting 1H-indol-7-ylboronic acid for 1H-benzo[d]imidazol-4-ylboronic acid, to provide the title compound. $^1$H NMR (300 MHz, CDCl$_3$) δ ppm 7.60 (m 1H), 7.19-7.16 (m, 3H), 6.91 (s, 1H), 6.64 (m, 1H), 2.66 (s, 3H). MS (DCI+) m/z 240.1 (M+H)$^+$, 257.1 (M+NH$_4$)$^+$.

Example 165 ethyl [4-(benzyloxy)-3-(4-carbamoyl-5-methyl-1H-pyrrol-2-yl)phenyl]acetate

Example 165a ethyl 2-(3-bromo-4-hydroxyphenyl)acetate

Ethyl 2-(4-hydroxyphenyl)acetate (2.70 g, 15 mmol) in acetic acid (20 mL) was treated with a solution of bromine (0.773 mL, 15.00 mmol) in acetic acid (15 mL) over 15 minutes. The reaction mixture was stirred at ambient temperature for 30 minutes and concentrated. The residue was purified by flash chromatography (silica gel, 10-20% ethyl acetate in hexane) to afford the title compound (3.66 g, 94%).

Example 165b ethyl 2-(4-(benzyloxy)-3-bromophenyl)acetate

Example 165a (3.65 g, 14.1 mmol), (bromomethyl)benzene (2.01 mL, 16.9 mmol), and potassium carbonate (5.84 g, 42.3 mmol) were combined in ethanol (100 mL). The reaction mixture was heated under reflux for 2 hours and concentrated. The residue was partitioned with ethyl acetate and water. The organic layer was washed with brine, dried with anhydrous sodium sulfate, filtered and evaporated. The residue was purified by flash chromatography (silica gel, 0-20% ethyl acetate in hexane) to afford the title compound (4.84 g, 98%).

Example 165c ethyl 2-(4-(benzyloxy)-3-(4,4,5,5-tetramethyl-1,3,2-dioxaborolan-2-yl)phenyl)acetate The product from Example 165b (1.048 g, 3.0 mmol), 4,4,4',4',5,5,5',5'-octamethyl-2,2'-bi(1,3,2-dioxaborolane) (0.990 g, 3.90 mmol), PdCl$_2$(dppf) (0.220 g, 0.30 mmol) and potassium acetate (0.883 g, 9.0 mmol) were combined in dimethylformamide (15 mL). The reaction mixture was purged with nitrogen for 30 minutes and heated at 85° C. for 20 hours. The reaction mixture was partitioned with ethyl acetate and water. The organic layer was washed with brine twice, dried with anhydrous sodium sulfate, filtered and evaporated to give the title compound which was used directly without purification.

Example 165d ethyl [4-(benzyloxy)-3-(4-carbamoyl-5-methyl-1H-pyrrol-2-yl)phenyl]acetate Example 149c (0.750 g, 3.00 mmol), Example 165c (1.189 g, 3.00 mmol), Pd$_2$(dba)$_3$ (0.069 g, 0.075 mmol), 1,3,5,7-tetramethyl-6-phenyl-2,4,8-trioxa-6-phosphaadamante (0.044 g, 0.150 mmol) and tripotassium phosphate (1.910 g, 9.00 mmol) were combined in dioxane (12 mL)/water (3 mL). The reaction mixture was purged with nitrogen for 30 minutes and heated at 60° C. for 6 hours. The reaction mixture was partitioned with ethyl acetate and water. The organic layer was washed with brine twice, dried with anhydrous sodium sulfate, filtered and evaporated. The residue was purified by flash chromatography (silica gel, 0-2% methanol in dichloromethane) to afford the title compound (318 mg, 27%). $^1$H NMR (300 MHz, DMSO-d$_6$) δ 10.91 (s, 1H) 7.46-7.51 (m, 2H) 7.26-7.43 (m, 4H) 6.97-7.05 (m, 3H) 6.95 (d, J=2.78 Hz, 1H) 6.57 (s, 1H) 5.26 (s, 2H) 4.07 (q, J=7.14 Hz, 2H) 3.57 (s, 2H) 2.44 (s, 3H) 1.18 (t, J=7.14 Hz, 3H). MS (ESI+) m/z 393 (M+H)$^+$.

Example 166

[4-(benzyloxy)-3-(4-carbamoyl-5-methyl-1H-pyrrol-2-yl)phenyl]acetic acid

Example 165d (305 mg, 0.777 mmol) and 1 M aqueous sodium hydroxide (2.33 mL, 2.33 mmol) were combined in tetrahydrofuran (10 mL)/water (5 mL). The reaction mixture was heated under reflux for 3 hours, cooled to ambient temperature, and partitioned with ethyl acetate and water. The aqueous layer was acidified by 1M HCl and the resulting solid was filtered, washed with water and dried to provide the title compound (267 mg, 94%). $^1$H NMR (300 MHz, DMSO-d$_6$) δ 10.90 (s, 1H) 7.46-7.51 (m, 2H) 7.26-7.43 (m, 4H) 6.96-7.05 (m, 3H) 6.95 (d, J=2.71 Hz, 1H) 6.54 (s, 1H) 5.26 (s, 2H) 3.48 (s, 2H) 2.44 (s, 3H). MS (ESI+) m/z 365 (M+H)$^+$.

Example 167

5-[2-(benzyloxy)-5-(2-hydroxyethyl)phenyl]-2-methyl-1H-pyrrole-3-carboxamide

Example 166 (51.0 mg, 0.14 mmol) in tetrahydrofuran (2 mL) was treated with 1.0 M borane tetrahydrofuran complex (0.280 mL, 0.280 mmol). The reaction mixture was stirred at ambient temperature for 20 hours, treated with methanol (2 mL) and heated at 50° C. for 30 minutes. The reaction mixture was concentrated and the residue was purified by flash chromatography (silica gel, 0-4% methanol in dichloromethane) to afford the title compound (32 mg, 65%). $^1$H NMR (300 MHz, DMSO-d$_6$) δ 10.87 (s, 1H) 7.43-7.53 (m, 2H) 7.25-7.41 (m, 4H) 6.87-7.04 (m, 4H) 6.55 (s, 1H) 5.23

(s, 2H) 4.60 (t, J=5.09 Hz, 1H) 3.52-3.65 (m, 2H) 2.66 (t, J=7.29 Hz, 2H) 2.44 (s, 3H). MS (ESI+) m/z 351 (M+H)+.

Example 168

5-[2-(2,4-difluorophenoxy)-5-sulfamoylphenyl]-2-methyl-1H-pyrrole-3-carboxamide

Example 168a 4-(2,4-difluorophenoxy)-3-nitrobenzenesulfonamide

A solution of 2,4-difluorophenol (5.39 g, 41.4 mmol) in dimethylformamide (34.5 mL) at 10° C. under nitrogen was treated portionwise with sodium hydride (60%, 1.657 g, 41.4 mmol), stirred for 15 minutes and then treated portionwise with 4-fluoro-3-nitrobenzenesulfonamide (2.28 g, 10.36 mmol). The solution was stirred at ambient temperature for 1.5 hours, diluted into ethyl acetate and carefully quenched with 0.5 M HCl to a constant pH of 6. The organic layer was washed with brine, dried (anhydrous MgSO$_4$), filtered and concentrated. The residue was triturated in 3:1 hexane/ethyl acetate and the title compound was collected by filtration (3.24 g, 95%).

Example 168b 3-amino-4-(2,4-difluorophenoxy)benzenesulfonamide

The product from Example 168a (3.24 g, 9.81 mmol), iron powder (2.74 g, 49.1 mmol), and ammonium hydrochloride (0.787 g, 14.72 mmol) were combined in the solvent mixture of tetrahydrofuran (21 mL), ethanol (21 mL) and water (7 mL) and heated at 95° C. with vigorous stirring for 3 hours. The mixture was cooled and filtered through a plug of Celite to remove solids. The plug was rinsed repeatedly with methanol and tetrahydrofuran. The filtrate was concentrated and the residue partitioned between ethyl acetate and water. The ethyl acetate layer was washed with brine, dried (anhydrous Na$_2$SO$_4$), filtered and concentrated to afford the title compound (2.81 g, 95%).

Example 168c 4-(2,4-difluorophenoxy)-3-iodobenzenesulfonamide

A solution of the product from Example 168b (2.8 g, 9.32 mmol) in dioxane (20 mL) at 0° C. was treated with concentrated hydrochloric acid (40 mL, 9.32 mmol), stirred for 15 minutes at 0° C., and treated with a solution of sodium nitrite (0.772 g, 11.19 mmol) in water (10 mL). The mixture was stirred for 1 hour at 0° C., treated with a solution of potassium iodide (3.10 g, 18.65 mmol) in water (10 mL), stirred for 1 hour and partitioned between ethyl acetate and water. The organic layer was washed with saturated sodium thiosulfate, water, brine, dried (anhydrous MgSO$_4$), filtered and concentrated. The residue was purified by flash chromatography (silica gel, 0-60% ethyl acetate in hexane) afforded the title compound (2.24 g, 58%).

Example 168d ethyl 2-methyl-5-(4,4,5,5-tetramethyl-1,3,2-dioxaborolan-2-yl)-1H-pyrrole-3-carboxylate A mixture of ethyl 2-methyl-1H-pyrrole-3-carboxylate (3.06 g, 20.0 mmol), 4,4,4',4',5,5,5',5'-octamethyl-2,2'-bi(1,3,2-dioxaborolane) (2.54 g, 10 mmol), (1,5-cyclooctadiene)(methoxy)iridium(I) dimer (0.099 g, 0.15 mmol) and 4,4'-di-tert-butyl-2,2'-bipyridine (0.081 g, 0.30 mmol) in hexane (100 mL) was sparged with argon for 15 minutes, stirred for 24 hours under nitrogen and partitioned between ethyl acetate and water. The organic layer was washed with brine, dried (anhydrous Na$_2$SO$_4$), treated with mercaptopropyl silica (Aldrich catalog 538086, approximately 1.0 g) for 30 minutes and filtered. The filtrate was concentrated to afford the title compound (5.55 g, 98%).

Example 168e ethyl 5-(2-(2,4-difluorophenoxy)-5-sulfamoylphenyl)-2-methyl-1H-pyrrole-3-carboxylate The product from Example 168d (0.167 g, 0.6 mmol), the product from Example 168c (0.206 g, 0.5 mmol), tris(dibenzylideneacetone)dipalladium(0) (0.014 g, 0.015 mmol), 1,3,5,7-tetramethyl-6-phenyl-2,4,8-trioxa-6-phosphaadamantane (PA-Ph, CAS 97739-46-3, 0.015 g, 0.05 mmol) and potassium phosphate tribasic (0.318 g, 1.5 mmol) were combined and sparged with argon for 30 minutes. Meanwhile a solution of dioxane (2.3 mL) and water (0.57 mL) was sparged with nitrogen for 30 minutes and transferred into the solids under argon. The mixture was stirred at 60° C. for 3 hours, cooled, partitioned between ethyl acetate and water and filtered through a plug of Celite. The filtrate layers were separated. The ethyl acetate layer was washed with saturated brine, dried (anhydrous Na$_2$SO$_4$), treated with mercaptopropyl silica (Aldrich catalog 538086, approximately 1.0 g) for thirty minutes, filtered and concentrated. Purification by trituration (10% ethyl acetate in hexane) afforded the title compound (0.177 g, 81%).

Example 168f 5-(2-(2,4-difluorophenoxy)-5-sulfamoylphenyl)-2-methyl-1H-pyrrole-3-carboxylic acid The product from Example 168e (0.177 g, 0.406 mmol) and lithium hydroxide (0.097 g, 4.06 mmol) were combined in water (2 mL), ethanol (2 mL) and dioxane (2 mL), heated at 90° C. for 5 hours, cooled to ambient temperature, and concentrated. The residue was partitioned with ethyl acetate and water and treated with 1M HCl to a constant pH of 2. The organic layer was washed with brine, dried (anhydrous Na$_2$SO$_4$), filtered and concentrated to afford the title compound (0.15 g, 91%).

Example 168g

5-[2-(2,4-difluorophenoxy)-5-sulfamoylphenyl]-2-methyl-1H-pyrrole-3-carboxamide

Example 168g was prepared according to the procedure of Example 147d substituting the product of Example 168f for the product of Example 147c. Purification by trituration in dichloromethane afforded the title compound (0.114 g, 82%). $^1$H NMR (300 MHz, DMSO-d$_6$) δ 11.41 (s, 1H) 8.14 (d, J=2.03 Hz, 1H) 7.48-7.59 (m, 2H) 7.35-7.45 (m, 1H) 7.27 (s, 2H) 7.16-7.24 (m, 2H) 7.11 (d, J=2.03 Hz, 1H) 6.82 (d, J=8.48 Hz, 1H) 6.58 (s, 1H) 2.51 (s, 3H). MS (ESI+) m/z 408 (M+H)+.

Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623) (100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [M−H)$^-$] and (S,Z)—N,N'-(2,2'-(ethane-1,2-diylbis(oxy))bis(ethane-2,1-diyl))bis (2-((6S,Z)-4-(4-chlorophenyl)-2,3,9-trimethyl-6H-thieno[3,2-f][1,2,4]triazolo[4,3-a][1,4]diazepin-6-yl)acetamide) bis (2,2,2-trifluoroacetate) (3.0 mg, 1.5%); ESI-MS m/z=913.2 [(M+H)$^+$]; 911.0 [M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via a 3-fold serial dilution from 2.5 mM to 42 nM. Compounds were then diluted 6:100 in assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) to yield 3× working solutions. Six microliters (μL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve μL of this solution were added to the assay plate to reach a final volume of 18 μL. The final concentration of 1× assay buffer contains 2% DMSO, 50 μM-0.85 nM compound, 8 nM His-tagged bromodomain, 1 nM Europium-conjugated anti-His-tag antibody and 100 nM or 30 nM probe (for BDI or BDII, respectively). After a one-hour incubation at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}s$. Inhibition constants ($K_i$) were calculated from the $IC_{50}s$, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37° C. and an atmosphere of 5% $CO_2$. For compound testing, MX-1 cells were plated in 96-well black bottom plates at a density of 5000 cells/well in 90 μL of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Example # | TR-FRET Binding $K_i$: BRD4 (BDI_K57-E168) (μM) | TR-FRET Binding $K_i$: BRD4 (BDII_E352-M457) (μM) | Cellular proliferation: $EC_{50}$ (μM) |
|---|---|---|---|
| 1 | 2.54 | 6.21 | ND |
| 2 | 2.92 | 21.5 | ND |
| 3 | 2.33 | 7.2 | ND |
| 4 | 5.19 | 4.44 | ND |
| 5 | 8.09 | 6.43 | ND |
| 6 | 3.16 | 5.01 | ND |
| 7 | 1.63 | 6.89 | ND |
| 8 | 2.68 | 3.72 | ND |
| 9 | 2.88 | 3.14 | ND |
| 10 | 3.47 | 5.57 | ND |
| 11 | 2.87 | 2.51 | ND |
| 12 | 0.935 | 3.9 | 3.44 |
| 13 | 0.774 | 4.54 | 3.3 |
| 14 | 0.209 | 0.722 | 0.465 |
| 15 | 2.58 | 2.31 | ND |
| 16 | 1.18 | 2.02 | ND |
| 17 | 0.248 | 1.87 | 1.5 |
| 18 | 0.183 | 2.34 | 2.85 |
| 19 | 0.131 | 1.83 | 2.36 |
| 20 | 1.19 | 3.29 | ND |
| 21 | 9.69 | 21.5 | ND |
| 22 | 2.98 | 3.66 | ND |
| 23 | 3.52 | 3.53 | ND |
| 24 | 1.06 | 1.19 | ND |
| 25 | 1.26 | 2.16 | ND |
| 26 | 0.86 | 7.53 | ND |
| 27 | 0.384 | 1.48 | 1.3 |
| 28 | 9.45 | 13.6 | ND |
| 29 | 2.77 | 4.41 | ND |
| 30 | 3.06 | 3.48 | ND |
| 31 | 1.4 | 6.23 | ND |
| 32 | 5.17 | 10.3 | ND |
| 33 | 9.63 | 13.1 | ND |
| 34 | 1.4 | 3.45 | ND |
| 35 | 2.7 | 3.26 | ND |
| 36 | 0.521 | 1.16 | ND |
| 37 | 4.68 | 3.58 | ND |
| 38 | 0.622 | 1.14 | 3.8 |
| 39 | 3.82 | 4.98 | ND |
| 40 | 0.212 | 5.58 | >10 |
| 41 | 0.48 | 16.5 | ND |
| 42 | 0.446 | 14.55 | >10 |
| 43 | 0.469 | 10.99 | >10 |
| 44 | 0.322 | 1.79 | >10 |
| 45 | 0.434 | 9.29 | 5.44 |
| 46 | 0.426 | 16.26 | 4.95 |
| 47 | 0.498 | 7.83 | >10 |
| 48 | 0.224 | 6.22 | 9.58 |
| 49 | 0.313 | 5.6 | >10 |
| 50 | 5.04 | 22.2 | ND |
| 51 | 6.7 | 22.2 | ND |
| 52 | 3.08 | 16.4 | ND |
| 53 | 0.659 | 3.19 | 4.17 |
| 54 | 0.585 | 3.88 | 0.19 |
| 55 | 0.722 | 4.94 | ND |
| 56 | 1.63 | 2.69 | >10 |
| 57 | 0.392 | 1.9 | >3 |
| 58 | 4.68 | 22.2 | ND |
| 59 | 2.13 | 3.31 | ND |
| 60 | 5.1 | 20.5 | ND |
| 61 | 8.28 | 22.2 | ND |
| 62 | 0.197 | 1.24 | 0.52 |
| 63 | 0.352 | 6.9 | 2.46 |
| 64 | 1.04 | 22.2 | ND |
| 65 | 0.634 | 12.2 | ND |
| 66 | 1.76 | 6.15 | ND |
| 67 | 0.452 | 0.81 | >3 |
| 68 | 0.151 | 2.59 | 1.13 |
| 69 | 0.663 | 2.34 | ND |
| 70 | 0.434 | 4.29 | >3 |
| 71 | 0.628 | 22.2 | ND |
| 72 | 0.0781 | 0.416 | 0.167 |
| 73 | 0.862 | 3.83 | ND |
| 74 | 0.526 | 1.65 | ND |
| 75 | 0.0376 | 0.225 | 0.433 |
| 76 | 4.5 | 2.98 | 13.4 |
| 77 | 0.172 | 0.983 | 6.91 |
| 78 | 3.99 | 0.712 | ND |
| 79 | 0.904 | 2.65 | ND |
| 80 | 9.39 | 13.4 | ND |
| 81 | 9.29 | 22.2 | ND |
| 82 | 2.96 | 8.72 | ND |
| 83 | 0.237 | 0.653 | >3 |
| 84 | 10.6 | 22.2 | ND |
| 85 | 1.85 | 13.2 | >3 |
| 86 | 3.03 | 2.6 | ND |
| 87 | 0.366 | 0.465 | >3 |
| 88 | 8.48 | 22.2 | ND |
| 89 | 0.122 | 0.351 | 0.965 |
| 90 | 2.5 | 5.18 | 6.3 |
| 91 | 0.331 | 3.35 | >3 |
| 92 | 1.69 | 2.43 | ND |
| 93 | 5.09 | 6.42 | ND |
| 94 | 4.82 | 21.5 | ND |
| 95 | 5.07 | 5.62 | ND |
| 96 | 3.19 | 21.5 | ND |
| 97 | 1.41 | 1.87 | 15.3 |
| 98 | 11.3 | 7.01 | ND |
| 99 | 2.3 | 2.32 | ND |
| 100 | 8.36 | 5.32 | ND |
| 101 | 7.37 | 5.33 | ND |
| 102 | 5.68 | 4.37 | ND |
| 103 | 4.66 | 3.48 | ND |
| 104 | 2.38 | 2.34 | ND |
| 105 | 6.78 | 5.34 | ND |
| 106 | 6.01 | 4.87 | ND |
| 107 | 4.02 | 1.98 | 8.6 |
| 108 | 11.0 | 4.49 | ND |
| 109 | 9.24 | 4.42 | ND |
| 110 | 4.03 | 5.9 | ND |
| 111 | 6.9 | 5.74 | ND |
| 112 | 5.43 | 4.31 | ND |
| 113 | 4.64 | 4.22 | ND |
| 114 | 3.96 | 3.68 | ND |
| 115 | 1.85 | 7.12 | ND |
| 116 | 0.182 | 0.639 | 1.18 |
| 117 | 0.391 | 0.725 | 1.35 |
| 118 | 0.529 | 1.73 | 1.32 |
| 119 | 0.249 | 1.1 | 0.998 |
| 120 | 4.41 | 22.2 | ND |
| 121 | 0.776 | 10.21 | >10 |
| 122 | 1.96 | 7.04 | ND |
| 123 | 1.97 | 12.6 | ND |
| 124 | 4.6 | 13.14 | ND |
| 125 | 0.18 | 0.192 | 1.6 |
| 126 | 0.0834 | 1.14 | 1.3 |
| 127 | 0.233 | 1.04 | 2.0 |
| 128 | 0.0273 | 0.318 | 0.40 |
| 129 | 0.281 | 2.24 | 2.25 |

TABLE 1-continued

| Example # | TR-FRET Binding $K_i$: BRD4 (BDI_K57-E168) (μM) | TR-FRET Binding $K_i$: BRD4 (BDII_E352-M457) (μM) | Cellular proliferation: $EC_{50}$ (μM) |
|---|---|---|---|
| 130 | 0.471 | 1.22 | 1.77 |
| 131 | 9.4 | 22.2 | ND |
| 132 | 10.91 | 22.2 | ND |
| 133 | 0.31 | 0.576 | 1.83 |
| 134 | 0.493 | 1.17 | >10 |
| 135 | 0.355 | 1.86 | >10 |
| 136 | 0.564 | 1.98 | ND |
| 137 | 0.218 | 1.02 | 4.88 |
| 138 | 1.48 | 1.82 | ND |
| 139 | 0.728 | 1.19 | 8.56 |
| 140 | 0.607 | 1.3 | ND |
| 141 | 0.123 | 1.6 | 2.42 |
| 142 | 0.357 | 0.775 | 2.13 |
| 143 | 0.259 | 2.11 | ND |
| 144 | 0.446 | 1.23 | ND |
| 145 | 1.19 | 3.92 | >10 |
| 146 | 0.0749 | 0.326 | 1.61 |
| 147 | 11.9 | 12.2 | ND |
| 148 | 0.355 | 0.605 | 4.32 |
| 149 | 0.884 | 3.88 | 2.32 |
| 150 | 10.7 | 9.69 | ND |
| 151 | 10.4 | 22.2 | ND |
| 152 | 4.7 | 7.87 | ND |
| 153 | 2.22 | 7.32 | ND |
| 154 | 2.99 | 7.12 | ND |
| 155 | 2.57 | 5.46 | ND |
| 156 | 8.49 | 21.9 | ND |
| 157 | 7.41 | 22.2 | ND |
| 158 | 1.5 | 2.14 | 7.75 |
| 159 | 1.08 | 2.1 | 28.6 |
| 160 | 11.5 | 22.2 | ND |
| 161 | 0.109 | 0.658 | 0.694 |
| 162 | 0.0591 | 0.754 | 1.03 |
| 163 | 0.912 | 2.81 | ND |
| 164 | 1.0 | 2.03 | ND |
| 165 | 0.595 | 7.49 | ND |
| 166 | 0.63 | 10.5 | ND |
| 167 | 0.627 | 2.25 | >3 |
| 168 | 0.106 | 0.757 | >3 |

ND = Not Determined

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

What is claimed is:

1. A compound of formula (I), or a pharmaceutically acceptable salt thereof

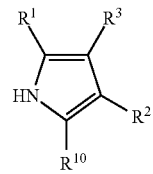

(I)

wherein
$R^1$ is $C_1$-$C_3$ alkyl;
$R^2$ is hydrogen or $C_1$-$C_3$ alkyl;
$R^3$ is —C(O)NR$^8$R$^9$;
$R^8$ and $R^9$ are chosen from one of the following groups:
  (i) $R^8$ and $R^9$ are both H;
  (ii) $R^8$ is H and $R^9$ is $C_1$-$C_3$ alkylene-C(O)O—$C_1$-$C_3$ alkyl or OH; or
  (iii) $R^8$ is $C_1$-$C_3$ alkylene-aryl and $R^9$ is $C_1$-$C_3$ alkylene-C(O)—$C_1$-$C_3$ alkyl;
$R^{10}$ is aryl or heteroaryl, wherein $R^{10}$ is optionally substituted with 1 to 3 substituents designated as $R^{40}$, $R^{41}$, and $R^{42}$ and independently selected from the group consisting of
  $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$ alkenylene-O—$C_1$-$C_3$ alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—NH$_2$, —C(O)—NR$^{20}$R$^{22}$, and -L-R$^{12}$,
wherein L is absent or is —$C_1$-$C_3$alkylene-, —$C_2$-$C_3$alkenylene-, —NH—, —NH—$C_1$-$C_3$alkylene-, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, or —O—;
$R^{12}$ is selected from the group consisting of $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which is optionally substituted with one, two, or three substituents designated $R^{15}$, $R^{16}$, and $R^{17}$,
$R^{15}$, $R^{16}$, and $R^{17}$ are independently selected from the group consisting of
  OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-NR$^{30}$R$^{32}$, —C(O)NR$^{30}$R$^{32}$, —O—$C_1$-$C_4$ alkyl-NR$^{30}$R$^{32}$, —NR$^{30}$R$^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl,
wherein said heterocycloalkyl, heteroaryl or aryl groups on $R^{15}$, $R^{16}$, and $R^{17}$ are optionally independently substituted with 1 to 3 substituents selected from the group consisting of $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl;

$R^{26}$ is $C_1$-$C_3$ alkylene-$C_3$-$C_6$ cycloalkyl;

$R^{20}$ and $R^{22}$ are independently selected from the group consisting of H and $C_1$-$C_6$ alkyl; and $R^{30}$ and $R^{32}$ are independently selected from the group consisting of H and $C_1$-$C_4$ alkyl.

2. The compound of claim 1, or a pharmaceutically acceptable salt thereof, wherein $R^1$ is methyl.

3. The compound of claim 2, or a pharmaceutically acceptable salt thereof, wherein $R^2$ is hydrogen.

4. The compound of claim 3, or a pharmaceutically acceptable salt thereof, wherein $R^8$ and $R^9$ are both H.

5. The compound of claim 4, or a pharmaceutically acceptable salt thereof, wherein $R^{10}$ is heteroaryl, which is optionally substituted with 1 to 3 substituents designated as $R^{40}$, $R^{41}$, and $R^{42}$ and independently selected from the group consisting of $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—$NH_2$, —C(O)—$NR^{20}R^{22}$, and -L-$R^{12}$, wherein L is absent or is —$C_1$-$C_3$alkylene-, —$C_2$-$C_3$alkenylene-, —NH—, —NH—$C_1$-$C_3$alkylene-, —$NR^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, or —O—;

$R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which is optionally substituted with one, two, or three substituents designated $R^{15}$, $R^{16}$, and $R^{17}$, $R^{15}$, $R^{16}$, and $R^{17}$ are independently selected from the group consisting of OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ are optionally independently substituted with 1 to 3 substituents selected from the group consisting of $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

6. The compound of claim 4, or a pharmaceutically acceptable salt thereof, wherein $R^{10}$ is phenyl which is optionally substituted with 1 to 3 substituents designated as $R^{40}$, $R^{41}$, and $R^{42}$ and independently selected from the group consisting of $NO_2$, $NR^{20}R^{22}$, halo, $C_1$-$C_6$ alkyl, $C_1$-$C_6$ haloalkyl, —O—$C_1$-$C_6$ alkyl, —O—$C_1$-$C_6$ haloalkyl, $C_1$-$C_3$ alkylene-OH, $C_1$-$C_3$ alkylene-C(O)OH, $C_1$-$C_3$ alkylene-C(O)O—$C_1$-$C_4$ alkyl, $C_2$-$C_3$alkenylene-O—$C_1$-$C_3$alkyl, —NHC(O)—$C_1$-$C_3$ alkyl, —NH—$SO_2$—$C_1$-$C_3$ alkyl, —NH—$SO_2$—$C_1$-$C_3$ haloalkyl, —$SO_2$—$NH_2$, —C(O)—$NR^{20}R^{22}$, and -L-$R^{12}$, wherein L is absent or is —$C_1$-$C_3$alkylene-, —$C_2$-$C_3$alkenylene-, —NH—, —NH—$C_1$-$C_3$alkylene-, —$NR^{26}$—, —NHS(O)$_2$—, NHS(O)$_2$—$C_1$-$C_3$alkylene-, —NH—C(O)—$C_1$-$C_3$alkylene-, —C(O)—, —C(O)—NH—$C_1$-$C_3$alkylene-, and or —O—;

$R^{12}$ is selected from the group consisting of: $C_1$-$C_6$ alkyl, $C_1$-$C_6$ haloalkyl, $C_3$-$C_{10}$ cycloalkyl, 3 to 8 membered heterocycloalkyl, 5 to 12 membered heteroaryl, and aryl, which is optionally substituted with one, two, or three substituents designated $R^{15}$, $R^{16}$, and $R^{17}$, $R^{15}$, $R^{16}$, and $R^{17}$ are independently selected from the group consisting of OH, CN, halo, $C_1$-$C_3$ alkyl, $C_1$-$C_3$ haloalkyl, —O—$C_1$-$C_3$ alkyl, —O—$C_1$-$C_3$ haloalkyl, —$C_1$-$C_3$ alkylene-OH, —$C_1$-$C_3$ alkylene-C(O)O—$C_1$-$C_3$ alkyl, —C(O)—$C_1$-$C_4$ alkyl, —C(O)O$C_1$-$C_4$ alkyl, —C(O)NH—$C_1$-$C_3$ alkylene-$NR^{30}R^{32}$, —C(O)$NR^{30}R^{32}$, —O—$C_1$-$C_4$ alkyl-$NR^{30}N^{32}$, —$NR^{30}R^{32}$, —NHC(O)O—$C_1$-$C_4$ alkyl, —NH—S(O)$_2$—$C_1$-$C_3$ alkyl, —NH—S(O)$_2$—$C_1$-$C_3$ haloalkyl, —S(O)$_2$—$C_1$-$C_3$ alkyl, aryl, —O-aryl, —$C_1$-$C_3$ alkylene-aryl, $C_3$-$C_6$ cycloalkyl, heterocycloalkyl, —$C_1$-$C_3$ alkylene-heterocycloalkyl, —C(O)-heterocycloalkyl, 5 to 12 membered heteroaryl, and —C(O)NH—$C_1$-$C_3$alkylene-heteroaryl, wherein said heterocycloalkyl, heteroaryl or aryl groups on $R^{15}$, $R^{16}$, and $R^{17}$ are optionally independently substituted with 1 to 3 substituents selected from the group consisting of $C_1$-$C_3$-alkyl, $C_1$-$C_3$-haloalkyl, —O—$C_1$-$C_3$-alkyl, —O—$C_1$-$C_3$-haloalkyl, halo, —NH—S(O)$_2$—$C_1$-$C_3$ alkyl, —NH—S(O)$_2$—$C_1$-$C_3$ haloalkyl, and —S(O)$_2$—$C_1$-$C_3$ alkyl.

7. The compound of claim 6, or a pharmaceutically acceptable salt thereof, wherein said phenyl is substituted with one substituent designated as $R^{41}$

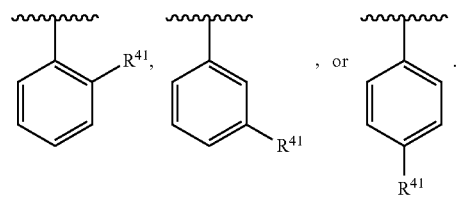

8. The compound of claim 4, or a pharmaceutically acceptable salt thereof, wherein $R^{10}$ is phenyl which is substituted with one substituent, $R^{41}$, and optionally further substituted with 1 or 2 substituents designated as $R^{40}$ and $R^{42}$; wherein $R^{41}$ is -L-$R^{12}$;

$R^{40}$ is $NR^{20}R^{22}$, halo, $C_1$-$C_3$ alkylene-OH, $C_1$-$C_3$ alkylene-C(O)OH, $C_1$-$C_3$ alkylene-C(O)O—$C_1$-$C_4$ alkyl, —NHC(O)—$C_1$-$C_3$ alkyl, —NH—$SO_2$—$C_1$-$C_3$ alkyl, —NH—$SO_2$—$C_1$-$C_3$ haloalkyl, or —$SO_2$—$NH_2$; and $R^{42}$ is $C_1$-$C_6$ alkyl, $C_1$-$C_6$ haloalkyl, halo, or -L-$R^{12}$; wherein L is absent and $R^{12}$ is optionally substituted cyclopropyl.

9. The compound of claim 4, or a pharmaceutically acceptable salt thereof, wherein $R^{10}$ is phenyl which is substituted with one substituent, $R^{41}$, and optionally further substituted with 1 or 2 substituents designated as $R^{40}$ and $R^{42}$; wherein R$^{41}$ is -L-R$^{12}$;

L is absent, —C$_2$-C$_3$ alkenylene, —NH—, —NHS(O)$_2$—, —NH—C(O)—C$_1$-C$_3$ alkylene, or O;

R$^{12}$ is C$_3$-C$_{10}$ cycloalkyl, 3 to 8 membered heterocycloalkyl, 5 to 12 membered heteroaryl, or aryl, each of which is optionally substituted; or R$^{12}$ is C$_1$-C$_6$ alkyl substituted with a substituent selected from the group consisting of C$_3$-C$_6$ cycloalkyl, 3 to 8 membered heterocycloalkyl, 5 to 12 membered heteroaryl, and aryl; wherein each of the C$_3$-C$_6$ cycloalkyl, 3 to 8 membered heterocycloalkyl, 5 to 12 membered heteroaryl, and aryl is optionally substituted;

R$^{40}$ is NR$^{20}$R$^{22}$, halo, C$_1$-C$_3$ alkylene-OH, C$_1$-C$_3$ alkylene-C(O)OH, C$_1$-C$_3$ alkylene-C(O)O—C$_1$-C$_4$ alkyl, —NHC(O)—C$_1$-C$_3$ alkyl, —NH—SO$_2$—C$_1$-C$_3$ alkyl, —NH—SO$_2$—C$_1$-C$_3$ haloalkyl, or —SO$_2$—NH$_2$; and R$^{42}$ is C$_1$-C$_6$ alkyl, C$_1$-C$_6$ haloalkyl, halo, or -L-R$^{12}$; wherein L is absent and R$^{12}$ is optionally substituted cyclopropyl.

10. The compound of claim 4, or a pharmaceutically acceptable salt thereof, wherein R$^{10}$ is

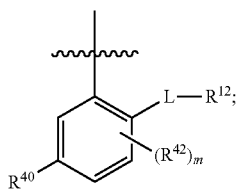

wherein

L is —NH— or O;

R$^{12}$ is phenyl, C$_3$-C$_6$ cycloalkyl, 5-membered heterocycloalkyl, or 6-membered heterocycloalkyl; each of which is optionally substituted; or R$^{12}$ is C$_1$-C$_3$ alkyl substituted with a substituent selected from the group consisting of phenyl, C$_3$-C$_6$ cycloalkyl, 5-membered heterocycloalkyl, and 6-membered heterocycloalkyl; wherein each of the phenyl, C$_3$-C$_6$ cycloalkyl, 5-membered heterocycloalkyl, and 6-membered heterocycloalkyl is optionally substituted;

m is 0 or 1;

R$^{42}$ is C$_6$ alkyl, C$_1$-C$_6$ haloalkyl, halo, or -L-R$^{12}$; wherein L is absent and R$^{12}$ is optionally substituted cyclopropyl, and R$^{40}$ is NR$^{20}$R$^{22}$, halo, C$_1$-C$_3$ alkylene-OH, C$_1$-C$_3$ alkylene-C(O)OH, C$_1$-C$_3$ alkylene-C(O)O—C$_1$-C$_4$ alkyl, —NH—SO$_2$—C$_1$-C$_3$ alkyl, —NH—SO$_2$—C$_1$-C$_3$ haloalkyl, or —SO$_2$—NH$_2$.

11. The compound of claim 1, or a pharmaceutically acceptable salt thereof, wherein said compound is selected from the group consisting of 5-(2-aminophenyl)-2-methyl-1H-pyrrole-3-carboxamide;
5-[2-(acetylamino)phenyl]-2-methyl-1H-pyrrole-3-carboxamide;
2-methyl-5-(3-nitrophenyl)-1H-pyrrole-3-carboxamide;
5-(3-aminophenyl)-2-methyl-1H-pyrrole-3-carboxamide;
5-[3-(acetylamino)phenyl]-2-methyl-1H-pyrrole-3-carboxamide;
2-methyl-5-{3-[(methyl sulfonyl)amino]phenyl}-1H-pyrrole-3-carboxamide;
2-methyl-5-(4-nitrophenyl)-1H-pyrrole-3-carboxamide;
5-(4-aminophenyl)-2-methyl-1H-pyrrole-3-carboxamide;
2-methyl-5-{4-[(methylsulfonyl)amino]phenyl}-1H-pyrrole-3-carboxamide;
5-[4-(acetylamino)phenyl]-2-methyl-1H-pyrrole-3-carboxamide;
5-{2-[(4-chlorobenzyl)amino]phenyl}-2-methyl-1H-pyrrole-3-carboxamide;
5-[2-(benzylamino)phenyl]-2-methyl-1H-pyrrole-3-carboxamide;
2-methyl-5-{2-[(tetrahydrofuran-2-ylmethyl)amino]phenyl}-1H-pyrrole-3-carboxamide;
5-{2-[(cyclopentylmethyl)amino]phenyl}-2-methyl-1H-pyrrole-3-carboxamide;
5-(2-{[(4-bromothiophen-2-yl)methyl]amino}phenyl)-2-methyl-1H-pyrrole-3-carboxamide;
2-methyl-5-{2-[(3,4,5-trimethoxybenzyl)amino]phenyl}-1H-pyrrole-3-carboxamide;
2-methyl-5-{2-[(tetrahydrofuran-3-ylmethyl)amino]phenyl}-1H-pyrrole-3-carboxamide;
2-methyl-5-(2-{[(3R)-tetrahydrofuran-3-ylmethyl]amino}phenyl)-1H-pyrrole-3-carboxamide;
2-methyl-5-(2-{[(3 S)-tetrahydrofuran-3-ylmethyl]amino}phenyl)-1H-pyrrole-3-carboxamide;
5-(2-{[(4,5-dimethylfuran-2-yl)methyl]amino}phenyl)-2-methyl-1H-pyrrole-3-carboxamide;
5-(2-{[3,5-bis(trifluoromethyl)benzyl]amino}phenyl)-2-methyl-1H-pyrrole-3-carboxamide;
5-{2-[(2,6-difluorobenzyl)amino]phenyl}-2-methyl-1H-pyrrole-3-carboxamide;
5-{2-[(4-fluorobenzyl)amino]phenyl}-2-methyl-1H-pyrrole-3-carboxamide;
2-methyl-5-{2-[(2-methylbenzyl)amino]phenyl}-1H-pyrrole-3-carboxamide;
2-methyl-5-{2-[(3-methylbenzyl)amino]phenyl}-1H-pyrrole-3-carboxamide;
5-{2-[(cyclopropylmethyl)amino]phenyl}-2-methyl-1H-pyrrole-3-carboxamide;
5-[2-(butylamino)phenyl]-2-methyl-1H-pyrrole-3-carboxamide;
2-methyl-5-(2-{[4-(trifluoromethyl)benzyl]amino}phenyl)-1H-pyrrole-3-carboxamide;
2-methyl-5-{2-[(4-methylbenzyl)amino]phenyl}-1H-pyrrole-3-carboxamide;
5-{2-[(4-methoxybenzyl)amino]phenyl}-2-methyl-1H-pyrrole-3-carboxamide;
5-{2-[(4-cyanobenzyl)amino]phenyl}-2-methyl-1H-pyrrole-3-carboxamide;
5-{2-[(4-bromobenzyl)amino]phenyl}-2-methyl-1H-pyrrole-3-carboxamide;
5-{2-[(3,4-dichlorobenzyl)amino]phenyl}-2-methyl-1H-pyrrole-3-carboxamide;
5-{2-[(2-chlorobenzyl)amino]phenyl-}2-methyl-1H-pyrrole-3-carboxamide;
5-{2-[(3-chlorobenzyl)amino]phenyl}-2-methyl-1H-pyrrole-3-carboxamide;
5-{2-[(cyclohexylmethyl)amino]phenyl}-2-methyl-1H-pyrrole-3-carboxamide;
5-(2-{[4-(dimethylamino)benzyl]amino}phenyl)-2-methyl-1H-pyrrole-3-carboxamide;
2-methyl-5-{2-[(thiophen-2-ylmethyl)amino]phenyl}-1H-pyrrole-3-carboxamide;
5-{2-[(3,5-dichlorobenzyl)amino]phenyl}-2-methyl-1H-pyrrole-3-carboxamide;
tert-butyl 3-({[2-(4-carbamoyl-5-methyl-1H-pyrrol-2-yl)phenyl]amino}methyl)pyrrolidine-1-carboxylate;
tert-butyl 4-({[2-(4-carbamoyl-5-methyl-1H-pyrrol-2-yl)phenyl]amino}methyl)piperidine-1-carboxylate;
2-methyl-5-{2-[(pyrrolidin-3-ylmethyl)amino]phenyl}-1H-pyrrole-3-carboxamide;

2-methyl-5-{2-[(piperidin-4-ylmethyl)amino]phenyl}-1H-pyrrole-3-carboxamide;
tert-butyl 4-(2-{[2-(4-carbamoyl-5-methyl-1-pyrrol-2-yl)phenyl]amino}ethyl)piperidine-1-carboxylate;
tert-butyl [cis-4-({[2-(4-carbamoyl-5-methyl-1H-pyrrol-2-yl)phenyl]amino}methyl)cyclohexyl]carbamate;
tert-butyl [trans-4-({[2-(4-carbamoyl-5-methyl-1H-pyrrol-2-yl)phenyl]amino}methyl)cyclohexyl]carbamate;
2-methyl-5-(2-{[2-(piperidin-4-yl)ethyl]amino}phenyl)-1H-pyrrole-3-carboxamide;
5-(2-{[(cis-4-aminocyclohexyl)methyl]amino}phenyl)-2-methyl-1H-pyrrole-3-carboxamide;
5-(2-{[(trans-4-aminocyclohexyl)methyl]amino}phenyl)-2-methyl-1H-pyrrole-3-carboxamide;
tert-butyl [4-({[2-(4-carbamoyl-5-methyl-1H-pyrrol-2-yl)phenyl]amino}methyl)phenyl]carbamate;
tert-butyl [3-({[2-(4-carbamoyl-5-methyl-1H-pyrrol-2-yl)phenyl]amino}methyl)phenyl]carbamate;
5-{2-[(4-aminobenzyl)amino]phenyl}-2-methyl-1H-pyrrole-3-carboxamide;
5-{2-[(3-aminobenzyl)amino]phenyl}-2-methyl-1H-pyrrole-3-carboxamide;
5-{2-[(4-hydroxybenzyl)amino]phenyl}-2-methyl-1H-pyrrole-3-carboxamide;
5-[2-({[5-(hydroxymethyl)furan-2-yl]methyl}amino)phenyl]-2-methyl-1H-pyrrole-3-carboxamide;
5-{2-[(1H-indol-5-ylmethyl)amino]phenyl}-2-methyl-1H-pyrrole-3-carboxamide;
5-{2-[(cyclopentylmethyl)(thiophen-2-ylmethyl)amino]phenyl}-2-methyl-1H-pyrrole-3-carboxamide;
5-{2-[(cyclopentylmethyl)(4-methoxybenzyl)amino]phenyl}-2-methyl-1H-pyrrole-3-carboxamide;
5-[2-(cyclohexylamino)phenyl]-2-methyl-1H-pyrrole-3-carboxamide;
2-methyl-5-[2-(tetrahydrofuran-3-ylamino)phenyl]-1H-pyrrole-3-carboxamide;
2-methyl-5-[2-(pyrrolidin-3-ylamino)phenyl]-1H-pyrrole-3-carboxamide;
2-methyl-5-[2-(piperidin-4-ylamino)phenyl]-1H-pyrrole-3-carboxamide;
5-[2-(cyclobutylamino)phenyl]-2-methyl-1H-pyrrole-3-carboxamide;
5-[2-(2,3-dihydro-1H-inden-1-ylamino)phenyl]-2-methyl-1H-pyrrole-3-carboxamide;
2-methyl-5-[2-(tetrahydro-2H-thiopyran-4-ylamino)phenyl]-1H-pyrrole-3-carboxamide;
5-[2-(2,3-dihydro-1H-inden-2-ylamino)phenyl]-2-methyl-1H-pyrrole-3-carboxamide;
2-methyl-5-[2-(tetrahydro-2H-pyran-4-ylamino)phenyl]-1H-pyrrole-3-carboxamide;
5-[2-(1-azabicyclo[2.2.2]oct-3-ylamino)phenyl]-2-methyl-1H-pyrrole-3-carboxamide;
2-methyl-5-{2-[tricyclo[3.3.1.1$^{3,7}$]dec-2-ylamino]phenyl}-1H-pyrrole-3-carboxamide;
5-[2-(cycloheptylamino)phenyl]-2-methyl-1H-pyrrole-3-carboxamide;
2-methyl-5-[2-(1,2,3,4-tetrahydronaphthalen-2-ylamino)phenyl]-1H-pyrrole-3-carboxamide;
5-{2-[(2-fluorocyclohexyl)amino]phenyl}-2-methyl-1H-pyrrole-3-carboxamide;
2-methyl-5-{2-[(phenylacetyl)amino]phenyl}-1H-pyrrole-3-carboxamide;
2-methyl-5-[2-(phenylamino)phenyl]-1H-pyrrole-3-carboxamide;
5-(2-{[(4-chlorophenyl)sulfonyl]amino}phenyl)-2-methyl-1H-pyrrole-3-carboxamide;
5-{2-[(cyclohexylsulfonyl)amino]phenyl}-2-methyl-1H-pyrrole-3-carboxamide;
2-methyl-5-{2-[(phenylsulfonyl)amino]phenyl}-1H-pyrrole-3-carboxamide;
2-methyl-5-{2-[(pyridin-3-ylsulfonyl)amino]phenyl}-1H-pyrrole-3-carboxamide;
2-methyl-5-(2-{[(3,3,3-trifluoropropyl)sulfonyl]amino}phenyl)-1H-pyrrole-3-carboxamide;
5-{2-[(benzylsulfonyl)amino]phenyl}-2-methyl-1H-pyrrole-3-carboxamide;
5-(2-{[(2,4-difluorophenyl)sulfonyl]amino}phenyl)-2-methyl-1H-pyrrole-3-carboxamide;
5-(2-{[(4-chlorobenzyl)sulfonyl]amino}phenyl)-2-methyl-1H-pyrrole-3-carboxamide;
2-methyl-5-(2-{[(2,2,2-trifluoroethyl)sulfonyl]amino}phenyl)-1H-pyrrole-3-carboxamide;
5-{2-[(cyclopentylsulfonyl)amino]phenyl}-2-methyl-1H-pyrrole-3-carboxamide;
5-(2-{[(4-hydroxyphenyl)sulfonyl]amino}phenyl)-2-methyl-1H-pyrrole-3-carboxamide;
2-methyl-5-(2-phenoxyphenyl)-1H-pyrrole-3-carboxamide;
5-(2,4-dimethylphenyl)-2-methyl-1H-pyrrole-3-carboxamide;
5-(2-amino-6-phenoxyphenyl)-2-methyl-1H-pyrrole-3-carboxamide;
5-[4-(3,5-dimethyl-1,2-oxazol-4-yl)phenyl]-2-methyl-1H-pyrrole-3-carboxamide;
methyl N-({5-[4-(3,5-dimethyl-1,2-oxazol-4-yl)phenyl]-2-methyl-1H-pyrrol-3-yl}carbonyl)-beta-alaninate;
methyl N-({5-[4-(3,5-dimethyl-1,2-oxazol-4-yl)phenyl]-2-methyl-1H-pyrrol-3-yl}carbonyl)glycinate;
5-[4-(3,5-dimethyl-1,2-oxazol-4-yl)phenyl]-N-hydroxy-2-methyl-1H-pyrrole-3-carboxamide;
2-methyl-5-{4'-[(4-methylpiperazin-1-yl)methyl]biphenyl-4-yl}-1H-pyrrole-3-carboxamide;
5-(3'-hydroxybiphenyl-4-yl)-2-methyl-1H-pyrrole-3-carboxamide;
2-methyl-5-(3',4',5'-trimethoxybiphenyl-4-yl)-1H-pyrrole-3-carboxamide;
5-[4-(furan-3-yl)phenyl]-2-methyl-1H-pyrrole-3-carboxamide;
2-methyl-5-[4-(thiophen-3-yl)phenyl]-1H-pyrrole-3-carboxamide;
2-methyl-5-[4-(pyridin-4-yl)phenyl]-1H-pyrrole-3-carboxamide;
2-methyl-5-[4-(1-methyl-1H-pyrazol-4-yl)phenyl]-1H-pyrrole-3-carboxamide;
5-[3'-(dimethylcarbamoyl)biphenyl-4-yl]-2-methyl-1H-pyrrole-3-carboxamide;
2-methyl-5-[3'-(morpholin-4-yl)biphenyl-4-yl]-1H-pyrrole-3-carboxamide;
5-{3'-[(furan-2-ylmethyl)carbamoyl]biphenyl-4-yl}-2-methyl-1H-pyrrole-3-carboxamide;
5-{4-[(1E)-3-methoxyprop-1-en-1-yl]phenyl-2-methyl-1H-pyrrole-3-carboxamide;
5-[4'-(dimethylcarbamoyl)biphenyl-4-yl]-2-methyl-1H-pyrrole-3-carboxamide;
2-methyl-5-[4-(pyrimidin-5-yl)phenyl]-1H-pyrrole-3-carboxamide;
2-methyl-5-{4'-[(methylsulfonyl)amino]biphenyl-4-yl}-1H-pyrrole-3-carboxamide;
5-[4-(1-benzyl-1H-pyrazol-4-yl)phenyl]-2-methyl-1H-pyrrole-3-carboxamide;
5-[4-(3,5-dimethyl-1H-pyrazol-4-yl)phenyl]-2-methyl-1H-pyrrole-3-carboxamide;

2-methyl-5-[4-(quinolin-6-yl)phenyl]-1H-pyrrole-3-carboxamide;
2-methyl-5-{4'-[(4-methylpiperazin-1-yl)carbonyl]biphenyl-4-yl}-1H-pyrrole-3-carboxamide;
5-(2-bromophenyl)-2-methyl-1H-pyrrole-3-carboxamide;
5-[2-(4-chlorophenoxy)phenyl]-2-methyl-1H-pyrrole-3-carboxamide;
5-[2-(2-fluorophenoxy)phenyl]-2-methyl-1H-pyrrole-3-carboxamide;
5-[2-(1H-indol-6-yloxy)phenyl]-2-methyl-1H-pyrrole-3-carboxamide;
5-[2-(4-aminophenoxy)phenyl]-2-methyl-1H-pyrrole-3-carboxamide;
2-methyl-5-[2-(pyridin-4-yloxy)phenyl]-1H-pyrrole-3-carboxamide;
5-[2-(4-benzylphenoxy)phenyl]-2-methyl-1H-pyrrole-3-carboxamide;
2-methyl-5-[2-(4-phenoxyphenoxy)phenyl]-1H-pyrrole-3-carboxamide;
5-[2-(4-cyanophenoxy)phenyl]-2-methyl-1H-pyrrole-3-carboxamide;
5-[2-(4-cyclopentylphenoxy)phenyl]-2-methyl-1H-pyrrole-3-carboxamide;
5-[2-(isoquinolin-5-yloxy)phenyl]-2-methyl-1H-pyrrole-3-carboxamide;
2-methyl-5-[2-(pyridin-3-yloxy)phenyl]-1H-pyrrole-3-carboxamide;
5-[2-(3-cyanophenoxy)phenyl]-2-methyl-1H-pyrrole-3-carboxamide;
2-methyl-5-[2-(quinolin-5-yloxy)phenyl]-1H-pyrrole-3-carboxamide;
5-[2-(4-chloro-2-fluorophenoxy)phenyl]-2-methyl-1H-pyrrole-3-carboxamide;
5-[2-(1H-indol-5-yloxy)phenyl]-2-methyl-1H-pyrrole-3-carboxamide;
2-methyl-5-[2-(pyridin-2-yloxy)phenyl]-1H-pyrrole-3-carboxamide;
2-methyl-5-{2-[4-(methyl sulfonyl)phenoxy]phenyl}-1H-pyrrole-3-carboxamide;
methyl 3-{2-[2-(4-carbamoyl-5-methyl-1H-pyrrol-2-yl)phenoxy]phenyl}propanoate;
2-methyl-5-[2-(3-methylphenoxy)phenyl]-1H-pyrrole-3-carboxamide;
5-{2-[4-(1H-imidazol-1-yl)phenoxy]phenyl}-2-methyl-1H-pyrrole-3-carboxamide;
2-methyl-5-[2-(5,6,7,8-tetrahydronaphthalen-1-yloxy)phenyl]-1H-pyrrole-3-carboxamide;
5-[2-(4-methoxyphenoxy)phenyl]-2-methyl-1H-pyrrole-3-carboxamide;
5-[2-(2-benzylphenoxy)phenyl]-2-methyl-1H-pyrrole-3-carboxamide;
2-methyl-5-[2-(naphthalen-2-yloxy)phenyl]-1H-pyrrole-3-carboxamide;
2-methyl-5-[2-(naphthalen-1-yloxy)phenyl]-1H-pyrrole-3-carboxamide;
5-[2-(4-fluorophenoxy)phenyl]-2-methyl-1H-pyrrole-3-carboxamide;
5-[2-(3-chlorophenoxy)phenyl]-2-methyl-1H-pyrrole-3-carboxamide;
5-[2-(4-ethylphenoxy)phenyl]-2-methyl-1H-pyrrole-3-carboxamide;
5-[2-(2,3-dihydro-1H-inden-5-yloxy)phenyl]-2-methyl-1H-pyrrole-3-carboxamide;
5-[2-(6-hydroxy-1H-benzimidazol-1-yl)phenyl]-2-methyl-1H-pyrrole-3-carboxamide;
5-[2-(5-hydroxy-1H-benzimidazol-1-yl)phenyl]-2-methyl-1H-pyrrole-3-carboxamide;
5-(2, 6-difluorophenyl)-2-methyl-1H-pyrrole-3-carboxamide;
5-(2-benzylphenyl)-2-methyl-1H-pyrrole-3-carboxamide;
2-methyl-5-(3,4, 5-trimethoxyphenyl)-1H-pyrrole-3-carboxamide;
5-(biphenyl-3-yl)-2-methyl-1H-pyrrole-3-carboxamide;
5-(3'-methoxybiphenyl-3-yl)-2-methyl-1H-pyrrole-3-carboxamide;
2-methyl-5-[3-(thiophen-3-yl)phenyl]-1H-pyrrole-3-carboxamide;
5-(2'-acetylbiphenyl-3-yl)-2-methyl-1H-pyrrole-3-carboxamide;
2-methyl-5-[3-(pyridin-3-yl)phenyl]-1H-pyrrole-3-carboxamide;
2-methyl-5-[3-(1H-pyrazol-4-yl)phenyl]-1H-pyrrole-3-carboxamide;
2-methyl-5-[3-(1-methyl-1H-indol-5-yl)phenyl]-1H-pyrrole-3-carboxamide;
2-methyl-5-{3-[(E)-2-phenylethenyl]phenyl}-1H-pyrrole-3-carboxamide;
2-methyl-5-{3'-[(4-methylpiperazin-1-yl)methyl]biphenyl-3-yl}-1H-pyrrole-3-carboxamide;
5-(4'-{[2-(dimethylamino)ethyl]carbamoyl}biphenyl-3-yl)-2-methyl-1H-pyrrole-3-carboxamide;
5-(5-amino-2-phenoxyphenyl)-2-methyl-1H-pyrrole-3-carboxamide;
2-methyl-5-{-[(methyl sulfonyl)amino]-2-phenoxyphenyl}-1H-pyrrole-3-carboxamide;
5-(1H-benzimidazol-4-yl)-2-methyl-1H-pyrrole-3-carboxamide;
5-(1H-indol-7-yl)-2-methyl-1H-pyrrole-3-carboxamide;
ethyl [4-(benzyloxy)-3-(4-carbamoyl-5-methyl-1H-pyrrol-2-yl)phenyl]acetate;
[4-(benzyloxy)-3-(4-carbamoyl-5-methyl-1H-pyrrol-2-yl)phenyl]acetic acid;
5-[2-(benzyloxy)-5-(2-hydroxyethyl)phenyl]-2-methyl-1H-pyrrole-3-carboxamide; and
5-[2-(2,4-difluorophenoxy)-5-sulfamoylphenyl]-2-methyl-1H-pyrrole-3-carboxamide.

12. A pharmaceutical composition comprising a pharmaceutically acceptable carrier and a therapeutically effective amount of a compound of claim 1, or a pharmaceutically acceptable salt thereof.

* * * * *